(12) United States Patent
Venema et al.

(10) Patent No.: US 7,459,292 B2
(45) Date of Patent: Dec. 2, 2008

(54) POLYNUCLEOTIDES AND EXPRESSION SYSTEM OF A NOVEL HUMAN G-PROTEIN COUPLED RECEPTOR

(75) Inventors: Jakob Venema, Weesp (NL); Claudia Berger, Hannover (DE); Christiane Löken, Hannover (DE); Willy Deleersnijder, Weesp (NL); Guy Nys, Weesp (NL)

(73) Assignee: Solvay Pharmaceuticals, Inc., Weesp (NL)

( * ) Notice: Subject to any disclaimer, the term of this patent is extended or adjusted under 35 U.S.C. 154(b) by 149 days.

(21) Appl. No.: 11/170,351

(22) Filed: Jun. 30, 2005

(65) Prior Publication Data

US 2005/0272123 A1    Dec. 8, 2005

Related U.S. Application Data

(63) Continuation of application No. 10/088,744, filed as application No. PCT/EP00/09584 on Sep. 25, 2000, now Pat. No. 6,998,255.

(60) Provisional application No. 60/222,047, filed on Jul. 31, 2000.

(30) Foreign Application Priority Data

Sep. 24, 1999  (EP)  .................................. 99203140
Sep. 24, 1999  (NL)  .................................. 1013140
Jul. 28, 2000   (EP)  .................................. 00202683

(51) Int. Cl.
*C12N 15/12*     (2006.01)
*C07K 14/705*    (2006.01)
*G01N 33/566*    (2006.01)

(52) U.S. Cl. .................. 435/69.1; 435/252.3; 435/320.1

(58) Field of Classification Search ....................... None
See application file for complete search history.

(56) References Cited

U.S. PATENT DOCUMENTS

| | | | |
|---|---|---|---|
| 5,482,835 A | 1/1996 | King et al. | |
| 6,461,836 B1 | 10/2002 | Elshourbagy et al. | |
| 6,800,749 B1 * | 10/2004 | Ahmad et al. | 536/23.5 |

FOREIGN PATENT DOCUMENTS

| | | |
|---|---|---|
| WO | WO90/01330 | 2/1990 |
| WO | WO99/55732 | 11/1999 |
| WO | WO00/22131 | 4/2000 |
| WO | WO00/31258 | 6/2000 |
| WO | WO 01/44297 A1 | 6/2001 |

OTHER PUBLICATIONS

GenBank Accession No. F07531, (2 pages), Feb. 1995.
GenBank Accession No. R13353, (2 pages), Apr. 1995.
GenBank Accession No. R13890, (2 pages), Apr. 1995.
GenBank Accession No. H11359, (2 pages), Jun. 1995.
GenBank Accession No. AQ019411, (2 pages), Jun. 1998.
GenBank Accession No. AQ015065, (2 pages), Jun. 1998.
GenBank Accession No. N45474, (2 pages), Feb. 1996.
GenBank Accession No. W61169, (2 pages), May 1996.
Accession No. G20615, (2 pages), 1996.
GenBank Accession No. AI432384, (2 pages), Feb. 1999.
GenBank Accession No. W61131, (2 pages), May 1996.
GenBank Accession No. AI023570, (2 pages), Jun. 1988.
GenBank Accession No. F01358, (2 pages), Feb. 1995.
GenBank Accession No. F03770, (2 pages), Feb. 1995.
GenBank Accession No. Z38158, (2 pages), Oct. 1994.
Accession No. G05725, (2 pages), 1995.
GenBank Accession No. R40869, (2 pages), May 1995.
GenBank Accession No. R37725, (2 pages), May 1995.
GenBank Accession No. H11333, (2 pages), Jun. 1995.
International Search Report for PCT/EP00/09584.
C.P. Tan et al., "Cloning and Characterization of a Human and Murine T-Cell Orphan G-Protein-Coupled Receptor Similar to the Growth Hormone Secretagogue and Neurotensin Receptors", Genomics, vol. 52, pp. 223-229, Jun. 1998.
Takeda Chemical Ind. Ltd., "DNA Encoding Human Neurotensin Receptor Protein Useful for Screening for Antagonists Used to Treat Parkinson's Disease, Depression, Dementia, Retrograde Oesophagitis, Ulcers", Patent Abstract of Japan No. JP 08143597, Jun. 4, 1996.
Doe Joint Genome Institute "Sequencing of Human Chromosome 5", pp. 1-5, Aug. 1999.
L. Hilllier, et al., "yy59b04r1 *Homo sapiens* cDNA Clone", 277807 5'The WashU-Merck EST Project, pp. 1-2, Feb. 1996 (Abstract).
L. Hillier et al., "zd31a03.r1 Soares Fetal Heart NbHH19W *Homo sapiens* cDNA Clone," 342220 5' WashU-Merck EST Project, p. 1, Sep. 1996.
L. Hillier et al., "ym13d04.r1 *Homo sapiens* cDNA Clone", 47842 5' The WashU-Merck EST Project, pp. 1-2, Jul 1995.

(Continued)

Primary Examiner—John D Ulm
(74) Attorney, Agent, or Firm—Finnegan, Henderson, Farabow, Garrett & Dunner, L.L.P.

(57) ABSTRACT

The present invention relates to novel identified polynucleotides, polypeptides encoded by them and to the use of such-polynucleotides and polypeptides, and to their production. More particularly, the polynucleotides and polypeptides of the present invention relate to the G-protein coupled receptor family, referred to as IGS4-family. The invention also relates to inhibiting or activating the action of such polynucleotides and polypeptides, to a vector containing said polynucleotides, a host cell containing such vector and transgenic animals where the IGS4-gene is either overexpressed, misexpressed, underexpressed or suppressed (knock-out animals). The invention further relates to a method for screening compounds capable to act as an agonist or an antagonist of said G-protein coupled receptor family IGS4. The invention also relates to the identification of the cognate ligand of the IGS4 polypeptides of the invention. High affinity binding to said IGS4 polypeptides is found for the neuropeptides known as neuromedin U.

15 Claims, 9 Drawing Sheets

OTHER PUBLICATIONS

K.K. McKee et al., "Cloning and Characterization of Two Human G Protein-Coupled Receptor Genes (GPR38 And GPR39) Related to the Growth Hormone Secretagogue and Neurotensin Receptors", Genomics, vol. 46, pp. 426-434, 1997.

N. Vita et al., "Cloning and Expression of a Complementary DNA Encoding a High Affinity Human Neurotensin Receptor", FEBS Letters, vol. 317, No. 1,2, pp. 139-142, Feb. 1993.

N. Vita et al., "Neurotensin is an Antagonist of the Human Neurotensin $NT_2$ Receptor Expressed in Chinese Hamster Ovary Cells", European Journal of Pharmacology, vol. 360, pp. 265-272, 1998.

A.D. Howard et al., "A Receptor in Pituitary and Hypothalamus That Functions in Growth Hormone Release", Science, vol. 273, (5277):974-977, Aug. 1996.

M. Hosoya et al., "Identification and Functional Characterization of a Novel Subtype of Neuromedin U Receptor", The Journal of Biological Chemistry, vol. 275, pp. 29528-29532, Sep. 2000.

P.G. Szekeres et al., "Neuromedin U is a Potent Agonist at the Orphan G Protein-Coupled Receptor FM3", The Journal of Biological Chemistry, vol. 275, pp. 20247-20250, Jul. 2000.

R. Fujii et al., "Identification of Neuromendin U as the Cognate Ligand of the Orphan G Protein-Coupled Receptor FM-3", The Journal of Biological Chemistry, vol. 275, pp. 21068-21074, Jul. 2000.

R. Raddatz et al., "Identification and Characterization of Two Neuromedin U Receptors Differentially Expressed in Peripheral Tissues and the Central Nervous System,"The Journal of Biological Chemistry, vol. 275, pp. 32452-32459, Oct. 2000.

L. Shan et al., "Identification of a Novel Neuromedin U Receptor Subtype Expressed in the Central Nervous Sytem," The Journal of Biological Chemistry, vol. 275, pp. 39482-39486, Dec. 2000.

J. Domin et al., "Neuromedin U—A Study of its Distribution in the Rat", Peptides, vol. 8, pp. 779-784, 1987.

NCBI Accession No. AC008571, (52 pages), Aug. 1999.

NCBI.NLM.NIH.GOV:80, No. 668353, (2 pages), Feb. 18, 1995.

NCBI.NLM.NIH.GOV:80, No. 668354, (2 pages), Feb. 18, 1995.

International Search Report for PCT/EP00/09584, mailed Sep. 4, 2001.

GenBank Accession No.: AQ078563, (2 pages), Aug. 1998.

* cited by examiner

Human multiple tissue expression array using a human IGS4 probe.

POLYNUCLEOTIDES AND EXPRESSION SYSTEM OF A NOVEL HUMAN G-PROTEIN COUPLED RECEPTOR

This is a continuation of application Ser. No. 10/088,744, which has a filing date of Mar. 22, 2002 now U.S. Pat. No. 6,998,255, as a 35 U.S.C. § 371 filing of PCT/EP00/09584 filed Sep. 25, 2000, which claims priority to EP application No. 99203140.1, filed Sep. 24, 1999, Netherlands application No. 1013140, filed Sep. 24, 1999, EP application No. 00202683.9, filed Jul. 28, 2000, and U.S. application No. 60/222,047, filed Jul. 31, 2000, all of which are incorporated herein by reference.

DESCRIPTION

The present invention relates to novel identified polynucleotides, polypeptides encoded by them and to the use of such polynucleotides and polypeptides, and to their production. More particularly, the polynucleotides and polypeptides of the present invention relate to a G-protein coupled receptor (GPCR), hereinafter referred to as IGS4. IGS4 exists in two polymorphic forms, hereinafter referred to as IGS4A and IGS4B. The invention also relates to inhibiting or activating the action of such polynucleotides and polypeptides, to a vector containing said polynucleotides, a host cell containing such vector and transgenic animals where the IGS4-gene is either overexpressed, misexpressed, underexpressed and/or suppressed (knock-out animals). The invention further relates to a method for screening compounds capable to act as an agonist or an antagonist of said G-protein coupled receptor IGS4, and to the cognate ligand of IGS4.

BACKGROUND OF THE INVENTION

It is well established that many medically significant biological processes are mediated by proteins participating in signal transduction pathways that involve G-proteins and/or second messengers; e.g., cAMP (Lefkowitz, Nature, 1991, 351:353-354). Herein these proteins are referred to as proteins participating in pathways with G-proteins. Some examples of these proteins include the GPC receptors; such as those for adrenergic agents and dopamine (Kobilka, B. K., et al., Proc. Natl. Acad. Sci., USA, 1987, 84:46-50; Kobilka, B. K., et al., Science, 1987, 238:650-656; Bunzow, J. R., et al., Nature, 1988, 336:783-787), G-proteins themselves, effector proteins, e.g., phospholipase C, adenylate cyclase, and phosphodiesterase, and actuator proteins, e.g., protein kinase A and protein kinase C (Simon, M. I., et al., Science, 1991, 252:802-8).

For example, in one form of signal transduction, upon hormone binding to a GPCR the receptor interacts with the heterotrimeric G-protein and induces the dissociation of GDP from the guanine nucleotide-binding site. At normal cellular concentrations of guanine nucleotides, GTP fills the site immediately. Binding of GTP to the α subunit of the G-protein causes the dissociation of the G-protein from the receptor and the dissociation of the G-protein into α and βγ subunits. The GTP-carrying form then binds to activated adenylate cyclase. Hydrolysis of GTP to GDP, catalyzed by the G-protein itself (α subunit possesses an intrinsic GTPase activity), returns the G-protein to its basal, inactive form. The GTPase activity of the α subunit is, in essence, an internal clock that controls an on/off switch. The GDP bound form of the α subunit has high affinity for βγ and subsequent reassociation of αGDP with αγ returns the system to the basal state. Thus the G-protein serves a dual role, as an intermediate that relays the signal from receptor to effector (in this example adenylate cyclase), and as a clock that controls the duration of the signal.

The membrane bound superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

The G-protein coupled receptor family includes dopamine receptors which bind to neuroleptic drugs used for treating CNS disorders. Other examples of members of this family include, but are not limited to calcitonin, adrenergic, neuropeptidey, somastotatin, neurotensin, neurokinin, capsaicin, VIP, CGRP, CRF, CCK, bradykinin, galanin, motilin, nociceptin, endothelin, cAMP, adenosine, muscarinic, acetylcholine, serotonin, histamine, thrombin, kinin, follicle stimulating hormone, opsin, endothelial differentiation gene-1, rhodopsin, odorant, and cytomegalovirus receptors.

Most G-protein coupled receptors have single conserved cysteine residues in each of the first two extracellular loops which form disulfide bonds that are believed to stabilize functional protein structures. The 7 transmembrane regions are designated as TM1, TM2, TM3, TM4, TM5, TM6 and TM7. The cytoplasmic loop which connects TM5 and TM6 may be a major component of the G-protein binding domain.

Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

Recently, it was discovered that certain GPCRs, like the calcitonin-receptor like receptor, might interact with small single pass membrane proteins called receptor activity modifying proteins (RAMP's). This interaction of the GPCR with a certain RAMP is determining which natural ligands have relevant affinity for the GPCR-RAMP combination and regulate the functional signaling activity of the complex (McLathie, L. M. et al., Nature (1998) 393:333-339).

For some receptors, the ligand binding sites of G-protein coupled receptors are believed to comprise hydrophilic sockets formed by several G-protein coupled receptor transmembrane domains, said sockets being surrounded by hydrophobic residues of the G-protein coupled receptors. The hydrophilic side of each G-protein coupled receptor transmembrane helix is postulated to face inward and form a polar ligand-binding site. TM3 has been implicated in several G-protein coupled receptors as having a ligand-binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc. Rev., 1989, 10:317-331). Different G-protein α-subunits preferentially stimulate particular effectors to modulate various biological functions in a cell. Phosphorylation of cytoplasmic residues of G-protein coupled receptors has been identified as an important mechanism for the regulation of G-protein coupling of some G-protein coupled receptors. G-protein coupled receptors are found in numerous sites within a mammalian host.

Receptors—primarily the GPCR class—have led to more than half of the currently known drugs (Drews, Nature Biotechnology, 1996, 14: 1516). This indicates that these receptors have an established, proven history as therapeutic targets. Clearly there is a need for identification and characterization of further receptors which can play a role in preventing, ameliorating or correcting dysfunctions or diseases, including, but not limited to PNS, psychiatric and CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; attention deficit/ hyperactivity disorder (ADHD); cardiovascular diseases, including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders, including irritable bowel syndrome (IBS), inflammatory bowel disease (IBD), gastroesophagal reflux disease (GERD), motility disorders and conditions of delayed gastric emptying, such as post operative or diabetic gastroparesis, and diabetes, ulcers—e.g. gastric ulcer, diarrhoea, other diseases including osteoporosis; inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus; and gynaecological disorders.

SUMMARY OF THE INVENTION

In one aspect, the invention relates to IGS4 polypeptides (including the IGS4A and IGS4B polypeptide polymorphs), polynucleotides and recombinant materials and methods for their production. Another aspect of the invention relates to methods for using such IGS4 polypeptides, polynucleotides and recombinant materials. Such uses include, but are not limited to, use as a therapeutic target and for the treatment of PNS, psychiatric and CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; attention deficit/hyperactivity disorder (ADHD); cardiovascular diseases, including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders, including irritable bowel syndrome (IBS), inflammatory bowel disease (IBD), gastroesophageal reflux disease (GERD), motility disorders and conditions of delayed gastric emptying, such as post operative or diabetic gastroparesis, and diabetes, ulcers—e.g. gastric ulcer; diarrhoea; other diseases including osteoporosis; inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus; and gynaecological disorders, among others. Preferred uses of the invention relate to disorders of the nervous system, including the central nervous system (CNS) and the peripheral nervous system (PNS), disorders of the gastrointestinal system and/or of the cardiovascular system and/or of skeletal muscle and/or of the thyroid, and/or also to lung diseases, immunological diseases and disorders of the genitourinary system.

In still another aspect, the invention relates to methods to identify agonists and antagonists using the materials provided by the invention, and treating conditions associated with IGS4 imbalance with the identified compounds. Yet another aspect of the invention relates to diagnostic assays for detecting diseases associated with inappropriate IGS4 activity or levels. A further aspect of the invention relates to animal-based systems which act as models for disorders arising from aberrant expression or activity of IGS4. Preferred agonists or antagonists identified according to the present invention are those which are suited for the treatment of disorders of the nervous system, including the central nervous system (CNS) and the peripheral nervous system (PNS), disorders of the gastrointestinal system and/or of the cardiovascular system and/or of skeletal muscle and/or of the thyroid, and/or also to lung diseases, immunological diseases and disorders of the genitourinary system.

The invention also relates to the identification of the cognate ligand of the IGS4 polypeptides of the invention. High affinity binding to said IGS4 polypeptides is found for the neuropeptides known as neuromedin U.

Table 1: IGS4A-DNA of SEQ ID NO: 1 and SEQ ID NO: 3

TABLE 1

IGS4A-DNA of SEQ ID NO: 1 and SEQ ID NO: 3

5'-
GGCTCAGCTTGAAACAGAGCCTCGTACCAGGGGAGGCTCAGGCCTTGGATTTTAATGTCA

GGGATGGAAAAACTTCAGAATGCTTCCTGGATCTACCAGCAGAAACTAGAAGATCCATTC

CAGAAACACCTGAACAGCACCGAGGAGTATCTGGCCTTCCTCTGCGGACCTCGGCGCAGC

CACTTCTTCCTCCCCGTGTCTGTGGTGTATGTGCCAATTTTTGTGGTGGGGGTCATTGGC

TABLE 1-continued

IGS4A-DNA of SEQ ID NO: 1 and SEQ ID NO: 3

AATGTCCTGGTGTGCCTGGTGATTCTGCAGCACCAGGCTATGAAGACGCCCACCAACTAC

TACCTCTTCAGCCTGGCGGTCTCTGACCTCCTGGTCCTGCTCCTTGGAATGCCCCTGGAG

GTCTATGAGATGTGGCGCAACTACCCTTTCTTGTTCGGGCCCGTGGGCTGCTACTTCAAG

ACGGCCCTCTTTGAGACCGTGTGCTTCGCCTCCATCCTCAGCATCACCACCGTCAGCGTG

GAGCGCTACGTGGCCATCCTACACCCGTTCCGCGCCAAACTGCAGAGCACCCGGCGCCGG

GCCCTCAGGATCCTCGGCATCGTCTGGGGCTTCTCCGTGCTCTTCTCCCTGCCCAACACC

AGCATCCATGGCATCAAGTTCCACTACTTCCCCAATGGGTCCCTGGTCCCAGGTTCGGCC

ACCTGTACGGTCATCAAGCCCATGTGGATCTACAATTTCATCATCCAGGTCACCTCCTTC

CTATTCTACCTCCTCCCCATGACTGTCATCAGTGTCCTCTACTACCTCATGGCACTCAGA

CTAAAGAAAGACAAATCTCTTGAGGCAGATGAAGGGAATGCAAATATTCAAAGACCCTGC

AGAAAATCAGTCAACAAGATGCTGTTTGTCTTGGTCTTAGTGTTTGCTATCTGTTGGGCC

CCGTTCCACATTGACCGACTCTTCTTCAGCTTTGTGGAGGAGTGGAGTGAATCCCTGGCT

GCTGTGTTCAACCTCGTCCATGTGGTGTCAGGTGTCTTCTTCTACCTGAGCTCAGCTGTC

AACCCCATTATCTATAACCTACTGTCTCGCCGCTTCCAGGCAGCATTCCAGAATGTGATC

TCTTCTTTCCACAAACAGTGGCACTCCCAGCATGACCCACAGTTGCCACCTGCCCAGCGG

AACATCTTCCTGACAGAATGCCACTTTGTGGAGCTGACCGAAGATATAGGTCCCCAATTC

CCATGTCAGTCATCCATGCACAACTCTCACCTCCCAACAGCCCTCTCTAGTGAACAGATG

TCAAGAACAAACTATCAAAGCTTCCACTTTAACAAAACCTGAATTCTTTCAGAGCTGACT

CTCCTCTATGCCTCAAAACTTCAGAGAGGAACATCCCATAATGTATGCCTTCTCATATGA

TATTAGAGAGGTAGAATGGCTCTTACAACTCATGTACCCATTGCTAGTTTTTTTTTTTA

ATAAACGTGAAAACTGAGAGTTAGATCTGGTTTCAAAACCCAAGACTGCCTGATTTTTAG

TTATCTTTCCACTATCCTAACTGCCTCATGCCCCTTCACTAGTTCATGCCAAGAACGTGA

CTGGAAAGGCATGGCACCTATACCTTGATTAATTTCCATTAATGGAAATGGTTCGTCCTG

AGTCATCTACGTTCCGAGTCAGGCTGTCACTCCTACTA-3'

TABLE 2

IGS4B-DNA of SEQ ID NO: 5 and SEQ ID NO: 7

5'-
GGCTCAGCTTGAAACAGAGCCTCGTACCAGGGGAGGCTCAGGCCTTGGATTTTAATGTCA

GGGATGGAAAAACTTCAGAATGCTTCCTGGATCTACCAGCAGAAACTAGAAGATCCATTC

CAGAAACACCTGAACAGCACCGAGGAGTATCTGGCCTTCCTCTGCGGACCTCGGCGCAGC

CACTTCTTCCTCCCCGTGTCTGTGGTGTATGTGCCAATTTTTGTGGTGGGGGTCATTGGC

AATGTCCTGGTGTGCCTGGTGATTCTGCAGCACCAGGCTATGAAGACGCCCACCAACTAC

TACCTCTTCAGCCTGGCGGTCTCTGACCTCCTGGTCCTGCTCCTTGGAATGCCCCTGGAG

GTCTATGAGATGTGGCGCAACTACCCTTTCTTGTTCGGGCCCGTGGGCTGCTACTTCAAG

ACGGCCCTCTTTGAGACCGTGTGCTTCGCCTCCATCCTCAGCATCACCACCGTCAGCGTG

GAGCGCTACGTGGCCATCCTACACCCGTTCCGCGCCAAACTGCAGAGCACCCGGCGCCGG

GCCCTCAGGATCCTCGGCATCGTCTGGGGCTTCTCCGTGCTCTTCTCCCTGCCCAACACC

AGCATCCATGGCATCAAGTTCCACTACTTCCCCAATGGGTCCCTGGTCCCAGGTTCGGCC

TABLE 2-continued

IGS4B-DNA of SEQ ID NO: 5 and SEQ ID NO: 7

ACCTGTACGGTCATCAAGCCCATGTGGATCTACAATTTCATCATCCAGGTCACCTCCTTC

CTATTCTACCTCCTCCCCATGACTGTCATCAGTGTCCTCTACTACCTCATGGCACTCAGA

CTAAAGAAAGACAAATCTCTTGAGGCAGATGAAGGGAATGCAAATATTCAAAGACCCTGC

AGAAAATCAGTCAACAAGATGCTGTTTGTCTTGGTCTTAGTGTTTGCTATCTGTTGGGCC

CCGTTCCACATTGACCGACTCTTCTTCAGCTTTGTGGAGGAGTGGAGTGAATCCCTGGCT

GCTGTGTTCAACCTCGTCCATGTGGTGTCAGGTGTCTTCTTCTACCTGAGCTCAGCTGTC

AACCCCATTATCTATAACCTACTGTCTCGCCGCTTCCAGGCAGCATTCCAGAATGTGATC

TCTTCTTTCCACAAACAGTGGCACTCCCAGCATGACCCACAGTTGCCACCTGCCCAGCGG

AACATCTTCCTGACAGAATGCCACTTTGTGGAGCTGACCGAAGATATAGGTCCCCAATTC

CTATGTCAGTCATCCGTGCACAACTCTCACCTCCCAACAGCCCTCTCTAGTGAACAGATG

TCAAGAACAAACTATCAAAGCTTCCACTTTAACAAAACCTGAATTCTTTCAGAGCTGACT

CTCCTCTATGCCTCAAAACTTCAGAGAGGAACATCCCATAATGTATGCCTTCTCATATGA

AATTAGAGAGGTAGAATGGCTCTTACAACTCATGTACCCATTGCTAGTTTTTTTTTTTA

ATAAACGTGAAAACTGAGAGTTAGATCTGGTTTCAAAACCCAAGACTGCCTGATTTTTAG

TTATCTTTCCACTATCCTAACTGCCTCATGCCCCTTCACTAGTTCATGCCAAGAACGTGA

CTGGAAAGGCATGGCACCTATACCTTGATTAATTTCCATTAATGGAAATGGTTCGTCCTG

AGTCATCTACGTTCCGAGTCAGGCTGTCACTCCTACTA-3'

TABLE 3

IGS4A-64-DNA of SEQ ID NO: 9 and SEQ ID NO: 11

5'-
GGCTCAGCTTGAAACAGAGCCTCGTACCAGGGGAGGCTCAGGCCTTGGATTTTAATGTCA

GGGATGGAAAAACTTCAGAATGCTTCCTGGATCTACCAGCAGAAACTAGAAGATCCATTC

CAGAAACACCTGAACAGCACCGAGGAGTATCTGGCCTTCCTCTGCGGACCTCGGCGCAGC

CACTTCTTCCTCCCCGTGTCTGTGGTGTATGTGCCAATTTTTGTGGTGGGGGTCATTGGC

AATGTCCTGGTGTGCCTGGTGATTCTGCAGCACCAGGCTATGAAGACGCCCACCAACTAC

TACCTCTTCAGCCTGGCGGTCTCTGACCTCCTGGTCCTGCTCCTTGGAATGCCCCTGGAG

GTCTATGAGATGTGGCGCAACTACCCCTTTCTTGTTCGGGCCCGTGGGCTGCTACTTCAAG

ACGGCCCTCTTTGAGACCGTGTGCTTCGCCTCCATCCTCAGCATCACCACCGTCAGCGTG

GAGCGCTACGTGGCCATCCTACACCCGTTCCGCGCCAAACTGCAGAGCACCCGGCGCCGG

GCCCTCAGGATCCTCGGCATCGTCTGGGGCTTCTCCGTGCTCTTCTCCCTGCCCAACACC

AGCATCCATGGCATCAAGTTCCACTACTTCCCCAATGGGTCCCTGGTCCCAGGTTCGGCC

ACCTGTACGGTCATCAAGCCCATGTGGATCTACAATTTCATCATCCAGGTCACCTCCTTC

CTATTCTACCTCCTCCCCATGACTGTCATCAGTGTCCTCTACTACCTCATGGCACTCAGA

CTAAAGAAAGACAAATCTCTTGAGGCAGATGAAGGGAATGCAAATATTCAAAGACCCTGC

AGAAAATCAGTCAACAAGATGCTGTTTGTCTTGGTCTTAGTGTTTGCTATCTGTTGGGCC

TGTTCAACCTCGTCCATGTGGTGTCAGGGTTCTTCTTCTACCTGAGCTCAGCTGTCAACC

CCATTATCTATAACCTACTGTCTCGCCGCTTCCAGGCAGCATTCCAGAATGTGATCTCTT

TABLE 3-continued

IGS4A-64-DNA of SEQ ID NO: 9 and SEQ ID NO: 11

CTTTCCACAAACAGTGGCACTCCCAGCATGACCCACAGTTGCCACCTGCCCAGCGGAACA
TCTTCCTGACAGAATGCCACTTTGTGGAGCTGACCGAAGATATAGGTCCCCAATTCCCAT
GTCAGTCATCCATGCACAACTCTCACCTCCCAACAGCCCTCTCTAGTGAACAGATGTCAA
GAACAAACTATCAAAGCTTCCACTTTAACAAAACCTGAATTCTTTCAGAGCTGACTCTCC
TCTATGCCTCAAAACTTCAGAGAGGAACATCCCATAATGTATGCCTTCTCATATGATATT
AGAGAGGTAGAATGGCTCTTACAACTCATGTACCCATTGCTAGTTTTTTTTTTTAATAA
ACGTGAAAACTGAGAGTTAGATCTGGTTTCAAAACCCAAGACTGCCTGATTTTTAGTTAT
CTTTCCACTATCCTAACTGCCTCATGCCCCTTCACTAGTTCATGCCAAGAACGTGACTGG
AAAGGCATGGCACCTATACCTTGATTAATTTCCATTAATGGAAATGGTTCGTCCTGAGTC
ATCTACGTTCCGAGTCAGGCTGTCACTCCTACTA-3'

TABLE 4

IGS4A-protein of SEQ ID NO: 2 and SEQ ID NO: 4 (without the three amino acids between brackets).

(MSG) MEKLQNASWIYQQKLEDPFQKHLNSTEEYLAFLCGPRRSHFFLPVSVVYVPIFVVGV
IGNVLVCLVILQHQAMKTPTNYYLFSLAVSDLLVLLLGMPLEVYEMWRNYPFLFGPVGCY
FKTALFETVCFASILSITTVSVERYVAILHPFRAKLQSTRRRALRILGIVWGFSVLFSLP
NTSIHGIKFHYFPNGSLVPGSATCTVIKPMWIYNFIIQVTSFLFYLLPMTVISVLYYLMA
LRLKKDKSLEADEGNANIQRPCRKSVNKMLFVLVLVFAICWAPFHIDRLFFSFVEEWSES
LAAVFNLVHVVSGVFFYLSSAVNPIIYNLLSRRFQAAPQNVISSFHKQWHSQHDPQLPPA
QRNIFLTECHFVELTEDIGPQFPCQSSMHNSHLPTALSSEQMSRTNYQSFHFNKT

TABLE 5

IGS4B-protein of SEQ ID NO: 6 and SEQ ID NO: 8 (without the three amino acids between brackets).

(MSG) MEKLQNASWIYQQKLEDPFQKHLNSTEEYLAFLCGPRRSHFFLPVSVVYVPIFVVGV
IGNVLVCLVILQHQAMKTPTNYYLFSLAVSDLLVLLLGMPLEVYEMWRNYPFLFGPVGCY
FKTALFETVCFASILSITTVSVERYVAILHPFRAKLQSTRRRALRILGIVWGFSVLFSLP
NTSIHGIKFHYFPNGSLVPGSATCTVIKPMWIYNFIIQVTSFLFYLLPMTVISVLYYLMA
LRLKKDKSLEADEGNANIQRPCRKSVNKMLFVLVLVFAICWAPFHIDRLFFSFVEEWTES
LAAVFNLVHVVSGVLFYLSSAVNPIIYNLLSRRFQAAFQNVISSFHKQWHSQHDPQLPPA
QRNIFLTECHFVELTEDIGPQFLCQSSVHNSHLPTALSSEQMSRTNYQSFHFNKT

TABLE 6

IGS4A-64-protein of SEQ ID NO: 10 and SEQ ID NO: 12 (without three amino acids between brackets).

(MSG) MEKLQNASWIYQQKLEDPFQKHLNSTEEYLAFLCGPRRSHFFLPVSVVYVPIFVVGV
IGNVLVCLVILQHQAMKTPTNYYLFSLAVSDLLVLLLGMPLEVYEMWRNYPFLFGPVGCY
FKTALFETVCFASILSITTVSVERYVAILHPFRAKLQSTRRRALRILGIVWGFSVLFSLP
NTSIHGIKFHYFPNGSLVPGSATCTVIKPMWIYNFIIQVTSFLFYLLPMTVISVLYYLMA
LRLKKDKSLEADEGNANIQRPCRKSVNKMLSLWRSGVNPWLLCSTSSMWCQVSSST

DESCRIPTION OF THE INVENTION

Definitions

The following definitions are provided to facilitate understanding of certain terms used frequently herein.

"IGS4" refers, among others, to a polypeptide comprising the amino acid sequence set forth in SEQ ID NO: 2 or SEQ ID NO: 4 (IGS4A) and SEQ ID NO: 6 or SEQ ID NO: 8 (IGS4B), or a variant thereof. Particularly preferred are polypeptides of IGS4B.

"Receptor Activity" or "Biological Activity of the Receptor" refers to the metabolic or physiologic function of said IGS4 including similar activities or improved activities or these activities with decreased undesirable side effects. Also included are antigenic and immunogenic activities of said IGS4.

"IGS4-gene" refers to a polynucleotide comprising the nucleotide sequence set forth in SEQ ID NO: 1, SEQ ID NO: 3, SEQ ID NO: 5 or SEQ ID NO: 7 or variants thereof and/or their complements.

"Antibodies" as used herein includes polyclonal and monoclonal antibodies, chimeric, single chain, and humanized antibodies, as well as Fab fragments, including the products of a Fab or other immunoglobulin expression library.

"Isolated" means altered "by the hand of man" from the natural state and/or separated from the natural environment. Thus, if an "isolated" composition or substance that occurs in nature has been "isolated", it has been changed or removed from its original environment, or both. For example, a polynucleotide or a polypeptide naturally present in a living animal is not "isolated", but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" may also include triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to short chains, commonly referred to as peptides, oligopeptides or oligomers, and to longer chains, generally referred to as proteins, and/or to combinations thereof. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well-described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol; cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth. Enzymol. (1990) 182:626-646 and Rattan et al., "Protein Synthesis: Posttranslational Modifications and Aging", Ann. NY Acad. Sci. (1992) 663:48-62.

"Variant" as the term is used herein, is a polynucleotide or polypeptide that differs from a reference polynucleotide or polypeptide respectively, but retains essential properties such as essential biological, structural, regulatory or biochemical propeties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed.; Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., SIAM J. Applied Math. (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., SIAM J. Applied Math. (1988) 48:1073. Methods to determine identity and similarity are codified in computer programs. Preferred computer program methods to determine identity and similarity between two sequences include, but are not limited to, GCG program package (Devereux, J., et al., Nucleic Acids Research (1984) 12(1):387), BLASTP, BLASTN, FASTA (Atschul, S. F. et al., J. Molec. Biol. (1990) 215:403). The word "homology" may substitute for the word "identity".

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five nucleotide differences per each 100 nucleotides of the reference nucleotide sequence of SEQ ID NO: 1. In other words, to obtain a polynucleotide having a nucleotide sequence at least 95% identical to a reference nucleotide sequence, up to any 5% of the nucleotides in the reference sequence may be deleted or substituted with another nucleotide, or a number of nucleotides up to any 5% of the total nucleotides in the reference sequence may be inserted into the reference sequence, or in a number of nucleotides of up to any 5% of the total nucleotides in the reference sequence there may be a combination of deletion, insertion and substitution. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO: 2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to any 5% of the amino acid residues in the reference sequence may be deleted or substituted with another amino acid, or a number of amino acids up to any 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to IGS4 polypeptides (or IGS4 proteins). The IGS4 polypeptides include the polypeptide of SEQ ID NO: 2, SEQ ID NO: 4, SEQ ID NO: 6 and SEQ ID NO: 8 and the polypeptide having the amino acid sequence encoded by the DNA insert contained in the deposit no. CBS102221 or deposit no. CBS102222, deposited on Sep. 24, 1999 at the Centraalbureau voor Schimmelcultures at Baam the Netherlands; as well as polypeptides comprising the amino acid sequence of SEQ ID NO: 2, SEQ ID NO: 4, SEQ ID NO: 6 or SEQ ID NO: 8 and the polypeptide having the amino acid sequence encoded by the DNA insert contained in the deposit no. CBS102221 or deposit no. CBS102222 at the Centraalbureau voor Schimmelcultures at Baam the Netherlands and polypeptides comprising the amino acid sequence which have at least 80% identity to that of SEQ ID NO: 2, SEQ ID NO: 4, SEQ ID NO: 6 or SEQ ID NO: 8 and/or the polypeptide having the amino acid sequence encoded by the DNA insert contained in the deposit no. CBS102221 or deposit no. CBS102222 at the Centraalbureau voor Schimmelcultures at Baam the Netherlands over its entire length, and still more preferably at least 90% identity, and even still more preferably at least 95% identity to said amino acid sequences. Furthermore, those with at least 97%, in particular at least 99%, are highly preferred. Also included within IGS4 polypeptides are polypeptides having the amino acid sequence which has at least 80% identity to the polypeptide having the amino acid sequence of SEQ ID NO: 2, SEQ ID NO: 4, SEQ ID NO: 6 or SEQ ID NO: 8 or the polypeptide having the amino acid sequence encoded by the DNA insert contained in the deposit no. CBS102221 or deposit no. CBS102222 at the Centraalbureau voor Schimmelcultures at Baam the Netherlands over its entire length, and still more preferably at least 90% identity, and even still more preferably at least 95% identity to SEQ ID NO: 2, SEQ ID NO: 4, SEQ ID NO: 6 or SEQ ID NO: 8. Furthermore, those with at least 97%, in particular at least 99% are highly preferred. Preferably IGS4 polypeptides exhibit at least one biological activity of the receptor.

In an additional embodiment of the invention, the IGS4 polypeptides may be a part of a larger protein such as a fusion protein. It is often advantageous to include an additional amino acid sequence which contains secretory or leader sequences, pro-sequences, sequences which aid in purification such as multiple histidine residues, sequences which aid in detection such as antigenic peptide tags (such as the haemagglutinin (HA) tag), or an additional sequence for stability during recombinant production.

Fragments of the IGS4 polypeptides are also included in the invention. A fragment is a polypeptide having an amino acid sequence that is the same as part of, but not all of, the amino acid sequence of the aforementioned IGS4 polypeptides. As with IGS4 polypeptides, fragments may be "freestanding," or comprised within a larger polypeptide of which they form a part or region, most preferably as a single continuous region. Representative examples of polypeptide fragments of the invention, include, for example, fragments from about amino acid number 1-20; 21-40, 41-60, 61-80, 81-100; and 101 to the end of IGS4 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of IGS4 polypeptides, except for deletion of a continuous series of residues that includes the amino terminus, or a continuous series of residues that includes the carboxyl terminus or deletion of two continuous series of residues, one including the amino terminus and one including the carboxyl terminus. An example of a truncated polypeptide according to the present invention is the polypetide of SEQ ID NO: 10 and SEQ ID NO: 12, which is encoded by the polynucleotide of SEQ ID NO: 9 respectively SEQ ID NO: 11. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate receptor activity, including those with a similar activity or an improved activity, or with a decreased undesirable activity. Also included are those that are antigenic or immunogenic in an animal, especially in a human.

Thus, the polypeptides of the invention include polypeptides having an amino acid sequence at least 80% identical to that of SEQ ID NO: 2, SEQ ID NO: 4, SEQ ID NO: 6 or SEQ ID NO: 8 and/or the polypeptide having the amino acid sequence encoded by the DNA insert contained in the deposit no. CBS102221 or the deposit no. CBS102222 at the Centraalbureau voor Schimmelcultures at Baam the Netherlands, or fragments thereof with at least 80% identity to the corresponding fragment. Preferably, all of these polypeptide fragments retain the biological activity of the receptor, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5-10, 1-5, or 1-2 amino acids are substituted, deleted, or added in any combination.

With regard to the polypeptides of the present invention it was also fiund that they show a high affinity binding for neuromedin U, in particular for neuromedin U-8 (an oligopeptide of 8 amino acids), neuromedin U-23 (an oligopeptide of 23 amino acids) and/or neuromedin U-25 (an oligopeptide of 25 amino acids). In the context of the present invention the term "high affinity" is understood as to describe a ligand binding showing log $EC_{50}$ values of at least below −6.00 (approx. 660 nM), preferably log $EC_{50}$ below −7.00 (approx. 55 nM), more preferably log $EC_{50}$ below −9.00 (approx. 500 pM to 1.2 nM), and most preferably log $EC_{50}$ below −10.00 (approx. 50-100 pM).

Two forms of the neuropeptide neuromedin U, neuromedin U-8 and neuromedin U-25, are described in the literature as uterus stimulating and hypertensive peptides (Minamino et al., 1985, Biochem. Biophys. Res. Commun. 130:1078-1085) being originally isolated from the porcine spinal cord. For neuromedin U-23, an oligopeptide of 23 amino acids, see for example: Okimura et al., Pept. Chem. (1995), Vol. Date 1994, 32:321-324; Salmon et al., J. Biol. Chem. (2000), 275(7), 4549-4554. Neuromedin U (NMU) was subsequently isolated from a number of species, e.g. from rat (NMU-23), human (NMU-25), frog (NMU-25), dog (NMU-8 and NMU-25), rabbit (NMU-25), and chicken (NMU-25). Thus, Domin et al. described the characterization of neuromedin U like immunoreactivity in rat, porcine, guinea pig and human tissue extracts using a specific radioimmunoassay (1986, Biochem. Biophys. Res. Commun. 140:1127-34). The primary structure of neuromedin U 23 from the rat ileum was established by Conlon et al. (1988, J. Neurochem. 51:988-991). Minamino et al. (1988, Biochem. Biophys. Res. Commun. 156:355-360) have isolated rat neuromedin U from the small intestine using mainly immunoaffinity chromatography and radioimmunoassay for pig neuromedin U-8, and the amino acid sequence of rat neuromedin U was determined by microsequence analysis and the structure was confirmed by synthesis. Although the C-terminal heptapeptide amide structure of pig neuromedin U is completely conserved in rat neuromedin U, the remainder of the peptide reveals nine amino acid replacements and two amino acid deletions when compared to pig neuromedin U-25. The distribution, primary structure, and relative biological activity of neuromedin U has been determined also in the frog Rana temporaria by Domin et al. (1989, J. Biol. Chem. 264:20881-20885) showing that the entire sequence was found to be an icosapentapeptide which displays marked sequence similarity to both porcine and rat neuromedin U. In a further study Domin et al. (1992, Regul. Pept. 41:1-8) have purified an avian homolog of neuromedin U from the chicken. Microsequence analysis characterized the peptide to be 25 amino acid residues long, and chicken neuromedin U showed marked sequence similarity with the porcine peptide at its bioactive C-terminal region. Isolation, structural characterization and pharmacological activity of dog neuromedin U-25 was described by O'Harte et al. (1991 Peptides 12:11-15). Furthermore, for rabbit neuromedin U-25 it was found that it lacks conservation of a post-translational processing site (Kage et al., 1991 Regul. Pept. 33:191-198); thus, in rabbit neuromedin U, the Arg16-Arg17 dibasic residue processing site that is found in pig and dog neuromedin U-25 is replaced by Arg-Gly, but this potential monobasic processing site is not utilized by cleavage enzyme(s) in the intestine.

Among the species studied the 5 amino acids at the C-terminus of the peptide were found to be almost totally conserved, suggesting that this region is of major importance. Thus, mammalian neuromedins share a common C-terminal sequence "-Phe-Leu-Phe-Arg-Pro-Arg-Asn-amide" [SEQ ID NO: 35] which appears to be essential for its biological activities. NMU is distributed both in the gastrointestinal tract and the central nervous System (CNS). In the rat, the highest concentration of neuromedin (NMU) was found in the ileum, followed by the pituitary, hypothalamus, spinal cord, thyroid, and the genitourinary tract. Immunohistochemistry studies showed that NMU immunoreactivity in the gut was only found in nerve fibers, mainly in the myenteric and submucous plexuses, and in the mucosa of all areas except stomach while no NMU immunoreactivity was found in endocrine cells. In the rat brain, NMU immunoreactivity was found in fibers widespread throughout the brain with the exception of the cerebellum. Human and rat genes encoding NMU precursor have been isolated. Both encode NMU at the C-terminus and other potential peptide products in the middle (Lo et al., 1992, J. Mol. Endocrinol. 6:1538-1544; Austin et al., 1995, J. Mol. Endocrinol. 14:157-169). High affinity NMU binding was characterized in rat uterus, and was shown to be sensitive to GTP- -S (Nandha et al., 1993, Endocrinology 133:482-486), suggesting that a receptor for NMU should be a G-protein coupled receptor. Nevertheless, the physiological role of NMU remains largely unknown. Neuromedin U (NMU) can cause potent contraction of smooth muscle, increase arterial blood pressure, modify intestinal ion transport, and at low doses stimulates the function and growth of the adrenal cortex. NMU was also shown to reduce the blood flow in superior enteric artery and portal vein while increasing blood flow slightly in pancreatic tissue.

Furthermore, according to the international patent application WO 90/01330 the neuromedins U-8 and U-25 are described to be suitable in the treatment of disorders of the gastrointestinal tract, e.g. being useful in the selective reduction of blood flow to the gastrointestinal tract, in the treatment of gastrointestinal bleeding and postprandial hypotension.

The IGS4 polypeptides of the present invention have been identified as a G-protein coupled receptor responsive to neuromedin U or ligands sufficiently similar thereto. Thus the IGS4 receptor, in particular the IGS4B receptor, responsive to neuromedin U will greatly facilitate the understanding of the physiological mechanisms of neuromedin U and other ligands sufficiently similar thereto, as well as of related diseases.

The tissue distribution of the polypeptides of the present invention and the expression levels are shown in the FIGS. 5-8, from which the skilled artisan can estimate the localisation and relevance of expression. For instance, with regard to the tissue distribution of the polypeptides of the present invention it was found, e.g. by MTE (multiple tissue expression) analysis, Northern blot analysis and Quantitative RT-PCR expression analysis that the IGS4 polypeptides of the present invention particularly are brought to expression with a medium level (relative to expression in testis as 100% in MTE blot, or in spinal cord as 100% in Quantitative RT-PCR analysis, respectively) e.g. in brain, skeletal muscle, cerebellum, thymus, medulla, thyroid, trachea, thalamus, substantia nigra, corpus callosum, caudate nucleus, pons, nucleus accumbens, fetal brain and stomach; and with a relevant level (if being detectable by Quantitative RT-PCR analysis) e.g. in heart, lung, and prostate. For instance, expression levels are considered to be medium if they amount at least 20% of the expression value found for the by far highest expression (set as 100%) in testis or spinal cord. For instance, expression levels are considered to be relevant if expression could be detected at least via Quantitative RT-PCR analysis. It will be appreciated that expression levels indicated for any organ are average values of expression levels in the specific tissues and cell types constituting the organ. Thus, if an expression level is just found to be relevant with respect to an organ, this does not necessarily exclude medium or even high expression levels locally within a specific region, e.g. in a specific tissue and/or cell type, of the organ.

These results suggest that IGS4 polypeptides preferably play a role in the nervous system, including the central nervous system (CNS) and the peripheral nervous system (PNS), in the gastrointestinal system and/or in the cardiovascular system and/or in skeletal muscle and/or in the thyroid, and/or also in lung diseases, immunological diseases and disorders of the genitourinary system.

Thus, in a further embodiment the invention pertains also to an isolated IGS4 polypeptide comprising an amino acid sequence of a neuromedin receptor protein, preferably of a mammalian neuromedin receptor protein, said protein exhibiting high affinity binding for neuromedin U, preferably for neuromedin U-8, for neuromedin U-23 and/or for neuromedin U-25. Particularly, the isolated IGS4 polypeptide comprising an amino acid sequence of a neuromedin receptor protein, is a protein exhibiting expression (being at least detectable via Northern and/or MTE and/or Quantitative RT-PCR analysis) in brain, skeletal muscle, cerebellum, testis, corpus callosum, spinal cord, substantia nigra, medulla, thalamus, caudate nucleus, pons, nucleus accumbens, fetal brain, stomach, heart, thyroid gland, lung, thymus, prostate and/or in trachea. In a variant of this embodiment the invention pertains to an isolated IGS4 polypeptide comprising an amino acid sequence of a neuromedin receptor protein, preferably of a mammalian neuromedin receptor protein, said protein exhibiting high affinity binding for neuromedin U, preferably for neuromedin U-8, for neuromedin U-23 and/or for neuromedin U-25, said protein exhibiting expression (being at least detectable via Northern and/or MTE and/or Quantitative RT-PCR analysis) in brain, skeletal muscle, cerebellum, testis, corpus callosum, spinal cord, substantia nigra, medulla, thalamus, caudate nucleus, pons, nucleus accumbens, fetal brain, stomach, heart, thyroid gland, lung, thymus, prostate and/or in trachea, and said amino acid sequence being selected from the group of amino acid sequence as already defined supra.

The IGS4 polypeptides of the invention can be prepared in any suitable manner. Such polypeptides include isolated naturally occurring polypeptides, recombinantly produced polypeptides, synthetically produced polypeptides, or polypeptides produced by a combination of these methods. Methods for preparing such polypeptides are well known in the art.

Polynucleotides of the Invention

A further aspect of the invention relates to IGS4 polynucleotides. IGS4 polynucleotides include isolated polynucleotides which encode the IGS4 polypeptides (including IGS4A and IGS4B) and fragments, and polynucleotides closely related thereto. More specifically, the IGS4 polynucleotide of the invention includes a polynucleotide comprising the nucleotide sequence contained in SEQ ID NO: 1, SEQ ID NO: 3, SEQ ID NO: 5 or SEQ ID NO: 7 encoding a IGS4A polypeptide of SEQ ID NO: 2 or of SEQ ID NO: 4 and a IGS4B polypeptide of SEQ ID NO: 6 or of SEQ ID NO: 8 respectively, polynucleotides having the particular sequence of SEQ ID NO: 1, SEQ ID NO: 3, SEQ ID NO: 5 or SEQ ID NO: 7 and polynucleotides which essentially correspond to the DNA insert contained in the deposit no. CBS102221 or the deposit no. CBS102222 at the Centraalbureau voor Schimmelcultures at Baam the Netherlands.

IGS4 polynucleotides further include polynucleotides comprising a nucleotide sequence that has at least 80% identity over its entire length to a nucleotide sequence encoding the IGS4 polypeptide of SEQ ID NO: 2, SEQ ID NO: 4, SEQ ID NO: 6 or SEQ ID NO: 8, a polynucleotide comprising a nucleotide sequence that is at least 80% identical to that of SEQ ID NO: 1, SEQ ID NO: 3, SEQ ID NO: 5 or SEQ ID NO: 7 over its entire length and a polynucleotide which essentially correspond to the DNA insert contained in the deposit no. CBS102221 or the deposit no. CBS102222 at the Centraalbureau voor Schimmelcultures at Baam the Netherlands.

In this regard, polynucleotides with at least 90% identity are particularly preferred, and those with at least 95% are especially preferred. Furthermore, those with at least 97% are highly preferred and those with at least 98-99% are most highly preferred, with at least 99% being the most preferred. Also included under IGS4 polynucleotides are a nucleotide sequence which has sufficient identity to a nucleotide sequence contained in SEQ ID NO: 1, SEQ ID NO: 3, SEQ ID NO: 5 or SEQ ID NO: 7 or to the DNA insert contained in the deposit no. CBS102221 or in the deposit no. CBS102222 at the Centraalbureau voor Schimmelcultures at Baam the Netherlands to hybridize under conditions useable for amplification or for use as a probe or marker. The invention also provides polynucleotides which are complementary to such IGS4 polynucleotides.

IGS4 of the invention is structurally related to other proteins of the G-protein coupled receptor family, as shown by the results of BLAST searches in the public databases. The amino acid sequence of Table 1 (SEQ ID NO: 2) has about 46% identity (using BLAST, Altschul S. F. et al. [1997], Nucleic Acids Res. 25:3389-3402) over most of its length (316 amino acid residues) with a human orphan G-protein coupled receptor (Accession # O43664, Tan et al., Genomics 52(2):223-229 (1998). There is 27% homology (over amino acid residues 61-349) to the rat neurotensin 1 receptor (Accession # P20789 Tanaka K. et al, Neuron 4:847-854 (1990)). The nucleotide sequence of Table 1 (SEQ ID NO: 1) is 63% identical to an orphan G-protein coupled receptor over nucleotide residues 120-864 (Accession # AF044600, corresponding with the protein sequence O43664). Furthermore, there is 53% identity to the human growth hormone secretagogue receptor over residues 94-1137 (Howard A. D. et al, Science 273:974-977(1996)). Thus, IGS4 polypeptides and polynucleotides of the present invention are expected to have, inter alia, similar biological functions/properties to their homologous polypeptides and polynucleotides, and their utility is obvious to anyone skilled in the art.

Polynucleotides of the invention can be obtained from natural sources such as genomic DNA. In particular, degenerated PCR primers can be designed that encode conserved regions within a particular GPCR gene subfamily. PCR amplification reactions on genomic DNA or cDNA using the degenerate primers will result in the amplification of several members (both known and novel) of the gene family under consideration (the degenerated primers must be located within the same exon, when a genomic template is used). (Libert et al., Science, 1989, 244: 569-572). Polynucleotides of the invention can also be synthesized using well-known and commercially available techniques (e.g. F. M. Ausubel et al, 2000, Current Protocols in Molecular Biology).

The nucleotide sequence encoding the IGS4 polypeptide of SEQ ID NO: 2, SEQ ID NO: 4, SEQ ID NO: 6 or SEQ ID NO: 8 may be identical to the polypeptide encoding sequence contained in SEQ ID NO: 1 (nucleotide number 55 to 1299) or SEQ ID NO: 3 (nucleotide number 64 to 1299), or SEQ ID NO; 5 (nucleotide number 55 to 1299) or SEQ ID NO: 7 (nucleotide number 64 to 1299) respectively, or it may be a different nucleotide sequence, which as a result of the redundancy (degeneracy) of the genetic code might also show alterations compared to the polypeptide encoding sequence contained in SEQ ID NO: 1, SEQ ID NO: 3, SEQ ID NO: 5 or SEQ ID NO: 7, but also encodes the polypeptide of SEQ ID NO: 2, SEQ ID NO: 4, SEQ ID NO: 6 or SEQ ID NO: 8, respectively.

In a further embodiment the invention pertains to an isolated nucleotide sequence encoding an IGS4 neuromedin receptor protein, preferably encoding a mammalian neuromedin receptor protein, said protein exhibiting high affinity binding for neuromedin U, preferably for neuromedin U-8, for neuromedin U-23 and/or for neuromedin U-25. Particularly, the isolated nucleotide sequence encodes an IGS4 neuromedin receptor protein which is a protein exhibiting expression (being at least detectable via Northern and/or MTE and/or Quantitative RT-PCR analysis) in brain, skeletal muscle, cerebellum, testis, corpus callosum, spinal cord, substantia nigra, medulla, thalamus, caudate nucleus, pons, nucleus accumbens, fetal brain, stomach, heart, thyroid gland, lung, thymus, prostate and/or in trachea. In a variant of this embodiment the invention pertains to an isolated nucleotide sequence encoding an IGS4 neuromedin receptor protein, preferably encoding a mammalian neuromedin receptor protein, said protein exhibiting high affinity binding for neuromedin U, preferably for neuromedin U-8, for neuromedin U-23 and/or for neuromedin U-25, said protein exhibiting expression (being at least detectable via Northern and/or MTE and/or Quantitative RT-PCR analysis) in brain, skeletal muscle, cerebellum, testis, corpus callosum, spinal cord, substantia nigra, medulla, thalamus, caudate nucleus, pons, nucleus accumbens, fetal brain, stomach, heart, thyroid gland, lung, thymus, prostate and/or in trachea, and said nucleotide sequence being selected from the group of nucleotide sequences as already defined supra.

When the polynucleotides of the invention are used for the recombinant production of the IGS4 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc. Natl. Acad. Sci USA (1989) 86:821-824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding IGS4 variants comprising the amino acid sequence of the IGS4 polypeptide of SEQ ID NO: 2, SEQ ID NO: 4, SEQ ID NO: 6 or SEQ ID NO: 8 in which several, 5-10, 1-5,1-3, 1-2 or 1 amino acid residues are substituted, deleted or added, in any combination.

The polynucleotides of the invention can be engineered using methods generally known in the art in order to alter IGS4-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create amino acid substitutions, create new restriction sites, alter modification (e.g. glycosylation or phosphorylation) patterns, change codon preference, produce splice variants, and so forth.

The present invention further relates to polynucleotides that hybridize to the herein above-described sequences. In this regard, the present invention especially relates to polynucleotides which hybridize under stringent conditions to the polynucleotides described above. As herein used, the term "stringent conditions" means hybridization will occur only if there is at least 80%, and preferably at least 90%, and more preferably at least 95%, yet even more preferably at least 97%, in particular at least 99% identity between the sequences.

Polynucleotides of the invention, which are identical or sufficiently identical to a nucleotide sequence contained in SEQ ID NO: 1, SEQ ID NO: 3, SEQ ID NO: 5 or SEQ ID NO: 7 or a fragment thereof, may be used as hybridization probes for cDNA and genomic DNA, to isolate full-length cDNAs and genomic clones encoding IGS4 and to isolate cDNA and genomic clones of other genes (including genes encoding homologs and orthologs from species other than human) that have a high sequence similarity to the IGS4 gene. People skilled in the art are well aware of such hybridization techniques. Typically these nucleotide sequences are 80% identical, preferably 90% identical, more preferably 95% identical to that of the referent. The probes generally will comprise at least 5 nucleotides, and preferably at least 8 nucleotides, and more preferably at least 10 nucleotides, yet even more preferably at least 12 nucleotides, in particular at least 15 nucleotides. Most preferred, such probes will have at least 30 nucleotides and may have at least 50 nucleotides. Particularly preferred probes will range between 30 and 50 nucleotides.

One embodiment, to obtain a polynucleotide encoding the IGS4 polypeptide, including homologs and orthologs from species other than human, comprises the steps of screening an appropriate library under stringent hybridization conditions with a labeled probe having the SEQ ID NO: 1, SEQ ID NO: 3, SEQ ID NO: 5 or SEQ ID NO: 7 or a fragment thereof, and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate (w/v), and 20 microgram/ml denatured, sheared salmon sperm DNA, followed by washing the filters in 0.1×SSC at about 65° C.

The polynucleotides and polypeptides of the present invention may be used as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be used to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, Cl 27, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals, i.e. derived from a different species.

If the IGS4 polypeptide is to be expressed for use in screening assays, generally, it is preferred that the polypeptide be produced at the surface of the cell. In this event, the cells may be harvested prior to use in the screening assay. In case the affinity or functional activity of the IGS4 polypeptide is modified by receptor activity modifying proteins (RAMP), coexpression of the relevant RAMP most likely at the surface of the cell is preferred and often required. Also in this event harvesting of cells expressing the IGS4 polypeptide and the relevant RAMP prior to use in screening assays is required. If the IGS4 polypeptide is secreted into the medium, the medium can be recovered in order to recover and purify the polypeptide; if produced intracellularly, the cells must first be lysed before the polypeptide is recovered. Membranes expressing the IGS4 polypeptide can be recovered by methods that are well known to a person skilled in the art. In general, such methods include harvesting of the cells expressing the IGS4 polypeptide and homogenization of the cells by a method such as, but not limited to, pottering. The membranes may be recovered by washing the suspension one or several times.

IGS4 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well-known techniques for refolding proteins may be employed to regenerate active conformation when the polypeptide is denatured during isolation and or purification.

Diagnostic Assays

This invention also relates to the use of IGS4 polynucleotides for use as diagnostic reagents. Detection of a mutated form of the IGS4 gene associated with a dysfunction will provide a diagnostic tool that can add to or define a diagnosis of a disease or susceptibility to a disease which results from under-expression, over-expression or altered expression of IGS4. Also in this event co-expression of relevant receptor activity modifying proteins can be required to obtain diagnostic assays of desired quality. Individuals carrying mutations in the IGS4 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled IGS4 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., Science (1985) 230:1242. Sequence changes at specific locations may also be revealed by nuclease protection assays, such as RNase and S1 protection or the chemical cleavage method. See Cotton et al., Proc. Natl. Acad. Sci. USA (1985) 85: 4397-4401. In another embodiment, an array of oligonucleotide probes comprising the IGS4 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610-613 (1996)).

The diagnostic assays offer a process for diagnosing or determining a susceptibility to PNS, psychiatric and CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; attention deficit/hyperactivity disorder (ADHD); cardiovascular diseases, including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders, including irritable bowel syndrome (IBS), inflammatory bowel disease (IBD), gastroesophagal reflux disease (GERD), motility disorders and conditions of delayed gastric emptying, such as post operative or diabetic gastroparesis, and diabetes, ulcers—e.g. gastric ulcer; diarrhoea; other diseases including osteoporosis; inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus; and gynaecological disorders, through detection of mutation in the IGS4 gene by the methods described. According to the present invention, the diagnostic assays offer in particular a process for diagnosing or determining a susceptibility to disorders of the nervous system, including the central nervous system (CNS) and the peripheral nervous system (PNS), disorders of the gastrointestinal system and/or of the cardiovascular system and/or of skeletal muscle and/or of the thyroid, and/or also to lung diseases, immunological diseases and disorders of the genitourinary system.

In addition, PNS, psychiatric and CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; attention deficit/hyperactivity disorder (ADHD); cardiovascular diseases, including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders, including irritable bowel syndrome (IBS), inflammatory bowel disease (IBD), gastroesophagal reflux disease (GERD), motility disorders and conditions of delayed gastric emptying, such as post operative or diabetic gastroparesis, and diabetes, ulcers—e.g. gastric ulcer; diarrhoea; other diseases including osteoporosis; inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus; and gynaecological disorders, can be diagnosed by methods comprising determining from a sample derived from a subject an abnormally decreased or increased level of the IGS4 polypeptide or IGS4 mRNA. In particular disorders of the nervous system, including the central nervous system (CNS) and the peripheral nervous system (PNS), disorders of the gastrointestinal system and/or of the cardiovascular system and/or of skeletal muscle and/or of the thyroid, and/or also lung diseases, immunological diseases and disorders of the genitourinary system can be diagnosed by methods comprising determining from a sample derived from a subject an abnormally decreased or increased level of the IGS4 polypeptide or IGS4 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an IGS4, in a sample derived from a host are well known to those of skill in the art. Such assay methods include radioimmunoassays, competitive-binding assays, Western Blot analysis and ELISA assays.

In another aspect, the present invention relates to a diagonostic kit for a disease or susceptibility to a disease, particularly PNS, psychiatric and CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; attention deficit/hyperactivity disorder (ADHD); cardiovascular diseases, including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders, including irritable bowel syndrome (IBS), inflammatory bowel disease (IBD), gastroesophagal reflux disease (GERD), motility disorders and conditions of delayed gastric emptying, such as post operative or diabetic gastroparesis, and diabetes, ulcers—e.g. gastric ulcer, diarrhoea; other diseases including osteoporosis; inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus; and gynaecological disorders, which comprises:

(a) an IGS4 polynucleotide, preferably the nucleotide sequence of SEQ ID NO: 1. SEQ ID NO: 3, SEQ ID NO: 5 or SEQ ID NO: 7, or a fragment thereof; and/or (b) a nucleotide sequence complementary to that of (a); and/or (c) an IGS4 polypeptide, preferably the polypeptide of SEQ ID NO: 2, SEQ ID NO: 4, SEQ ID NO: 6 or of SEQ ID NO: 8, or a fragment thereof; and/or (d) an antibody to an IGS4 polypeptide, preferably to the polypeptide of SEQ ID NO: 2, SEQ ID NO: 4, SEQ ID NO: 6 or of SEQ ID NO: 8; and/or (e) a RAMP polypeptide required for the relevant biological or antigenic properties of an IGS4 polypeptide It will be appreciated that in any such kit, (a), (b), (c) (d) or (e) may comprise a substantial component. Preferably the present invention relates to a diagnostic kit for diagnosing or determining a disease or a susceptibility to a disease of the nervous system, including the central nervous system (CNS) and the peripheral nervous system (PNS), a disease of the gastrointestinal system and/or of the cardiovascular system and/or of skeletal muscle and/or of the thyroid, and/or also lung diseases, immunological diseases and disorders of the genitourinary system.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them if required together with relevant RAMP's, may also be used as immunogens to produce antibodies immunospecific for the IGS4 polypeptides. The term "immunospecific" means that the antibodies have substantiall greater affinity for the polypeptides of the invention than their affinity for other related polypeptides in the prior art.

Antibodies generated against the IGS4 polypeptides may be obtained by administering the polypeptides or epitope-bearing fragments, analogs or cells to an animal, preferably a nonhuman, using routine protocols. For preparation of monoclonal antibodies, any technique, which provides antibodies produced by continuous cell line cultures, may be used. Examples include the hybridoma technique (Kohler, G. and Milstein, C., Naure (1975) 256:495-497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77-96, Alan R. Liss, Inc., 1985).

The above-described antibodies may be employed to isolate or to identify clones expressing the polypeptide or to purify the polypeptides by affinity chromatography.

Antibodies against IGS4 polypeptides as such, or against IGS4 polypeptide-RAMP complexes, may also be employed to treat PNS, psychiatric and CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; attention deficit/hyperactivity disorder (ADHD); cardiovascular diseases, including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders, including irritable bowel syndrome (IBS), inflammatory bowel disease (IBD), gastroesophagal reflux disease (GERD), motility disorders and conditions of delayed gastric emptying, such as post operative or diabetic gastroparesis, and diabetes, ulcers—e.g. gastric ulcer; diarrhoea; other diseases including osteoporosis; inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus; and gynaecological disorders, among others. Preferably the antibodies of the present invention may be used to treat disorders of the nervous system, including the central nervous system (CNS) and the peripheral nervous system (PNS), disorders of the gastrointestinal system and/or of the cardiovascular system and/or of skeletal muscle and/or of the thyroid, and/or also to treat lung diseases, immunological diseases and disorders of the genitourinary system.

Animals

Another aspect of the invention relates to non-human animal-based systems which act as models for disorders arising from aberrant expression or activity of IGS4. Non-human animal-based model systems may also be used to further characterize the activity of the IGS4 gene. Such systems may be utilized as part of screening strategies designed to identify compounds which are capable to treat IGS4 based disorders such as PNS, psychiatric and CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; attention deficit/hyperactivity disorder (ADHD); cardiovascular diseases, including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders, including irritable bowel syndrome (IBS), inflammatory bowel disease (IBD), gastroesophagal reflux disease (GERD), motility disorders and conditions of delayed gastric emptying, such as post operative or diabetic gastroparesis, and diabetes, ulcers—e.g. gastric ulcer; diarrhoea; other diseases including osteoporosis; inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus; and gynaecological disorders. In particular, the systems may be utilized as part of screening strategies designed to identify compounds which are capable in particular to treat IGS4 based disorders of the nervous system, including the central nervous system (CNS) and the peripheral nervous system (PNS), disorders of the gastrointestinal system and/or of the cardiovascular system and/or of skeletal muscle and/or of the thyroid, and/or also to treat lung diseases, immunological diseases and disorders of the genitourinary system. In this way the animal-based models may be used to identify pharmaceutical compounds, therapies and interventions which may be effective in treating disorders of aberrant expression or activity of IGS4. In addition such animal models may be used to determine the $LD_{50}$ and the $ED_{50}$ in animal subjects. These data may be used to determine the in vivo efficacy of potential IGS4 disorder treatments.

Animal-based model systems of IGS4 based disorders, based on aberrant IGS4 expression or activity, may include both non-recombinant animals as well as recombinantly engineered transgenic animals.

Animal models for IGS4 disorders may include, for example, genetic models. Animal models exhibiting IGS4 based disorder-like symptoms may be engineered by utilizing, for example, IGS4 sequences such as those described, above, in conjunction with techniques for producing transgenic animals that are well known to persons skilled in the art. For example, IGS4 sequences may be introduced into, and overexpressed and/or misexpressed in, the genome of the animal of interest, or, if endogenous IGS4 sequences are present, they may either be overexpressed, misexpressed, or, alternatively, may be disrupted in order to underexpress or inactivate IGS4 gene expression.

In order to overexpress or misexpress a IGS4 gene sequence, the coding portion of the IGS4 gene sequence may be ligated to a regulatory sequence which is capable of driving high level gene expression or expression in a cell type in which the gene is not normally expressed in the animal type of interest. Such regulatory regions will be well known to those skilled in the art, and may be utilized in the absence of undue experimentation.

For underexpression of an endogenous IGS4 gene sequence, such a sequence may be isolated and engineered such that when reintroduced into the genome of the animal of interest, the endogenous IGS4 gene alleles will be inactivated, or "knocked-out". Preferably, the engineered IGS4 gene sequence is introduced via gene targeting such that the endogenous IGS4 sequence is disrupted upon integration of the engineered IGS4 gene sequence into the animal's genome. Gene targeting is discussed, below, in this section.

Animals of any species, including, but not limited to, mice, rats, rabbits, squirrels, guinea-pigs, pigs, micro-pigs, goats, and non-human primates, e.g., baboons, monkeys, and chimpanzees may be used to generate animal models of IGS4 related disorders.

Any technique known in the art may be used to introduce a IGS4 transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (van der Putten et al., Proc. Natl. Acad. Sci., USA 82:6148-6152, 1985); gene targeting in embryonic stem cells (Thompson et al., Cell 56:313-321, 1989,); electroporation of embryos (Lo, Mol. Cell. Biol. 3:1803-1B14, 1983); and sperm-mediated gene transfer (Lavitrano et al., Cell 57:717-723, 1989); etc. For a review of such techniques, see Gordon, Transgenic Animals, Intl. Rev. Cytol. 115:171-229, 1989, which is incorporated by reference herein in its entirety.

The present invention provides for transgenic animals that carry the IGS4 transgene in all their cells, as well as animals which carry the transgene in some, but not all their cells, i.e., mosaic animals. (See, for example, techniques described by Jakobovits, Curr. Biol. 4:761-763, 1994) The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., Proc. Natl. Acad. Sci. USA 89:6232-6236, 1992).

The regulatory sequences required for such a cell-type specific activation will depend upon the particular cell type of interest, and will be apparent to those of skill in the art.

When it is desired that the IGS4 transgene be integrated into the chromosomal site of the endogenous IGS4 gene, gene targeting is preferred. Briefly, when such a technique is to be utilized, vectors containing some nucleotide sequences homologous to the endogenous IGS4 gene of interest (e.g., nucleotide sequences of the mouse IGS4 gene) are designed for the purpose of integrating, via homologous recombination with chromosomal sequences, into and disrupting the function of, the nucleotide sequence of the endogenous IGS4 gene or gene allele. The transgene may also be selectively introduced into a particular cell type, thus inactivating the endogenous gene of interest in only that cell type, by following, for example, the teaching of Gu et al. (Gu, H. et al., Science 265:103-106, 1994). The regulatory sequences required for such a cell-type specific inactivation will depend upon the particular cell type of interest, and will be apparent to those of skill in the art.

Once transgenic animals have been generated, the expression of the recombinant IGS4 gene and protein may be assayed utilizing standard techniques. Initial screening may be accomplished by Southern blot analysis or PCR techniques to analyze animal tissues to assay whether integration of the transgene has taken place. The level of mRNA expression of the IGS4 transgene in the tissues of the transgenic animals may also be assessed using techniques which include but are not limited to Northern blot analysis of tissue samples obtained from the animal, in situ hybridization analysis, and RT-PCR. Samples of target gene-expressing tissue, may also be evaluated immunocytochemically using antibodies specific for the target gene transgene product of interest. The IGS4 transgenic animals that express IGS4 gene mRNA or IGS4 transgene peptide (detected immunocytochemically, using antibodies directed against target gene product epitopes) at easily detectable levels may then be further evaluated to identify those animals which display characteristic IGS4 based disorder symptoms.

Once IGS4 transgenic founder animals are produced (i.e., those animals which express IGS4 proteins in cells or tissues of interest, and which, preferably, exhibit symptoms of IGS4 based disorders), they may be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound IGS4 transgenics that express the IGS4 transgene of interest at higher levels because of the effects of additive expression of each IGS4 transgene; crossing of heterozygous transgenic animals to produce animals homozygous for a given integration site in order to both augment expression and eliminate the possible need for screening of animals by DNA analysis; crossing of separate homozygous lines to produce compound heterozygous or homozygous lines; breeding animals to different inbred genetic backgrounds so as to examine effects of modifying alleles on expression of the IGS4 transgene and the development of IGS4-like symptoms. One such approach is to cross the IGS4 transgenic founder animals with a wild type strain to produce an F1 generation that exhibits IGS4 related disorder-like symptoms, such as those described above. The F1 generation may then be inbred in order to develop a homozygous line, if it is found that homozygous target gene transgenic animals are viable.

Vaccines

Another aspect of the invention relates to a method for inducing an immunological response in a mammal which comprises administering to (for example by inoculation) the mammal the IGS4 polypeptide, or a fragment thereof, if required together with a RAMP polypeptide, adequate to produce antibody and/or T cell immune response to protect said animal from PNS, psychiatric and CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; attention deficit/hyperactivity disorder (ADHD); cardiovascular diseases, including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders, including irritable bowel syndrome (IBS), inflammatory bowel disease (IBD), gastroesophagal reflux disease (GERD), motility disorders and conditions of delayed gastric emptying, such as post operative or diabetic gastroparesis, and diabetes, ulcers—e.g. gastric ulcer; diarrhoea; other diseases including osteoporosis; inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus; and gynaecological disorders, among others. Yet another aspect of the invention relates to a method of inducing immunological response in a mammal which comprises delivering the IGS4 polypeptide via a vector directing expression of the IGS4 polynucleotide in vivo in order to induce such an immunological response to produce antibody to protect said animal from diseases. In particular the invention relates to a method for inducing an immunological response in a mammal which comprises inoculating the mammal with the IGS4 polypeptide, or a fragment thereof, if required together with a RAMP polypeptide, adequate to produce antibody and/or T cell immune response to protect said animal from disorders of the nervous system, including the central nervous system (CNS) and the peripheral nervous system (PNS), disorders of the gastrointestinal system and/or of the cardiovascular system and/or of skeletal muscle and/or of the thyroid, and/or also from lung diseases, immunological diseases and disorders of the genitourinary system.

A further aspect of the invention relates to an immunological/vaccine formulation (composition) which, when introduced into a mammalian host, induces an immunological response in that mammal to an IGS4 polypeptide wherein the composition comprises an IGS4 polypeptide or IGS4 gene. Such immunological/vaccine formulations (compositions) may be either therapeutic immunological/vaccine formulations or prophylactic immunological/vaccine formulations. The vaccine formulation may further comprise a suitable carrier. Since the IGS4 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The IGS4 polypeptide of the present invention may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics.

IGS4 polypeptides are responsible for biological functions, including pathologies. Accordingly, it is desirable to find compounds and drugs which stimulate IGS4 on the one hand and which can inhibit the function of IGS4 on the other hand. In general, agonists are employed for therapeutic and prophylactic purposes for such conditions as PNS, psychiatric and CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; attention deficit/hyperactivity disorder (ADHD); cardiovascular diseases, including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders, including irritable bowel syndrome (IBS), inflammatory bowel disease (IBD), gastroesophagal reflux disease (GERD), motility disorders and conditions of delayed gastric emptying, such as post operative or diabetic gastroparesis, and diabetes, ulcers—e.g. gastric ulcer; diarrhoea; other diseases including osteoporosis; inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus; and gynaecological disorders. Antagonists may be employed for a variety of therapeutic and prophylactic purposes for such conditions as PNS, psychiatric and CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; attention deficit/hyperactivity disorder (ADHD); cardiovascular diseases, including heart failure, angina pectoris, arrhythmias, myocardial infarction, cardiac hypertrophy, hypotension, hypertension—e.g. essential hypertension, renal hypertension, or pulmonary hypertension, thrombosis, arteriosclerosis, cerebral vasospasm, subarachnoid hemorrhage, cerebral ischemia, cerebral infarction, peripheral vascular disease, Raynaud's disease, kidney disease—e.g. renal failure; dyslipidemias; obesity; emesis; gastrointestinal disorders, including irritable bowel syndrome (IBS), inflammatory bowel disease (IBD), gastroesophagal reflux disease (GERD), motility disorders and conditions of delayed gastric emptying, such as post operative or diabetic gastroparesis, and diabetes, ulcers—e.g. gastric ulcer, diarrhoea; other diseases including osteoporosis; inflammations; infections such as bacterial, fungal, protozoan and viral infections, particularly infections caused by HIV-1 or HIV-2; pain; cancers; chemotherapy induced injury; tumor invasion; immune disorders; urinary retention; asthma; allergies; arthritis; benign prostatic hypertrophy; endotoxin shock; sepsis; complication of diabetes mellitus; and gynaecological disorders. Particularly, the present invention may be employed in a screening process for compounds which bind the receptor and which activate (agonists) or inhibit activation of (antagonists) the IGS4 neuromedin receptor protein, preferably the mammalian IGS4 neuromedin receptor protein, said protein exhibiting high affinity binding for neuromedin U, preferably for neuromedin U-8, for neuromedin U-23 and/or for neuromedin U-25. These screening assays are particularly suitable for screening compounds which are effective with regard to disorders of the nervous system, including the central nervous system (CNS) and the peripheral nervous system (PNS), disorders of the gastrointestinal system and/or of the cardiovascular system and/or of skeletal muscle and/or of the thyroid, and/or also to lung diseases, immunological diseases and disorders of the genitourinary system.

In general, such screening procedures involve producing appropriate cells, which express the receptor polypeptide of the present invention on the surface thereof and, if essential co-expression of RAMP's at the surface thereof. Such cells include cells from mammals, yeast, *Drosophila* or *E. coli*. Cells expressing the receptor (or cell membrane containing the expressed receptor) are then contacted with a test compound to observe binding, or stimulation or inhibition of a functional response.

One screening technique includes the use of cells which express the receptor of this invention (for example, transfected CHO cells) in a system which measures extracellular pH, intracellular pH, or intracellular calcium changes caused by receptor activation. In this technique, compounds may be contacted with cells expressing the receptor polypeptide of the present invention. A second messenger response, e.g., signal transduction, pH changes, or changes in calcium level, is then measured to determine whether the potential compound activates or inhibits the receptor.

Another method involves screening for receptor inhibitors by determining modulation of a receptor-mediated signal, such as cAMP accumulation and/or adenylate cyclase activity. Such a method involves transfecting an eukaryotic cell with the receptor of this invention to express the receptor on the cell surface. The cell is then exposed to an agonist to the receptor of this invention in the presence of a potential antagonist. If the potential antagonist binds the receptor, and thus inhibits receptor binding, the agonist-mediated signal will be modulated.

Another method for detecting agonists or antagonists for the receptor of the present invention is the yeast-based technology as described in U.S. Pat. No. 5,482,835, incorporated by reference herein.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed.

Thus candidate compounds may be screened which show ligand binding to the IGS4 receptors of the present invention. In the context of the present invention the term "ligand binding" is understood as to describe compounds with affinity to the IGS4 receptors showing log $EC_{50}$ values of at least below −6.00 (approx. 660 nM), preferably log $EC_{50}$ below −7.00 (approx. 55 nM), more preferably log $EC_{50}$ below −9.00 (approx. 500 pM to 1.2 nM), and most preferably log $EC_{50}$ below −10.00 (approx. 50-100 pM).

Thus in one aspect the invention concerns a method of determining whether a substance is a potential ligand of IGS4 receptor comprising (a) contacting cells expressing one of the IGS4 neuromedin receptors defined supra or one of the receptors of SEQ ID NO:2, SEQ ID NO:4, SEQ ID NO:6 and SEQ ID NO:8, or contacting a receptor membrane preparation comprising one of said IGS4 neuromedin receptors defined supra or one of the receptors of SEQ ID NO:2, SEQ ID NO:4, SEQ ID NO:6 and SEQ ID NO:8 with labeled neuromedin U in the presence and in the absence of the substance; and (b) measuring the binding of neuromedin U to IGS4.

Further, the assays may simply comprise the steps of mixing a candidate compound with a solution containing an IGS4 polypeptide to form a mixture, measuring the IGS4 activity in the mixture, and comparing the IGS4 activity of the mixture to a standard.

The IGS4 cDNA, protein and antibodies to the protein may also be used to configure assays for detecting the effect of added compounds on the production of IGS4 mRNA and protein in cells. For example, an ELISA may be constructed for measuring secreted or cell associated levels of IGS4 protein using monoclonal and polyclonal antibodies by standard methods known in the art, and this can be used to discover agents which may inhibit or enhance the production of IGS4 (also called antagonist or agonist, respectively) from suitably manipulated cells or tissues. Standard methods for conducting screening assays are well known in the art.

Examples of potential IGS4 antagonists include antibodies or, in some cases, oligonucleotides or proteins which are closely related to the ligand of the IGS4, e.g., a fragment of the ligand, or small molecules which bind to the receptor but do not elicit a response, so that the activity of the receptor is prevented.

Thus in another aspect, the present invention relates to a screening kit for identifying agonists, antagonists, ligands, receptors, substrates, enzymes, etc. for IGS4 polypeptides; or compounds which decrease, increase and/or otherwise enhance the production of IGS4 polypeptides, which comprises:

(a) an IGS4 polypeptide, preferably that of SEQ ID NO: 2, SEQ ID NO: 4, SEQ ID NO: 6 or SEQ ID NO: 8;

(b) a recombinant cell expressing an IGS4 polypeptide, preferably that of SEQ ID NO: 2, SEQ ID NO: 4, SEQ ID NO: 6 or SEQ ID NO: 8;

(c) a cell membrane expressing an IGS4 polypeptide; preferably that of SEQ ID NO: 2, SEQ ID NO: 4, SEQ ID NO: 6 or SEQ ID NO: 8; or (d) antibody to an IGS4 polypeptide, preferably that of SEQ ID NO: 2, SEQ ID NO: 4, SEQ ID NO: 6 or SEQ ID NO: 8.

It will be appreciated that in any such kit, (a), (b), (c) or (d) may comprise a substantial component.

Prophylactic and Therapeutic Methods

This invention provides methods of treating abnormal conditions related to both an excess of and insufficient amounts of IGS4 activity.

If the activity of IGS4 is in excess, several approaches are available. One approach comprises administering to a subject an inhibitor compound (antagonist) as hereinabove described along with a pharmaceutically acceptable carrier in an amount effective to inhibit activation by blocking binding of ligands to the IGS4, or by inhibiting interaction with a RAMP polypeptide or a second signal, and thereby alleviating the abnormal condition.

In another approach, soluble forms of IGS4 polypeptides still capable of binding the ligand in competition with endogenous IGS4 may be administered. Typical embodiments of such competitors comprise fragments of the IGS4 polypeptide.

In still another approach, expression of the gene encoding endogenous IGS4 can be inhibited using expression-blocking techniques. Known such techniques involve the use of antisense sequences, either internally generated or separately administered. See, for example, O'Connor, J Neurochem (1991) 56:560 in Oligodeoxynucleotides as Antisense Inhibitors of Gene Expression, CRC Press, Boca Raton, Fla. USA (1988). Alternatively, oligonucleotides, which form triple helices with the gene, can be supplied. See, for example, Lee et al., Nucleic Acids Res (1979) 6:3073; Cooney et al., Science (1988) 241:456; Dervan et al, Science (1991) 251:1360. These oligomers can be administered per se or the relevant oligomers can be expressed in vivo. Synthetic antisense or triplex oligonucleotides may comprise modified bases or modified backbones. Examples of the latter include methylphosphonate, phosphorothioate or peptide nucleic acid backbones. Such backbones are incorporated in the antisense or triplex oligonucleotide in order to provide protection from degradation by nucleases and are well known in the art. Antisense and triplex molecules synthesized with these or other modified backbones also form part of the present invention.

In addition, expression of the IGS1 polypeptide may be prevented by using ribozymes specific to the IGS1 mRNA sequence. Ribozymes are catalytically active RNAs that can be natural or synthetic (see for example Usman, N, et al., Curr. Opin. Struct. Biol (1996) 6(4), 527-33.) Synthetic ribozymes can be designed to specifically cleave IGS1 mRNAs at selected positions thereby preventing translation of the IGS1 mRNAs into functional polypeptide. Ribozymes may be synthesized with a natural ribose phosphate backbone and natural bases, as normally found in RNA molecules. Alternatively the ribosymes may be synthesized with non-natural backbones to provide protection from ribonuclease degradation, for example, 2'-O-methyl RNA, and may contain modified bases.

For treating abnormal conditions related to an under-expression of IGS4 and its activity, several approaches are also available. One approach comprises administering to a subject a therapeutically effective amount of a compound which activates IGS4, i.e., an agonist as described above, in combination with a pharmaceutically acceptable carrier, to thereby alleviate the abnormal condition. Alternatively, gene therapy may be employed to effect the endogenous production of IGS4 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, Gene Therapy and other Molecular Genetic-based Therapeutic Approaches, (and references cited therein) in Human Molecular Genetics, Strachan T. and Read A. P., BIOS Scientific Publishers Ltd (1996).

Any of the therapeutic methods described above may be applied to any subject in need of such therapy, including, for example, mammals such as dogs, cats, cows, horses, rabbits, monkeys, and most preferably, humans.

Formulation and Administration

Peptides, such as the soluble form of IGS4 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible.

The dosage range required depends on the choice of peptide or compound, the route of administration, the nature of the formulation, the nature of the subject's condition, and the judgment of the attending practitioner. Suitable dosages are in the range of 0.1-100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

The following examples are only intended to further illustrate the invention in more detail, and therefore these examples are not deemed to restrict the scope of the invention in any way.

EXAMPLE 1

The Cloning of cDNA Encoding a Novel G Protein-Coupled Receptor

EXAMPLE 1a

Homology PCR cloning of a Genomic Fragment Encoding a Novel G-protein Coupled Receptor (GPCR)

A PCR based homology cloning strategy was used to isolate partial genomic DNA sequences encoding novel G-protein coupled receptors. Forward (F22) and reverse (R44 and R46) degenerate PCR primers were designed in conserved areas of the neurotensin receptor gene family (Vita N. et al. [1993] Febs Lett. 317, 139-142; Vita N. et al. [1998] Eur. J. Pharmacol. 360, 265-272) within transmembrane domains 1 (TM1) and 3 (TM3) and at the boundary between TM3 and intracellular loop 2 (I2):

```
F22 (TM1):
5'-CTCATCTTCGCGGTGGGC(A or            (SEQ ID NO: 13)
G)C(A,C,G or T)G(C or T)(A,C,G or
T)GG-3'

R44 (TM3/I2):
5'-GGCCAGGCAGCGCTCCGCGCT(C or         (SEQ ID NO: 14)
Inosine)A(A or G)(A,C,G or T)C(C
or T)(A,C,G or T)GC(A,G or T)-3'

R46 (TM3):
5'-GAA(A or G)TA(A or G)TAGCC(A or    (SEQ ID NO: 15)
G)CG(A or G)CAGCC(A or T)-3'
```

In order to suppress amplification of known members of the neurotensin receptor family, the 3' ultimate nucleotide position of primer R44 was chosen in such a way that is was not complementary to the corresponding position of both NTR1 and NTR2 cDNA. The primary PCR reaction was carried out in a 60 μl volume and contained 100 ng human genomic DNA (Clontech), 6 μl GeneAmp™ 10×PCR buffer II (100 mM Tris-HCl pH 8.3; 500 mM KCl, Perkin Elmer), 3.6 μl 25 mM MgCl$_2$, 0.36 μl dNTPs (25 mM of each dNTP), 1.5 units AmpliTaq-Gold™ polymerase (Perkin Elmer) and 30 pmoles of each of the degenerated forward (F22) and reverse primer (R44). Reaction tubes were heated at 95° C. for 10 min and then subjected to 35 cycles of denaturation (95° C., 1 min), annealing (55° C., 2 min) and extension (72° C., 3 min). Finally reaction tubes were heated for 10 min at 72° C.

For the semi-nested PCR reaction 1 μl of a 1/50 dilution of the primary PCR reaction was used as a template using the degenerate forward and reverse primers F22 and R46 respectively. The semi-nested PCR reaction was carried out under the same conditions as the primary PCR reaction.

Semi-nested PCR reaction products were size fractionated on an agarose gel and stained with ethidium bromide. Although a fragment of ±220 bp was expected, only a fragment of ±120 bp was visible. This fragment was purified from gel using the Qiaex-II™ purification kit (Qiagen) and ligated into the pGEM-T plasmid according to the procedure recommended by the supplier (pGEM-T kit, Promega). The recombinant plasmids thus produced were used to transform competent E. coli SURE™ 2 bacteria (Stratagene). Transformed cells were plated on LB agar plates containing ampicillin (100 μg/ml), IPTG (0.5 mM) and X-gal (50 μg/ml). Plasmid DNA was purified from mini-cultures of individual colonies using a Qiagen-tip 20 miniprep kit (Qiagen). DNA sequencing reactions were carried out on the purified plasmid DNA with the ABI Prism™ BigDye™ Terminator Cycle Sequencing Ready Reaction kit (PE-ABI), using insert-flanking primers.

TABLE 7

Overview of oligo primers used.

SEQ ID NO: 13  F22:
5'-CTCATCTTCGCGGTGGGC(A or G)C(A,C,G or T)G(C or T)(A,C,G or T)GG-3'

SEQ ID NO: 14  R44:
5'-GGCCAGGCAGCGCTCCGCGCT(C or Inosine)A(A or G)(A,C,G or T)C(C or T)(A,C,G or T)GC(A,G or T)-3'

SEQ ID NO: 15  R46:
5'-GAA(A or G)TA(A or G)TAGCC(A or G)CG(A or G)CAGCC(A or T)-3'

SEQ ID NO: 16  AP1:
5'-CCATCCTAATACGACTCACTATAGGGC-3'

SEQ ID NO: 17  AP2:
5'-ACTCACTATAGGGCTCGAGCGGC-3'

SEQ ID NO: 18  IGS4R1:
5'GGATCCCAAATAAGAAAGGGTAGTTGC-3'

SEQ ID NO: 19  1GS4R2:
5'AAAGGGTAGTTGCGCCACATCTCATAGAC-3'

SEQ ID NO: 20  IGS4F5:
5'AGGTCTATGAGATGTGGCGCAACTACCCT-3'

SEQ ID NO: 21  IGS4F6:
5'ATGTGGCGCAACTACCCTTTCTTATTTGGG-3'

SEQ ID NO: 22  R74:
5'-CGGAAGTTGGCGGACACG(A or G)(A,C or G)(A or G)TT(A or G)TA-3'

SEQ ID NO: 23  IGS4F7:
5'-GCTCAGCTTGAAACAGAGCCTCGTACC-3'

SEQ ID NO: 24  IGS4F8:
5'-CCATGTGGATCTACAATTTCATCATCC-3'

SEQ ID NO: 25  IGS4F9:
5'-AAGACAAATCTCTTGAGGCAGATGAAGGG-3'

SEQ ID NO: 26  IGS4F10:
5'-GATGCTGTTTGTCTTGGTCTTAGTGTTTGC-3'

SEQ ID NO: 27  IGS4R5:
5'-GGATGATGAAATTGTAGATCCACATGGGC-3'

SEQ ID NO: 28  IGS4R6:
5'-TGTGGAGAAGTCTCTCAAAGTGTGG-3'

SEQ ID NO: 29  IGS4R7:
5'-TAGTAGGAGTGACAGCCTGACTCGGAACG-3'

SEQ ID NO: 30  IGS4R8:
5'-AACGTAGATGACTCAGGACGAACCATTTCC-3'

SEQ ID NO: 31  IGS4F11:
5'-TCGTACCAGGGGAGGCTCAGGC-3'

Sequencing reaction products were purified via EtOH/NaOAc precipitation and analyzed on an ABI 377 automated sequencer.

Sequence analysis of the insert of clone HNT1552 showed that it potentially encoded part of a novel member of the GPCR family. We refer to this novel GPCR sequence as IGS4.

EXAMPLE 1b

Cloning of cDNA Fragments Containing the Complete IGS4 Coding Sequence

The complete coding sequence of IGS4 cDNA was obtained via both RACE analysis (rapid amplification of cDNA ends) and RT-PCR amplification. 5'- and 3' RACE PCR reactions were performed on Marathon-Ready™ cDNA from human brain or testis (Clontech n° 7400-1 and 7414-1 respectively), using the adaptor primers 1 and 2 (AP1: SEQ ID NO: 16; AP2: SEQ ID NO: 17) provided with the Marathon™ cDNA amplification kit (Clontech K1802-1) and IGS4 specific primers. PCR RACE reactions were performed according to the instructions of the Marathon-Ready™ cDNA user manual provided by Clontech. RACE products were separated on agarose gel, visualized with ethidium bromide and blotted onto Hybond N⁺ membranes. Blots were prehybridized at 65° C. for 2 h in modified Church buffer (0.5M phosphate, 7% SDS, 10 mM EDTA) and then hybridised overnight at 65° C. in the same buffer containing $2 \times 10^6$ cpm/ml of a $^{32}$P-labelled IGS4 cDNA probe. IGS4 cDNA probes were radiolabelled via random primed incorporation of [α-$^{32}$P]dCTP to a specific activity of >$10^9$ cpm/µg using the Prime-It II kit™ (Stratagene) according to the instructions provided by the supplier. Hybridized blots were washed at high stringency (2×30 min at room temperature in 2×SSC/0.1% SDS, followed by 2 washes of 40 min at 65° C. in 0.1×SSC, 0.1% SDS) and autoradiographed overnight. Hybridizing fragments were purified from a preparative gel, cloned into the PGEM-T vector and sequenced as described above.

An initial round of semi-nested 5' RACE analysis on human brain cDNA using the IGS4 specific primers IGS4R1 (SEQ ID NO: 18) and IGS4R2 (SEQ ID NO: 19)(designed on the DNA sequence of clone HNT1552) yielded clones HNT1886 and HNT1887 (FIG. 1). These clones extended the IGS4 cDNA sequence upstream up to and beyond the putative start of translation codon. Likewise an initial round of 3' RACE analysis on human brain cDNA using IGS4 specific primers IGS4F5 (SEQ ID NO: 20) and IGS4F6 (SEQ ID NO: 21) yielded clones HNT1874-1878 and HNT1902-1903 (FIG. 1). These clones extended the known IGS4 cDNA at the 3' end.

All sequences obtained at this point were assembled into a single contig which contained a long open reading frame, encoding part of a novel protein that was most similar to human orphan receptor FM-3 (Tan et al., Genomics 52, 223-229 [1998], GenBank accession n° AF044600 and AF044601). To investigate the RNA expression profile of IGS4, a Master Blot™ membrane (Clontech cat n° 7770-1) containing RNA from different human tissues was hybridized to the $^{32}$P-labelled insert of clone HNT1903 under the conditions recommended by the supplier. The strongest hybridization was obtained with testis RNA whereas much weaker signals were obtained in prostate, stomach, spinal cord, hippocampus, medulla oblongata, thyroid gland, thymus, lung and trachea.

Since the contig sequence did not yet contain the complete IGS4 coding sequence we set up an RT-PCR homology cloning experiment on human total brain RNA using IGS4 specific primer IGS4F6 (SEQ ID NO: 21) and a degenerated primer (R74, SEQ ID NO: 22), which was designed in a conserved area (at the TM7/C-terminal intracellular part) of the GPCR subfamily composed of the neurotensin receptors 1 and 2, the growth hormone secretagogue receptor (Howard A. D. et al. [1996] Science 273, 974-977) and the orphan GPCR FM-3 and GPR38 (McKee K. K. et al. [1997] Genomics 46, 426-434). RT-PCR reactions were carried out in a 50 µl volume on 500 ng total RNA from human brain using the Titan™ One Tube RT-PCR System (Boehringer catalogue n° 1,888,382) according to the recommendations of the supplier. Briefly, RT-PCR conditions were as follows: reverse transcription for 45 min at 55° C.; 2 min denaturation at 94° C., followed by a touch-down PCR reaction of 20 cycles (30 sec denaturation at 94° C., 30 sec annealing at 60° C. [−0.25° C./cycle] and 2 min extension at 68° C.) and an additional round of 30 PCR cycles (30 sec denaturation at 94° C., 30 sec annealing at 55° C. and 3 min [+5 sec/cycle] extension at 68° C.). This was concluded with an extra extension step of 7 min at 68° C. Reaction products were analyzed via Southern blotting using the radiolabelled insert of clone HNT1903. A fragment of ±690 bp that hybridized to the probe was purified from the gel (QiaexII™, Qiagen) and cloned into the pGEM-T vector yielding clones HNT2210-2212. Sequence analysis of these clones allowed to extend the existing IGS4 cDNA contig in the 3' direction.

Since the extended IGS4 cDNA contig still did not yet contain a translational stop codon, additional IGS4 specific 3' RACE primers were designed (IGS4F7-10, SEQ ID NO: 23-26)). Nested or semi-nested 3' RACE reactions were carried out on Marathon Ready™ cDNA from human testis (Clontech 7414-1). IGS4 specific bands (as assessed via Southern blot analysis using an IGS4 specific probe) were cloned into pGEM-T. This yielded clones HNT2289-90 (AP1/IGS4F5->AP2/IGS4F9), HNT2293-2295 (AP1/IGS4F6->AP2/IGS4F9), HNT2296-2297 (AP1/IGS4F7->AP2/IGS4F9), HNT2308-2310 (AP1/IGS4F8->AP2/IGS4F10) HNT2253 (AP1/IGS4F7->AP1/IGS4F5). An additional 5' RACE PCR reaction carried out on testis Marathon Ready™ cDNA yielded clones HNT2279-2281 (AP2/IGS4R6->AP2/IGS4R5). (note: AP1/IGS4F5->AP2/IGS4F9 e.g. indicates that clones were generated from an IGS4 specific fragment obtained after the primary RACE PCR reaction [using primer pair AP1/IGS4F5] was nested with primer pair AP2/IGS4F9).

Sequence analysis of these clones allowed to extend the existing IGS4 cDNA contig further in the 3' direction although the end of the IGS4 coding sequence was not yet been reached. A computer-assisted homology search (Blastn; Altschul S. F. et al., Nucleic Acids Res. (1997) 25:3389-3402) of the IGS4 contig DNA sequence against the expressed sequence tag (EST) database (dbest) showed the presence of an EST sequence (accession n° N45474) which overlapped with the 3' end of the IGS4 contig (near 100% identity in the overlap area). EST N45474 further extended the IGS4 DNA contig at the 3' end into a translational stop codon and into the 3' untranslated region (3'-UTR). In addition another set of ESTs was identified which all covered the 3'-UTR of the IGS4 mRNA (FIG. 2). Additional IGS4 specific primers (IGS4R7-8, SEQ ID NO: 29-30)) were designed within the 3'-UTR of these ESTs. Primary PCR reactions were carried out on Marathon Ready™ cDNA from human testis using various combinations of the IGS4F7 (SEQ ID NO: 23). IGS4F11 (SEQ ID NO: 31) and IGS4R7-8 (SEQ ID NO: 29-30) primers. PCR tubes were heated for 2 min at 95° C. and then subjected to 35 cycles of denaturation (95° C., 30 sec), annealing (65° C., 30 sec) and extension (72° C., 1 min 30 sec). Finally the reactions tubes were heated at 72° C. for 10 min. Nested PCR reactions were also carried out under the same conditions. DNA fragments of ±1630 bp were purified from gel and cloned into the pGEM-T vector. The following clones were obtained: HNT2311, HNT2312 and HNT2317 (IGS4F7/IGS4R7->IGS4F11/IGS4R8); HNT2313, HNT2324, HNT2326 and HNT2328 (IGS4F11->IGS4R8); HNT2314, HNT2315 and HNT2322 (IGS4F11->R7). Clone HNT2363 was obtained from a purified 1630 bp PCR fragment, that was amplified from human testis Marathon Ready™ cDNA using the IGS4F11/R7 primer pair under the following slightly modified conditions. After an initial denaturation of 2 min at 94° C., PCR tubes were subjected to 15 cycles of denaturation [15 sec, 94° C.], annealing [30 sec, 65° C.] and extension [2 min, 72° C.] followed by another 20 cycles of denaturation [15 sec, 94° C.], annealing [30 sec, 65° C.] and extension [2 min, 72° C.; +10 sec/cycle]. There was a final extension step of 7 min at 72° C. Sequence analysis of these clones allowed to assemble an IGS4 cDNA consensus sequence (FIG. 1). Close inspection of all clones showed that they actually were of 2 sequence types, which differed at 5 nucleotide positions. These variant sequences correspond to a polymorphism within the human population. We refer to these different cDNA types as IGS4ADNA (SEQ ID NO: 1 and SEQ ID NO: 3) and IGS4BDNA (SEQ ID NO: 5 and SEQ ID NO: 7). The consensus sequence contained a long open reading frame that contained two in-frame start codons (positions 55-57 (SEQ ID NO: 1 and SEQ ID NO: 5) and 64-66 (SEQ ID NO: 3 and SEQ ID NO: 7) in IGS4ADNA and IGS4BDNA), predicting a protein of either 415 (SEQ ID NO: 2 and SEQ ID NO: 6) or 412 (SEQ ID NO: 4 and SEQ ID NO: 8) amino acids, which showed good homology to GPCR proteins. Hydropathy analysis (Kyte J. et al. [1982] J. Mol. Biol. 157: 105-132; Klein P. et al. [1985] Biochim. Biophys. Acta 815:468-476) of the protein also indicated the presence of 7 transmembrane domains. Since the first ATG initiator codon is within a weak "Kozak" translation initiation context and the second one is in a strong Kozak context, it is likely that the IGS4A/B protein starts at the second methionine and is 412 amino acids long (Kozak M. [1999] Gene 234, 187-208). However some (or even exlusive) initiation at the first ATG cannot be excluded. Among the five polymorphic nucleotides, four (positions 947, 999, 1202 and 1216 in IGS4A/BDNA) resulted in a switch in the encoded amino acid residue, whereas the fifth (pos 1381 in IGS4A/BDNA) was within the 3'-UTR. The respective predicted protein sequences are referred to as IGS4APROT (SEQ ID NO: 2 and SEQ ID NO: 4) and IGS4BPROT (SEQ ID NO: 6 and SEQ ID NO: 8). (note 1: the sequence of IGS4APROT and IGS4BPROT in this document is represented as the longest possible (415 amino acids) sequence but it is understood that the actual protein might be 3 amino acids shorter at the amino-terminus; for this reason the first 3 amino acids of IGS4APROT and IGS4BPROT in Table 4 and 5 have been bracketed) (note 2: In this document IGS4 refers to the IGS4 sequence in general, irrespective of the particular allelic type). Homology searches of the IGS4 protein sequence against public domain protein databanks showed best homology to the human orphan GPCR FM-3 (accession n° 043664, Tan C. P., et al. Genomics (1998) 52: 223-229; 46% identity in IGS4A amino acid residues 26-342).

Homology searches of DNA databanks with the IGS4 cDNA sequence yielded a number of entries which were also derived from the IGS4 gene locus (FIG. 2 for overview):

10 EST sequence entries (accession nrs W61169, A1432384, W61131, A1023570, F01358, F03770, Z38158, R40869, R37725, H11333), 2 STS (sequence tagged sites) (accession nrs G20615 and G05725) and one genomic sequence (accession nr AQ078563) were discovered which were all derived from the 3'-UTR of IGS4 cDNA EST accession n° N45474 encoded the 3' end of the IGS4 coding sequence and part of the 3' UTR (cfr supra).

A 'working draft' high throughput genomic sequence (accession nr AC008571, version AC008571.1, deposited 3 AUG 1999), which consisted of 42 unordered contigs assembled in an arbitrary order was discovered in which we detected the entire IGS4 cDNA sequence in 4 separate areas. These areas most likely correspond to the different IGS4 exons as they were flanked by canonical splice donor and acceptor sequences. On the basis of this analysis the position of the different exons in the IGS4ADNA (or IGS4BDNA) sequence can be defined as follows: exon 1 (1-780), exon 2 (781-865), exon 3 (866-991) and exon 4 (992-1658). The AC008571 genomic sequence is of the IGS4A allelic type.

6 overlapping EST entries (accession nrs H11359, R13890, R13353, F07531, F05108, F05107) were discovered of which the assembled DNA sequence overlapped at its 3' end with IGS4 exon 2 and the beginning of exon 3. However the DNA sequence upstream of exon 2 was completely different from IGS4 exon 1. Probably these six EST's are derived from transcripts which originated from an alternative promoter.

Finally 2 genomic sequence entries (accession nrs AQ019411 and AQ015065) were discovered which encoded exon 2.

Among the many IGS4 cDNA clones that we isolated in the different experiments described above, we also discovered a number of clones that contained a 64 bp deletion (pos 866-929 in IGS4ADNA) (besides a number of clones derived from unspliced [or partially spliced] transcripts). So far we only discovered truncated transcripts of the polymorphic type A. We refer to this splice variant cDNA sequence as IGS4A-64DNA (SEQ ID NO: 9 and SEQ ID NO: 11). Since this deletion occurs exactly at the exon 2/exon 3 boundary and since the last 2 nucleotides of the deleted fragment are "AG", it is likely that this deletion represents an alternative splicing event in which the "AG" within exon 3 served as a splice acceptor. The IGS4A reading frame encoded by the splice variant is frameshifted beyond the deletion point. The encoded (truncated) protein of 296 amino acids is referred to as IGS4A-64PROT (SEQ ID NO: 10 and SEQ ID NO: 12). Hydropathy analysis of the IGS4A-64PROT sequence shows that this protein only contains 5 transmembrane domains (corresponding to TM domains 1-5 of IGS4APROT). This truncated receptor might have physiological relevance.

The bacterial strain harboring plasmid HNT2322 (containing the IGS4ADNA insert) was recloned after replating on LB agar plates containing 100 µg ampicillin/ml and deposited both in the Innogenetics N.V. strain list (ICCG4320) and at the "Centraalbureau voor Schimmelculturen (CBS)" in Baarn, The Netherlands (accession n° CBS102221). Plasmid DNA was prepared from the recloned isolate and the insert was resequenced and found to be identical to the IGS4ADNA sequence.

The bacterial strain harboring plasmid HNT2363 (containing the IGS4BDNA insert) was recloned after replating on LB agar plates containing 100 µg ampicillin/ml and deposited both in the Innogenetics N.V. strain list (ICCG4340) and at the "Centraalbureau voor Schimmelculturen (CBS)" in Baarn, The Netherlands (accession n° CBS102222). Plasmid DNA was prepared from the recloned isolate and the insert was resequenced and found to be identical to the IGS4BDNA sequence.

EXAMPLE 2

Specific Changes in Intracellular Calcium Concentrations Induced in CHOGα16-IGS4 Cells by Neuromedin U.

EXAMPLE 2a

Experimental Procedures: Method and Materials.

A. Method and Materials for IGS-4 transfected CHOGα16-IGS4 cells.

The following materials were used in the experiments: Vector containing IGS4-DNA sequence (IGS4-pcDNA3.1); SuperFect Transfection Reagent (Qiagen); Nut-Mix F12 (Gibco) with 10% FCS, 0.028 mg/ml Gentamycin (Gibco); 0.22 mg/ml Hygromycin (Gibco).

Materials used for clone selection: Nut-Mix F12 with 10% FCS; 0.028 mg/ml Genatmycin; 0.22 mg/ml Hygromycin and 0.55 mg/ml Geneticin (Gibco).

The following method was applied: Transfection with SuperFect Transfection Reagent was carried out as described by the manufacturer (Qiagen). Cells were plated in 24-well plates to 50% confluence. Per well 0.6 µg/µl plasmid-DNA with 1 µl SuperFect Transfection Reagent was added. After 24 hours the medium was changed and transfected cell clones were selected by Geneticin-containing selection-medium. IGS4 expressing cell clones were characterized by RT-PCR and Northern Blot.

B. Method and Materials for FLIPR-Assay.

Cell Preparation:

For cell preparation the following materials were employed: plates: clear, flat-bottom, black well 96-well plates (Costar); Media: growth medium: Nut-Mix F-12 (HAM) with Glutamax (Gibco) supplemented with 10% fetal calf serum (Gibco); Incubator: 5% $CO_2$, 37° C. (Nuaire).

The method was performed as follows: Cells were seeded 24 hours or 48 hours prior to the experiment into black wall microplates. The cell density was $0.8 \times 10^{-4}$ cells/well for 48 hour incubation and $2.2 \times 10^{-4}$ cells/well for 24 hour incubation. All steps were done under sterile conditions.

Dye Loading:

In order to observe changes in intracellular calcium levels, cells must be loaded with a calcium-sensitive fluorescent dye. This dye, called FLUO-4 (Molecular Probes) is excited at 488 nm, and emits light in the 500-560 nm range, only if a complex with calcium is formed. The dye was used at 4 µM final coricentration. Pluronic acid was added to increase dye solubility and dye uptake into the cells. Probenicid, an anion exchange protein inhibitor, was added to the dye medium to increase dye retention in the cells.

The following materials were used:
2 mM dye stock: 1 mg Fluo-4 (Molecular Probes) solubilized in 443 µl low-water DMSO (Sigma). Aliquots stored at −20.
20% pluronic acid solution: 400 mg pluronic acid (Sigma) solubilized in 2 ml low-water DMSO (Sigma) at 37° C. Stored at room temperature.
Dye/pluronic acid mixture: Immediately before use, equal volumes of the dye stock and 20% pluronic acid were mixed. The dye and pluronic acid had a final concentration of 1 mM and 10%, respectively.
Probenicid, 250 mM stock solution: 710 mg probenicid (Sigma) solubilized in 5 ml 1N NaOH and mixed with 5 ml Hank's BSS without phenol red (Gibco) supplemented with 20 mM HEPES.

Loading-Buffer: 10.5 ml Hank's BSS without phenol red (Gibco) supplemented with 20 mM HEPES, 105 µl probenicid, 210 µl 1M HEPES.

Wash-Buffer: Hank's BSS without phenol red (Gibco) supplemented with 20 mM HEPES (Gibco) and 2.5 mM probenicid.

The method was worked as follows: The 2 mM stock of dye was mixed with an equal volume of 20% (w/v) pluronic acid immediately before adding to the loading-Buffer. The growth-medium was aspirated out of the well without disturbing the confluent cell layer. 100 µl loading medium was dispensed into each well using a Multidrop (Labsystems). Cell were incubated in a 5% $CO_2$, 37° C. incubator for 30 minutes. In order to calculate the background fluorescence, some wells were not dye loaded. The background fluorescence in these wells results from autofluorescence of the cells. After dye loading, cell were washed three times with Wash-Buffer (automated Denley cell washer) to reduce the basal fluorescence to 20.000-25.000 counts above background. 100 l buffer was added and cell were incubated at 37° C. till start of the experiment.

C. Preparation of Compound Plates.

The peptides were prepared at 3 µM (3× the final concentration) for initial screening. For concentration response curves peptide-solutions were prepared in concentration ranges from 30 µM to 100 nM. All peptides were diluted in buffer containing 0.1% BSA (Sigma).

The following materials were used: Peptides: porcine Neuromedin U25, rat Neuromedin U-23, porcine Neuromedin U-8 (Bachem); Dilution buffer: Hank's BSS without phenol red (Gibco) supplemented with 20 mM HEPES (Gibco) and 0.1% BSA (Sigma); plates: clear, flat-bottom, 96-well plates (Costar).

D. Assay.

The FLIPR setup parameters were set to 0.4 sec exposure length, filter 1, 50 µl fluid addition, pipettor height at 125 µl, Dispense Speed 40 µl/sec without mixing.

EXAMPLE 2b

Results

To identify the endogenous ligand for the orphan G protein coupled receptor (GPCR) IGS4, IGS4 (both forms IGS4A and IGS4B) was stably transfected in Chinese Hamster Ovary (CHO) cells. Since the G protein coupling mechanism of IGS4 was unknown, a specific CHO-cell strain was used. These CHO-cells stably express the G-protein Gα16 (CHOGα16, Molecular Devices), which is known as "universal adapter" for GPCRs (Milligan G., Marshall F. and Rees S. (1996), Gα16 as a universal G protein adapter:.implications for agonist screening strategies. TIPS 17:235-237).

The resulting CHOGα16-IGS4 cells were functionally screened on a Fluorometric Imaging Plate Reader (FLIPR) to measure mobilisation of intracellular calcium in response to putative ligands. At the concentration of 10 nM, neuromedin U-23 induced a large, transient and robust calcium-response. In contrast, CHOGα16 cells and CHOGα16 cells expressing another, unrelated orphan GPCR, did not respond to neuromedin U-23. The results of these experiments with IGS4B are shown in FIG. 4.

Furthermore, the concentration dependence of IGS4 activation by porcine and rat neuromedin U isoforms were investigated (for both forms IGS4A and IGS4B). In the range of $10^{-6}$-$10^{-12}$ M porcine neuromedin U-25, rat neuromedin U-23, porcine neuromedin U-8 induced specific IGS4-mediated calcium mobilisation in the FLIPR assay. All three Neuromedin U isoforms tested caused the same maximal activation of IGS4B with $LogE.C_{50}$ values of −10.09±0.08 (neuromedin U-8, n=4; 80 pM), −10.61±0.08 (neuromedin U-23, n=10; 50 pM) and −9.14±0.09 (neuromedin U-25, n=3; 1.2 nM). Thus, all three peptides cause potent activation of, in particular, IGS4B, suggesting that neuromedin U is the natural agonist for this receptor. The results of these experiments with IGS4B are shown in FIG. 3A (neuromedin U-8), FIG. 3B (neuromedin U-23), and FIG. 3C (neuromedin U-25).

For the IGS4A receptor somewhat lower affinities were found, but still showing that the neuromedin U peptides are good ligands for IGS4 receptors in general. The log $EC_{50}$ values found for IGS4A were as follows; for neuromedin U-8: log $EC_{50}$=−9.3±0.09 (n=1; 485 pM); for neuromedin U-23: log $EC_{50}$=−7.27±0.16 (n=6; 53 nM); and for neuromedin U-25: log $EC_{50}$=−6.18±0.14 (n=3; 65B nM).

The calcium mobilisation response seen following activation of IGS4 by neuromedin U suggests that this receptor is coupled to G proteins of the Gq/11 subfamily. In addition, basal levels of intracellular cAMP were not modulated by porcine neuromedin U-8 (1 and 10 µM) in CHOGα16-IGS4 cells, suggesting that this receptor does not couple to G proteins of the Gs subfamilies (data not shown).

EXAMPLE 3

IGS4 Hybridization on Human Multiple Tissue Expression Array (MTE™)

Human IGS4A DNA (±730 bp BamHI/HindIII insert from pGEMT-hIGS4A [ICCG #4320]) was radiolabelled via random primed incorporation of $[^s_{x-}{}^{32}P]$-dCTP to a specific activity of >$10^9$ cpm/µg using the Prime-It II kit™ (Stratagene). The labeled probe was purified from free label via Sephadex G-50 chromatography, denatured for 5 min. at 95° C. and added to the ExpressHyb hybridization solution at a final concentration of 1-1.5×$10^6$ cpm/ml. The human Multiple Tissue Expression (MTE™) Array (Clontech # 7775-1) was prehybridized and hybridized in ExpressHyb solution at 65° C. for 30 min and overnight respectively according to the recommendations of the supplier.

The hybridized MTE™ array was washed 5 times for 20 min in 2×SSC, 1% SDS at 65° C. and then 2 times for 20 min at 55° C. in 0.1×SSC, 0.5% SDS. After the washes the array was autoradiographed via phosphorimaging (Cyclone Storage Phosphor System, Packard) (FIG. 5). Hybridization data of the MTE™ array were analyzed quantitatively using the OptiQuant Image Analysis Software (Packard). Signal intensity of different spot positions containing RNA was corrected for the average background signal obtained from empty positions. The signal intensity obtained from the spot containing E. coli DNA was considered to represent a sample exhibiting no IGS4 expression. Samples with signal intensities below that of E. coli DNA were considered to be negative.

Hybridization signals for different tissues on the RNA array have been recalculated by subtracting each value with the hybridization signal observed for E. coli DNA (which is considered as the background signal). All tissues showing a lower hybridization signal are considered to be below background and to be IGS4 negative. Expression levels relative to that found in testis (100%) have been plotted and are provided in FIG. 7.

EXAMPLE 4

Tissue Distribution of IGS4 by Northern Blot Analysis

Human IGS4A DNA (±730 bp BamHI/HindIII insert from pGEMT-hIGS4A [ICCG #4320]) was radiolabelled via random primed incorporation of [$^5$x-$^{32}$P]-dCTP to a specific activity of >10$^9$ cpm/μg using the Prime-It II kit™ (Stratagene). The labeled probe was purified from free label via Sephadex G-50 chromatography, denatured for 5 min. at 95° C. and added to the ExpressHyb hybridization solution at a final concentration of 1-1.5×10$^6$ cpm/ml. The human Northern blots (Clontech #7760-1, #7759-1, #7767-1, #7755-1 and #7769-1) were prehybridized and hybridized in ExpressHyb solution at 65° C. for 30 min and overnight respectively according to the recommendations of the supplier.

After hybridization Northern blots were washed 4 times 10 min at room temperature in 2×SSC, 0.05% SDS and then 2 times 40 min at 50° C. in 0.1×SSC, 0.1% SDS. After the washes the Northern blots were autoradiographed using phosphor storage plates (Cyclone Storage Phosphor System, Packard) and X-ray films. Results of Northern blots are shown in FIG. 6.

The results of the Northern blot analysis appear to be largely consistent with those from the array hybridization (Example 3). The strongest signal (2.4 kb transcript) by far is found in testis. A weak 2.4 kb band was found in thymus, spinal cord, medulla, thyroid, thalamus, substantia nigra and a very weak band in corpus callosum, caudate nucleus and stomach. For some tissues no 2.4 kb band could be seen on Northern whereas a strong to moderate hybridization signal was observed on the MTE array (e.g. whole brain, cerebral cortex, lung, temporal and frontal lobe, amygdala, cerebellum, kidney and hippocampus).

EXAMPLE 5

Quantitative RT-PCR Analysis

IGS4 expression levels in different human tissues were also determined via real-time quantitative RT-PCR (Q-PCR) using the LightCycler™ instrument (Roche Diagnostics) and IGS4 specific TaqMan™ probes.

EXAMPLE 5a

Experimental Procedures

A. cDNA Synthesis.

Prior to reverse transcription 3 μg total RNA from the human total RNA panels I to V (Clontech # K4000-1 to K4004-1) was treated with 3U DNAse I (Life Technologies # 18068-015) in a 30 μl reaction volume (20 mM Tris pH 8.3, 50 mM KCl, 2 mM KCl) for 15 min at room temperature to destroy possibly contaminating genomic DNA. The reaction was stopped by adding 3 μl 25 mM EDTA and heating for 10 min at 65° C. 2.6 μg of the DNAse treated RNA was annealed with 1.3 μg oligo(dT) (Life Technologies # 18418-012) and subjected to reverse transcription using the Omniscript reverse transcriptase (Qiagen cat n° 205111) for 1 h at 37° C. in a 52 μl reaction volume according to the protocol recommended by the supplier of the enzyme. The Omniscript reverse transcriptase was inactivated by heating at 93° C. for 5 min.

B. Q-PCR.

Quantitative PCR reactions were carried out in a 20 μl reaction mixture, containing 1×TaqMan™ Universal PCR Mastermix (PE Applied Biosystems cat #4304437), 0.12 mg BSA/ml, 900 nM of IGS4 specific forward and reverse primers (IP14,963 and IP14,964), 250 nM of the IGS4 specific TaqMan™ probe (IP14,962) and either 1.6 μl (IGS4) or 0.16 μl (GAPDH: glyceraldehyde-3 phosphate dehydrogenase) of the cDNA synthesis reaction as template. To set up the IGS4 standard curve a dilution series (10$^7$-10$^1$ copies/reaction) of IGS4 plasmid ICCG 4320 was used whereas for the GAPDH standard curve a dilution series of the human brain cDNA synthesis reaction (0.16 μl, 0.016 and 0.0016 μl) was used as template. The 1×TaqMan™ Universal PCR Mastermix contained AmpliTaq Gold™ DNA polymerase, AmpErase™ UNG (uracil-N-glycosylase), dNTPs with dUTP, passive reference and optimized buffer components. IGS4 specific primers and TaqMan probe were designed using the Primer Express™ software (PE Applied Biosystems). Quantitative PCR reactions for human GAPDH were carried out under identical conditions as described for IGS4 except that GAPDH specific primers and TaqMan™ probe were used from the TaqMan™ GAPDH control reagents kit (PE Applied Biosystems cat n° 402869; sequence information not available from PE Applied Biosystems).

PCR reactions were carried out in glass capillary cuvettes in the LightCycler™ instrument. After an initial incubation at 50° C. for 2 min to allow the AmpErase™ UNG reaction to proceed and activation of the AmpliTaq Gold DNA polymerase (95° C. for 10 min), reaction mixtures were subjected to 40 cycles of denaturation (15 sec at 95° C.) and annealing/extension (1 min at either 60° C. [GAPDH] or at 68° C. [IGS4]). Quantification of experimental samples was carried out using the LightCycler Software version 3.0. A good linear relationship was obtained between the amount of IGS4 plasmid and the release of reporter dye within the range of 10-10$^7$ IGS4 plasmid copies. We also obtained a linear standard curve with the GAPDH TaqMan™ probe using the serially diluted brain cDNA. Relative GAPDH expression levels were in the range of 0.4 to 10.2% of that observed in skeletal muscle, which of all tissues tested had the highest GAPDH expression level. Relative IGS4 expression levels were expressed as a proportion of the level detected in spinal cord, which had the highest IGS4 expression of all tissues tested (FIG. 8). We also plotted relative IGS4 expression levels after normalization for expression of the GAPDH house keeping gene (FIG. 8).

EXAMPLE 5b

Results

Q-PCR using an IGS4 specific TaqMan probe showed that highest expression levels (without normalization for GAPDH) were found in spinal cord. IGS4 expression levels in spinal cord amounted to 11,467 copies mRNA/ng pA RNA (assuming 100% efficiency of the cDNA synthesis reaction and assuming that pA RNA constitutes 2% of total RNA). High IGS4 expression levels were also found in brain (41% of spinal cord levels), skeletal muscle (37%), cerebellum (31%), testis (19%) and in lung (12%) and heart (11%). Lower levels were found in fetal brain (5%), trachea (4%), prostate (2%) and thyroid (1.4%). After normalization for GAPDH expression, the relative IGS4 expression pattern remained largely unchanged with the exception of skeletal muscle, where the relative expression level dropped to 2% of that in spinal cord. As it is not clear whether normalization for GAPDH is a valid procedure (GAPDH expression levels can be expected to vary more or less in different cell/tissue types) we prefer to focus on the non-normalized relative expression levels.

These Q-PCR data seem to be in line with expression data from RNA array (Example 3) and Northern blot (Example 4) hybridization experiments in the sense that testis, spinal cord and brain appear to be among the most prominent expression sites. However Q-PCR analysis additionally shows important expression in a number of other tissues, such as skeletal muscle, cerebellum, lung and heart.

The ligand neuromedin U has been proposed to be a neuropeptide or neuromodulator, without the knowledge of the specific receptor (Domin J., Ghatei M. A., Chohan P. and Bloom S. R. (1987), Peptides 8: 779-784). Our investigation shows, that IGS4 is a novel member of the neuromedin U-receptor family being expressed in CNS and PNS regions, the gastrointestinal, immunological, genitourinary and cardiovascular system, skeletal muscle, thyroid, and lung.

FIG. 2 Schematic representation of the relative positions of different DNA database entries compared to the IGS4 cDNA sequence. The IGS4 cDNA sequence is indicated with the boxes (the position of the IGS4 coding sequences is indicated with the filled boxes). The relative position of IGS4 exons 1-4 is indicated above the IGS4 cDNA sequence ("="). The parts of the genomic sequence AC008571 that encode exons 1->4 are indicated with AC008571a->d respectively. The position of these fragments within the AC008571 sequence are: AC008571 a (13129-13908 of the reverse complement of AC008571), AC008571b (51676-51760 of AC008571), AC008571c (79978-80103 of the reverse complement of AC008571) and AC008571d (83060-83728 of the reverse complement of AC008571). G05725 and G20615 are STS (sequence tagged sequence) entries whereas F05107, F05108, F07531, R13353, R13890, H11359, N45474, W61169, A1432384, W61131, A1023570, F01358, F03770, Z38158, R40869, R37725, H11333 are EST entries. The parts of genomic clones A0019411 and AQ015065 that contain IGS4 exon 2 are indicated with ":". The 5' part of EST sequences F05107, F05108, F07531, R13353, R13890 and H11359 which is totally different from the IGS4 cDNA sequence is indicated with "*". AQ078563 is a genomic clone.

FIG. 3: IGS4 receptor activation by different Neuromedin U isoforms. CHOGα16-IGS4B cells were cultured in 96-well

TABLE 8

Overview of the PCR oligonucteotide primers and TaqMan probe used in the IGS4 Q-PCR reactions.

SEQ ID NO: 32 IP 14,963 5'-CCTCTTCAGCCTGGCGGTCTCTG-3'

SEQ ID NO: 33 IP 14,964 5'-GGAGGCGAAGCACACGGTCTCA-3'

SEQ ID NO: 34 IP 14,962 5'(FAM)-AGATGTGGCGCAACTACCCTTTCTTGTTCGGGCC-(TAMRA)3'

All publications, including but not limited to patents and patent applications, cited in this specification are herein incorporated by reference as if each individual publication were specifically and individually indicated to be incorporated by reference herein as though fully set forth.

SEQUENCE LISTING

<160> NUMBER OF SEQ ID NOS: 35

Figure 1:
FIG. 1 Schematic representation of the relative positions of the different cDNA clones that were isolated to generate the consensus IGS4 cDNA sequence. 5' and 3' RACE primers that were used are also indicated (IGS4R# and IGS4F# respectively) as well as the position of EST accession n° N45474. Primer IGS4R6 was located within intron 1. Some clones (e.g. HNT2311. HNT2312 and HNT2253) were only partially sequenced (only the part that was sequenced is indicated). CONSENSUS A and CONSENSUS B denote the consensus sequence of IGS4 allelic types A and B respectively. The nucleotide that was identified at each of the 4 polymorphic positions is indicated (shaded boxes) for each clone. "S" indicates a sequence ambiguity in clones HNT2211 and HNT2212 and means either "C" or "T". The coding area of IGS4A and IGS4B consensus sequences is indicated with "**". As there were some remaining sequence ambiguities in the 5' end of the consensus sequence, the IGS4ADNA and IGS4BDNA sequences have only been taken from position 86 until the end plates overnight and loaded with Fluo-4AM. The receptor mediated $Ca^{2+}$ changes were measured with FLIPR (Molecular Devices). Maxima of the fluorescence change detected by the CCD camera were normalised to 1 and are depicted as counts.
Figure 2:
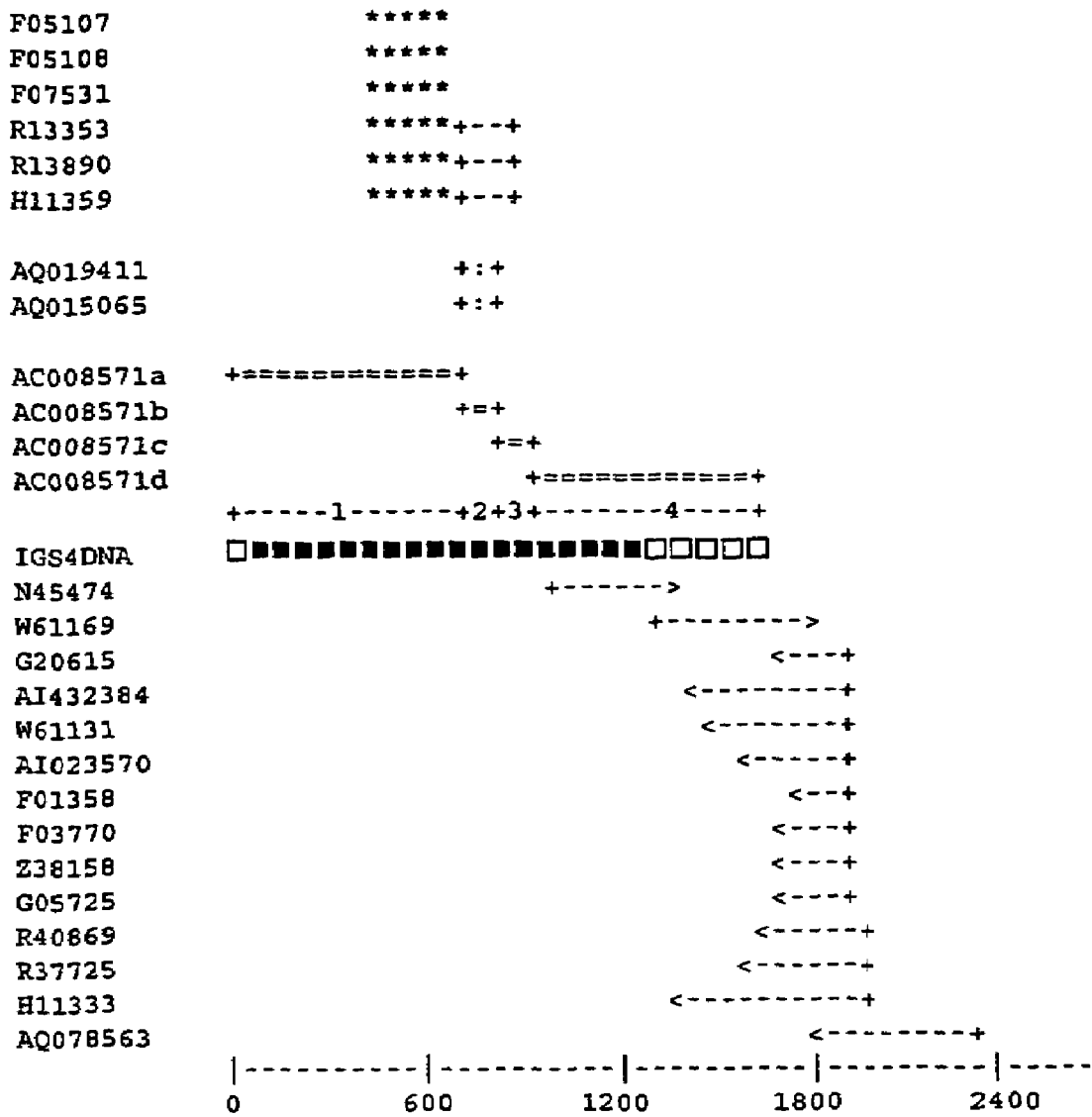
Figure 3A:
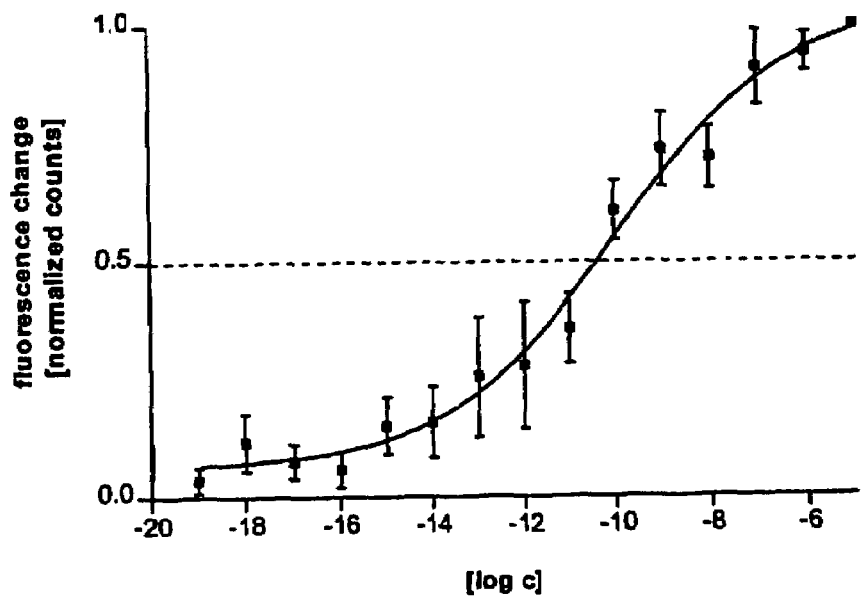
FIG. 3A: results for neuromedin U-8.
Figure 3B:
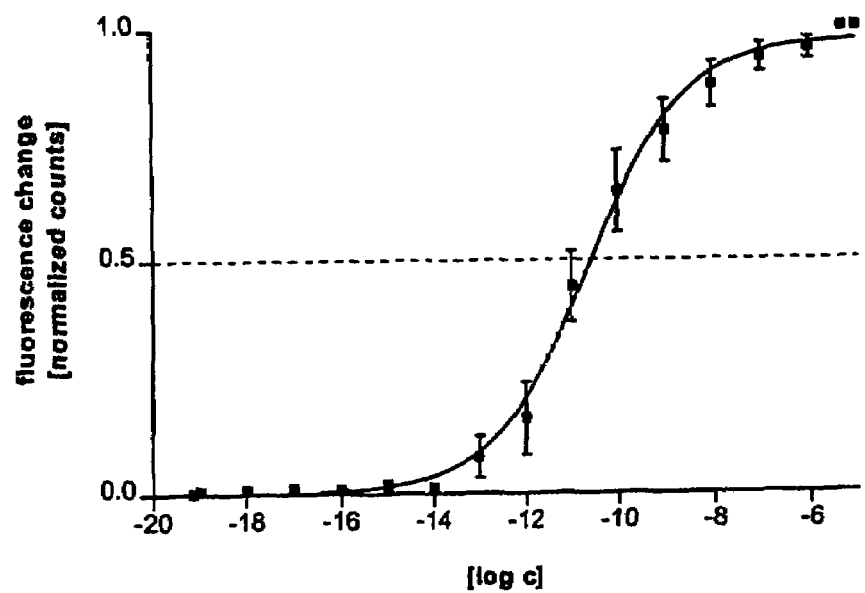
FIG. 3B: results for neuromedin U-23.
Figure 3C:
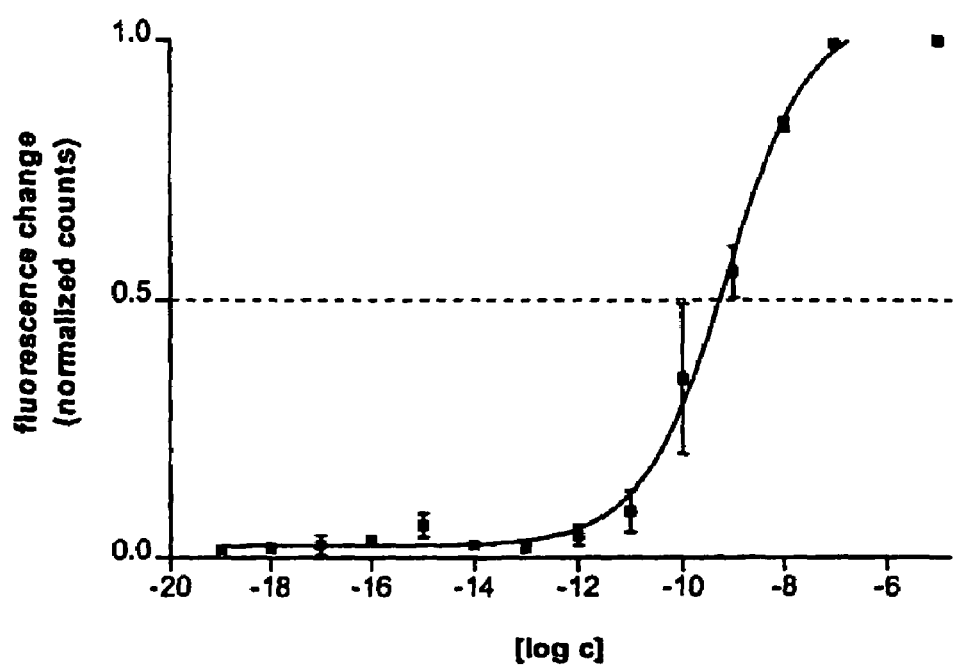
FIG. 3C: results for neuromedin U-25.
Figure 4:
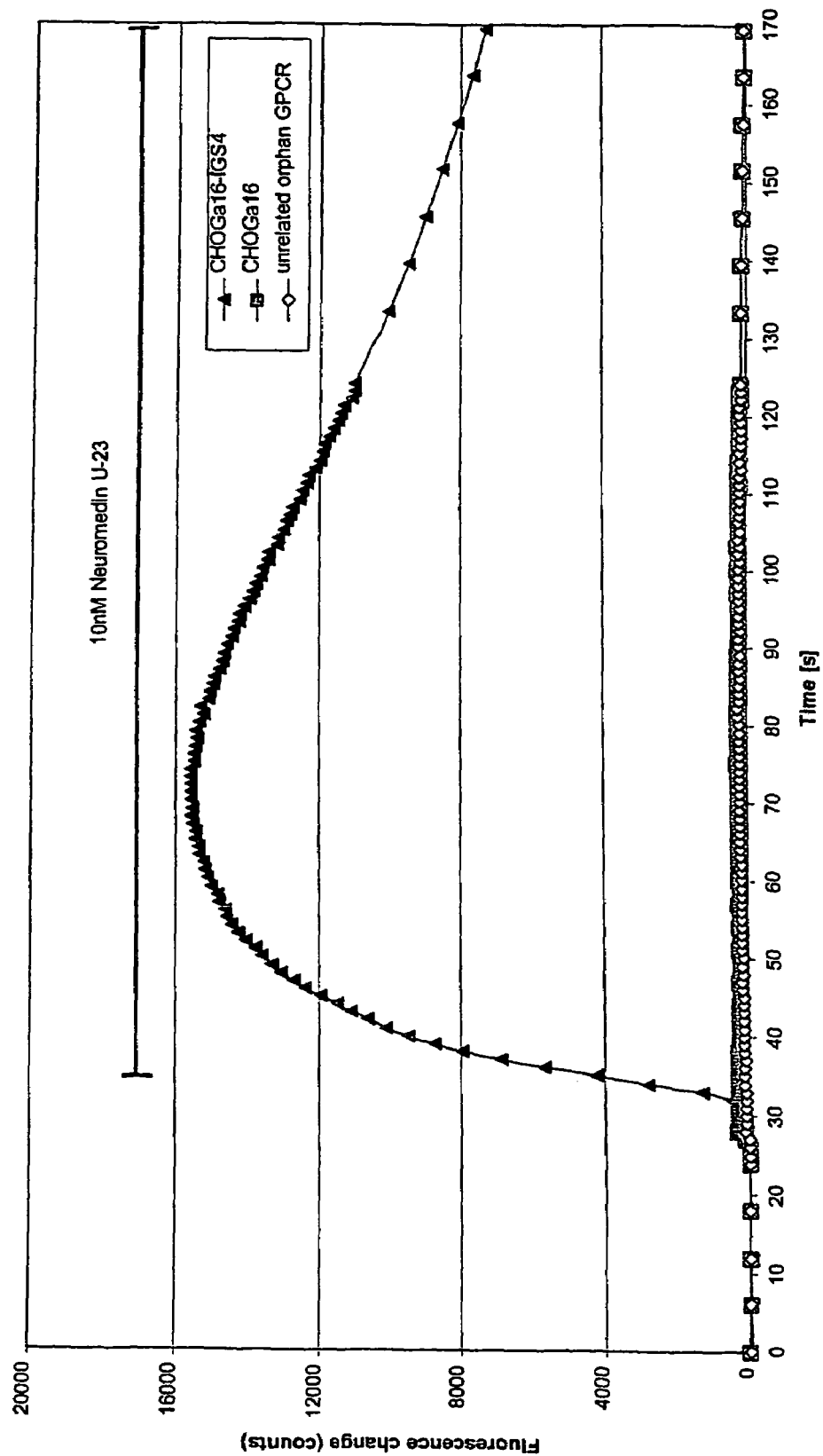
FIG. 4 Neuromedin U-23 induced intracellular $Ca^{2+}$ mobilization in CHOGα16-cells expressing IGS4B. Application of 10 nM Neuromedin U-23 to the cell lines CHOGα16-IGS4, CHOGα16 and CHOGα16 transfected with an other orphan GPCR. Cells were cultured in 96-well plates overnight and located with Fluo-4AM. Receptor mediated intracellular $Ca^{2+}$ changes were measured with FLIPR (Molecular Devices), depicted in counts detected by the CCD camera.
Figure 5:
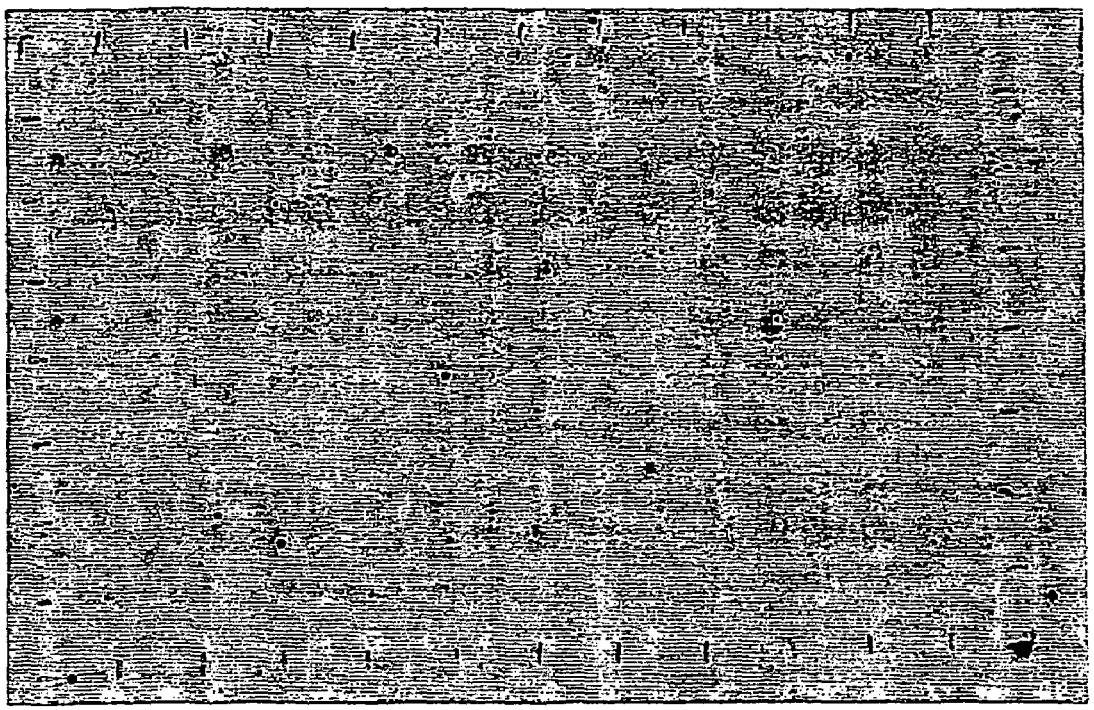
FIG. 5 Human multiple tissue expression array using a human IGS4 probe.
Figure 6:
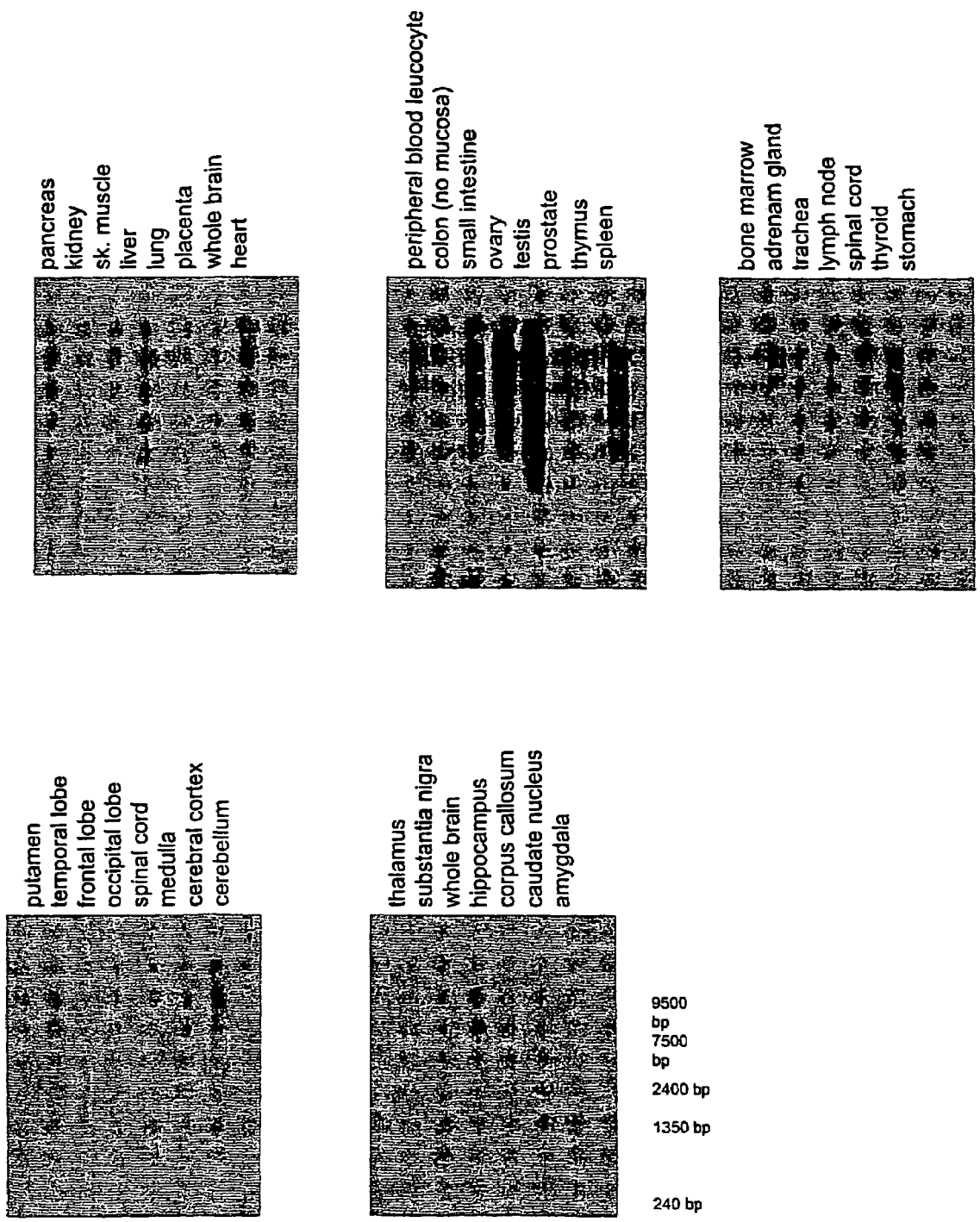
FIG. 6 Northern blot analysis using an IGS4 probe.
Figure 7:
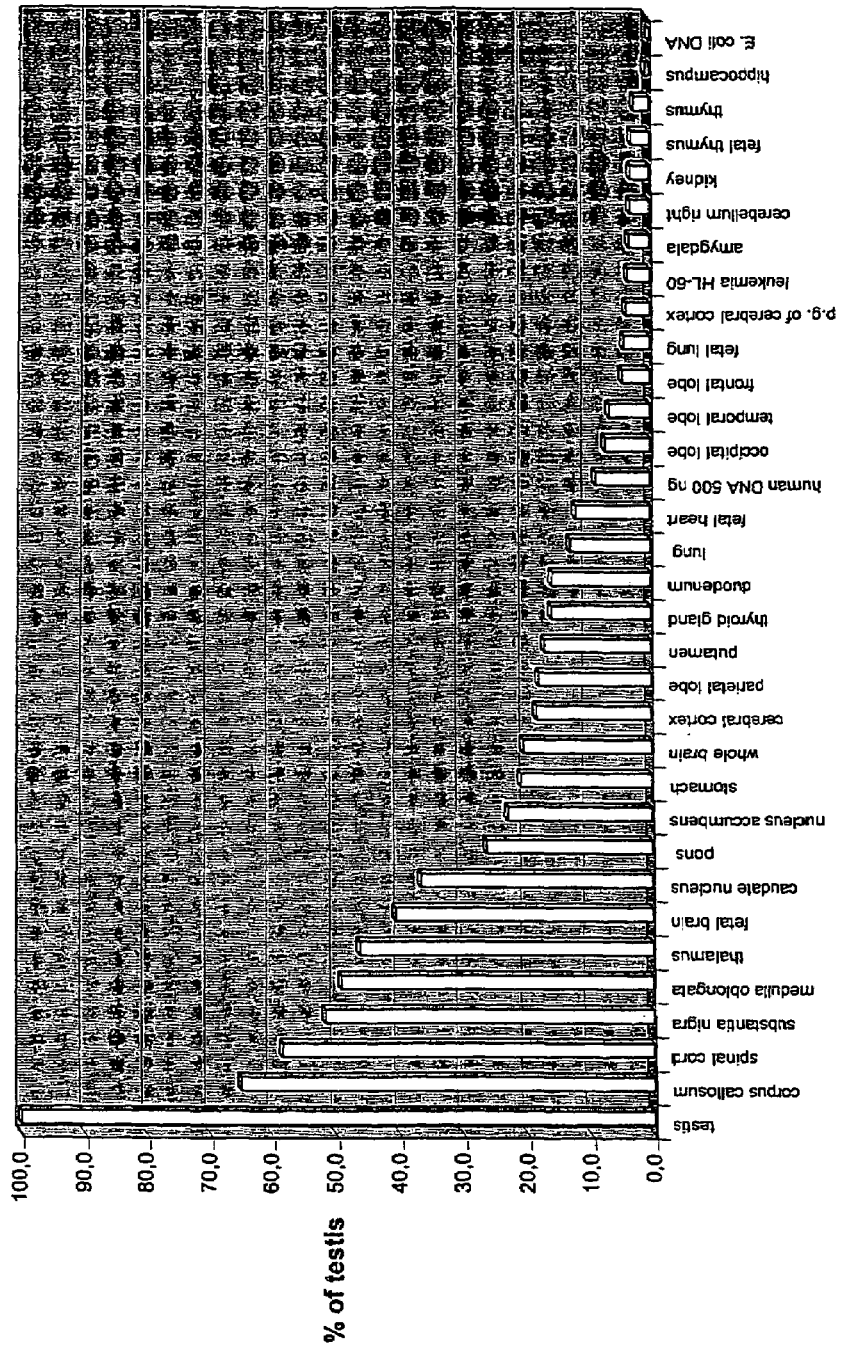
FIG. 7 IGS4 expression analysis (MTE blot).
Figure 8:
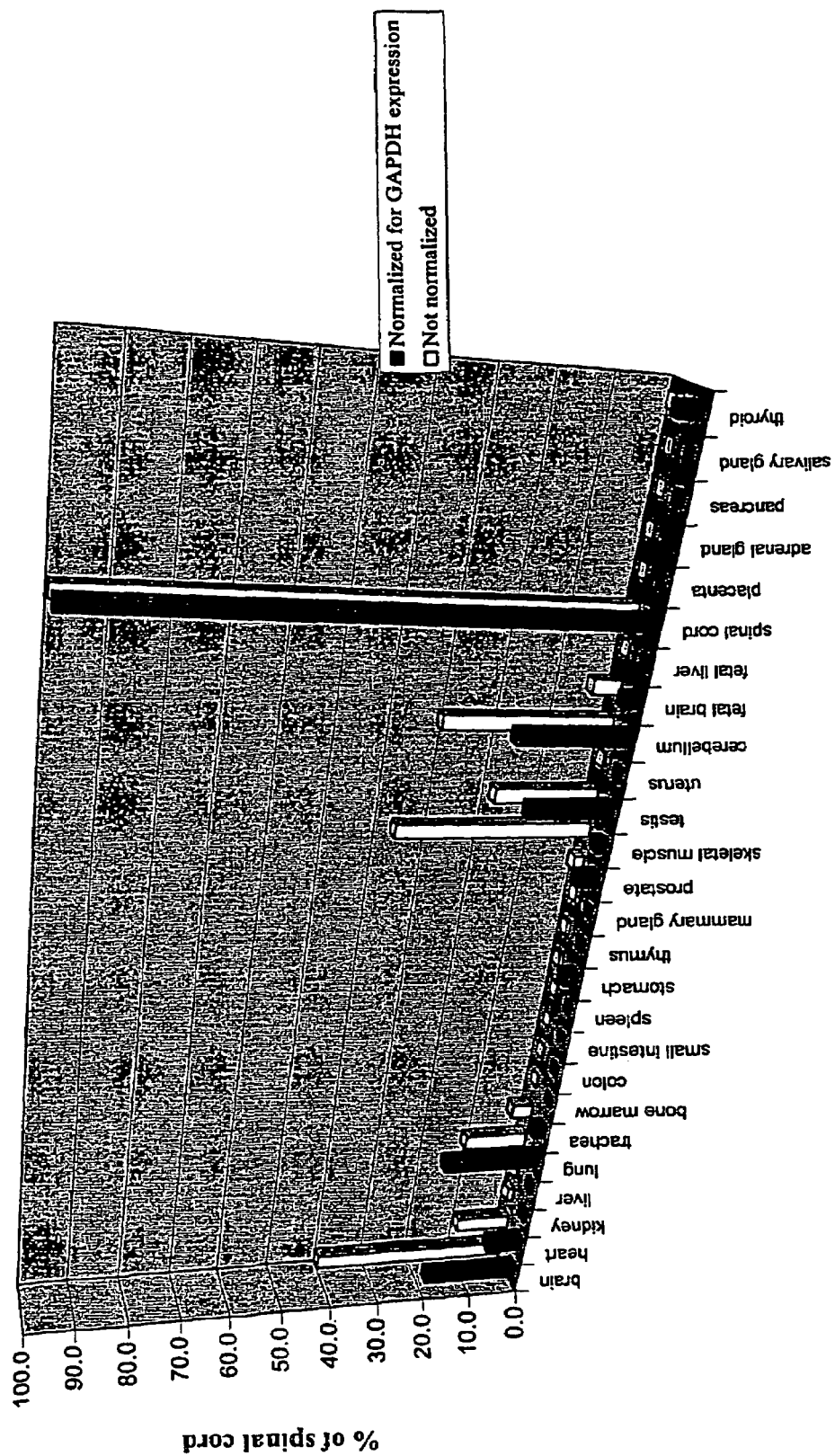
FIG. 8 Relative expression levels of IGS4 mRNA as compared to the expression observed in spinal cord. Both non-normalized and GAPDH-normalized expression levels are shown.

<210> SEQ ID NO 1
<211> LENGTH: 1658
<212> TYPE: DNA
<213> ORGANISM: Homo sapiens
<220> FEATURE:
<221> NAME/KEY: CDS
<222> LOCATION: (55)..(1299)
<223> OTHER INFORMATION: IGS4A long version

<400> SEQUENCE: 1

```
ggctcagctt gaaacagagc ctcgtaccag gggaggctca ggccttggat ttta atg        57
                                                            Met
                                                            1 tca ggg atg gaa aaa ctt cag aat gct tcc tgg atc tac cag cag aaa       105
Ser Gly Met Glu Lys Leu Gln Asn Ala Ser Trp Ile Tyr Gln Gln Lys
         5                  10                  15 cta gaa gat cca ttc cag aaa cac ctg aac agc acc gag gag tat ctg       153
Leu Glu Asp Pro Phe Gln Lys His Leu Asn Ser Thr Glu Glu Tyr Leu
     20                  25                  30 gcc ttc ctc tgc gga cct cgg cgc agc cac ttc ttc ctc ccc gtg tct       201
Ala Phe Leu Cys Gly Pro Arg Arg Ser His Phe Phe Leu Pro Val Ser
 35                  40                  45 gtg gtg tat gtg cca att ttt gtg gtg ggg gtc att ggc aat gtc ctg       249
Val Val Tyr Val Pro Ile Phe Val Val Gly Val Ile Gly Asn Val Leu
 50                  55                  60                  65 gtg tgc ctg gtg att ctg cag cac cag gct atg aag acg ccc acc aac       297
Val Cys Leu Val Ile Leu Gln His Gln Ala Met Lys Thr Pro Thr Asn
                 70                  75                  80 tac tac ctc ttc agc ctg gcg gtc tct gac ctc ctg gtc ctg ctc ctt       345
Tyr Tyr Leu Phe Ser Leu Ala Val Ser Asp Leu Leu Val Leu Leu Leu
             85                  90                  95 gga atg ccc ctg gag gtc tat gag atg tgg cgc aac tac cct ttc ttg       393
Gly Met Pro Leu Glu Val Tyr Glu Met Trp Arg Asn Tyr Pro Phe Leu
        100                 105                 110 ttc ggg ccc gtg ggc tgc tac ttc aag acg gcc ctc ttt gag acc gtg       441
Phe Gly Pro Val Gly Cys Tyr Phe Lys Thr Ala Leu Phe Glu Thr Val
    115                 120                 125 tgc ttc gcc tcc atc ctc agc atc acc acc gtc agc gtg gag cgc tac       489
Cys Phe Ala Ser Ile Leu Ser Ile Thr Thr Val Ser Val Glu Arg Tyr
130                 135                 140                 145 gtg gcc atc cta cac ccg ttc cgc gcc aaa ctg cag agc acc cgg cgc       537
Val Ala Ile Leu His Pro Phe Arg Ala Lys Leu Gln Ser Thr Arg Arg
                150                 155                 160 cgg gcc ctc agg atc ctc ggc atc gtc tgg ggc ttc tcc gtg ctc ttc       585
Arg Ala Leu Arg Ile Leu Gly Ile Val Trp Gly Phe Ser Val Leu Phe
            165                 170                 175 tcc ctg ccc aac acc agc atc cat ggc atc aag ttc cac tac ttc ccc       633
Ser Leu Pro Asn Thr Ser Ile His Gly Ile Lys Phe His Tyr Phe Pro
        180                 185                 190 aat ggg tcc ctg gtc cca ggt tcg gcc acc tgt acg gtc atc aag ccc       681
Asn Gly Ser Leu Val Pro Gly Ser Ala Thr Cys Thr Val Ile Lys Pro
    195                 200                 205 atg tgg atc tac aat ttc atc atc cag gtc acc tcc ttc cta ttc tac       729
Met Trp Ile Tyr Asn Phe Ile Ile Gln Val Thr Ser Phe Leu Phe Tyr
210                 215                 220                 225 ctc ctc ccc atg act gtc atc agt gtc ctc tac tac ctc atg gca ctc       777
Leu Leu Pro Met Thr Val Ile Ser Val Leu Tyr Tyr Leu Met Ala Leu
                230                 235                 240
```

```
aga cta aag aaa gac aaa tct ctt gag gca gat gaa ggg aat gca aat      825
Arg Leu Lys Lys Asp Lys Ser Leu Glu Ala Asp Glu Gly Asn Ala Asn
            245                 250                 255 att caa aga ccc tgc aga aaa tca gtc aac aag atg ctg ttt gtc ttg      873
Ile Gln Arg Pro Cys Arg Lys Ser Val Asn Lys Met Leu Phe Val Leu
        260                 265                 270 gtc tta gtg ttt gct atc tgt tgg gcc ccg ttc cac att gac cga ctc      921
Val Leu Val Phe Ala Ile Cys Trp Ala Pro Phe His Ile Asp Arg Leu
    275                 280                 285 ttc ttc agc ttt gtg gag gag tgg agt gaa tcc ctg gct gct gtg ttc      969
Phe Phe Ser Phe Val Glu Glu Trp Ser Glu Ser Leu Ala Ala Val Phe
290                 295                 300                 305 aac ctc gtc cat gtg gtg tca ggt gtc ttc ttc tac ctg agc tca gct     1017
Asn Leu Val His Val Val Ser Gly Val Phe Phe Tyr Leu Ser Ser Ala
                310                 315                 320 gtc aac ccc att atc tat aac cta ctg tct cgc cgc ttc cag gca gca     1065
Val Asn Pro Ile Ile Tyr Asn Leu Leu Ser Arg Arg Phe Gln Ala Ala
            325                 330                 335 ttc cag aat gtg atc tct tct ttc cac aaa cag tgg cac tcc cag cat     1113
Phe Gln Asn Val Ile Ser Ser Phe His Lys Gln Trp His Ser Gln His
        340                 345                 350 gac cca cag ttg cca cct gcc cag cgg aac atc ttc ctg aca gaa tgc     1161
Asp Pro Gln Leu Pro Pro Ala Gln Arg Asn Ile Phe Leu Thr Glu Cys
    355                 360                 365 cac ttt gtg gag ctg acc gaa gat ata ggt ccc caa ttc cca tgt cag     1209
His Phe Val Glu Leu Thr Glu Asp Ile Gly Pro Gln Phe Pro Cys Gln
370                 375                 380                 385 tca tcc atg cac aac tct cac ctc cca aca gcc ctc tct agt gaa cag     1257
Ser Ser Met His Asn Ser His Leu Pro Thr Ala Leu Ser Ser Glu Gln
                390                 395                 400 atg tca aga aca aac tat caa agc ttc cac ttt aac aaa acc             1299
Met Ser Arg Thr Asn Tyr Gln Ser Phe His Phe Asn Lys Thr
            405                 410                 415 tgaattcttt cagagctgac tctcctctat gcctcaaaac ttcagagagg aacatcccat   1359
aatgtatgcc ttctcatatg atattagaga ggtagaatgg ctcttacaac tcatgtaccc   1419
attgctagtt ttttttttt aataaacgtg aaaactgaga gttagatctg gtttcaaaac    1479
ccaagactgc ctgattttta gttatctttc cactatccta actgcctcat gccccttcac   1539
tagttcatgc caagaacgtg actggaaagg catggcacct ataccttgat taatttccat   1599
taatggaaat ggttcgtcct gagtcatcta cgttccgagt caggctgtca ctcctacta   1658
```

<210> SEQ ID NO 2
<211> LENGTH: 415
<212> TYPE: PRT
<213> ORGANISM: Homo sapiens

<400> SEQUENCE: 2

```
Met Ser Gly Met Glu Lys Leu Gln Asn Ala Ser Trp Ile Tyr Gln Gln
1               5                   10                  15

Lys Leu Glu Asp Pro Phe Gln Lys His Leu Asn Ser Thr Glu Glu Tyr
            20                  25                  30

Leu Ala Phe Leu Cys Gly Pro Arg Arg Ser His Phe Phe Leu Pro Val
        35                  40                  45

Ser Val Val Tyr Val Pro Ile Phe Val Gly Val Ile Gly Asn Val
    50                  55                  60

Leu Val Cys Leu Val Ile Leu Gln His Gln Ala Met Lys Thr Pro Thr
65                  70                  75                  80
```

-continued

```
Asn Tyr Tyr Leu Phe Ser Leu Ala Val Ser Asp Leu Val Leu Leu
             85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
            115                 120                 125

Val Cys Phe Ala Ser Ile Leu Ser Ile Thr Thr Val Ser Val Glu Arg
        130                 135                 140

Tyr Val Ala Ile Leu His Pro Phe Arg Ala Lys Leu Gln Ser Thr Arg
145                 150                 155                 160

Arg Arg Ala Leu Arg Ile Leu Gly Ile Val Trp Gly Phe Ser Val Leu
                165                 170                 175

Phe Ser Leu Pro Asn Thr Ser Ile His Gly Ile Lys Phe His Tyr Phe
                180                 185                 190

Pro Asn Gly Ser Leu Val Pro Gly Ser Ala Thr Cys Thr Val Ile Lys
            195                 200                 205

Pro Met Trp Ile Tyr Asn Phe Ile Ile Gln Val Thr Ser Phe Leu Phe
        210                 215                 220

Tyr Leu Leu Pro Met Thr Val Ile Ser Val Leu Tyr Tyr Leu Met Ala
225                 230                 235                 240

Leu Arg Leu Lys Lys Asp Lys Ser Leu Glu Ala Asp Glu Gly Asn Ala
                245                 250                 255

Asn Ile Gln Arg Pro Cys Arg Lys Ser Val Asn Lys Met Leu Phe Val
                260                 265                 270

Leu Val Leu Val Phe Ala Ile Cys Trp Ala Pro Phe His Ile Asp Arg
            275                 280                 285

Leu Phe Phe Ser Phe Val Glu Glu Trp Ser Glu Ser Leu Ala Ala Val
        290                 295                 300

Phe Asn Leu Val His Val Val Ser Gly Val Phe Phe Tyr Leu Ser Ser
305                 310                 315                 320

Ala Val Asn Pro Ile Ile Tyr Asn Leu Leu Ser Arg Arg Phe Gln Ala
                325                 330                 335

Ala Phe Gln Asn Val Ile Ser Ser Phe His Lys Gln Trp His Ser Gln
                340                 345                 350

His Asp Pro Gln Leu Pro Pro Ala Gln Arg Asn Ile Phe Leu Thr Glu
            355                 360                 365

Cys His Phe Val Glu Leu Thr Glu Asp Ile Gly Pro Gln Phe Pro Cys
        370                 375                 380

Gln Ser Ser Met His Asn Ser His Leu Pro Thr Ala Leu Ser Ser Glu
385                 390                 395                 400

Gln Met Ser Arg Thr Asn Tyr Gln Ser Phe His Phe Asn Lys Thr
                405                 410                 415

<210> SEQ ID NO 3
<211> LENGTH: 1658
<212> TYPE: DNA
<213> ORGANISM: Homo sapiens
<220> FEATURE:
<221> NAME/KEY: CDS
<222> LOCATION: (64)..(1299)
<223> OTHER INFORMATION: IGS4A short version

<400> SEQUENCE: 3
ggctcagctt gaaacagagc ctcgtaccag gggaggctca ggccttggat tttaatgtca    60 ggg atg gaa aaa ctt cag aat gct tcc tgg atc tac cag cag aaa cta   108
```

```
    Met Glu Lys Leu Gln Asn Ala Ser Trp Ile Tyr Gln Gln Lys Leu
     1               5                  10                  15 gaa gat cca ttc cag aaa cac ctg aac agc acc gag gag tat ctg gcc      156
Glu Asp Pro Phe Gln Lys His Leu Asn Ser Thr Glu Glu Tyr Leu Ala
                 20                  25                  30 ttc ctc tgc gga cct cgg cgc agc cac ttc ttc ctc ccc gtg tct gtg      204
Phe Leu Cys Gly Pro Arg Arg Ser His Phe Phe Leu Pro Val Ser Val
             35                  40                  45 gtg tat gtg cca att ttt gtg gtg ggg gtc att ggc aat gtc ctg gtg      252
Val Tyr Val Pro Ile Phe Val Val Gly Val Ile Gly Asn Val Leu Val
         50                  55                  60 tgc ctg gtg att ctg cag cac cag gct atg aag acg ccc acc aac tac      300
Cys Leu Val Ile Leu Gln His Gln Ala Met Lys Thr Pro Thr Asn Tyr
     65                  70                  75 tac ctc ttc agc ctg gcg gtc tct gac ctc ctg gtc ctg ctc ctt gga      348
Tyr Leu Phe Ser Leu Ala Val Ser Asp Leu Leu Val Leu Leu Leu Gly
 80                  85                  90                  95 atg ccc ctg gag gtc tat gag atg tgg cgc aac tac cct ttc ttg ttc      396
Met Pro Leu Glu Val Tyr Glu Met Trp Arg Asn Tyr Pro Phe Leu Phe
                100                 105                 110 ggg ccc gtg ggc tgc tac ttc aag acg gcc ctc ttt gag acc gtg tgc      444
Gly Pro Val Gly Cys Tyr Phe Lys Thr Ala Leu Phe Glu Thr Val Cys
            115                 120                 125 ttc gcc tcc atc ctc agc atc acc acc gtc agc gtg gag cgc tac gtg      492
Phe Ala Ser Ile Leu Ser Ile Thr Thr Val Ser Val Glu Arg Tyr Val
        130                 135                 140 gcc atc cta cac ccg ttc cgc gcc aaa ctg cag agc acc cgg cgc cgg      540
Ala Ile Leu His Pro Phe Arg Ala Lys Leu Gln Ser Thr Arg Arg Arg
    145                 150                 155 gcc ctc agg atc ctc ggc atc gtc tgg ggc ttc tcc gtg ctc ttc tcc      588
Ala Leu Arg Ile Leu Gly Ile Val Trp Gly Phe Ser Val Leu Phe Ser
160                 165                 170                 175 ctg ccc aac acc agc atc cat ggc atc aag ttc cac tac ttc ccc aat      636
Leu Pro Asn Thr Ser Ile His Gly Ile Lys Phe His Tyr Phe Pro Asn
                180                 185                 190 ggg tcc ctg gtc cca ggt tcg gcc acc tgt acg gtc atc aag ccc atg      684
Gly Ser Leu Val Pro Gly Ser Ala Thr Cys Thr Val Ile Lys Pro Met
            195                 200                 205 tgg atc tac aat ttc atc atc cag gtc acc tcc ttc cta ttc tac ctc      732
Trp Ile Tyr Asn Phe Ile Ile Gln Val Thr Ser Phe Leu Phe Tyr Leu
        210                 215                 220 ctc ccc atg act gtc atc agt gtc ctc tac tac ctc atg gca ctc aga      780
Leu Pro Met Thr Val Ile Ser Val Leu Tyr Tyr Leu Met Ala Leu Arg
    225                 230                 235 cta aag aaa gac aaa tct ctt gag gca gat gaa ggg aat gca aat att      828
Leu Lys Lys Asp Lys Ser Leu Glu Ala Asp Glu Gly Asn Ala Asn Ile
240                 245                 250                 255 caa aga ccc tgc aga aaa tca gtc aac aag atg ctg ttt gtc ttg gtc      876
Gln Arg Pro Cys Arg Lys Ser Val Asn Lys Met Leu Phe Val Leu Val
                260                 265                 270 tta gtg ttt gct atc tgt tgg gcc ccg ttc cac att gac cga ctc ttc      924
Leu Val Phe Ala Ile Cys Trp Ala Pro Phe His Ile Asp Arg Leu Phe
            275                 280                 285 ttc agc ttt gtg gag gag tgg agt gaa tcc ctg gct gct gtg ttc aac      972
Phe Ser Phe Val Glu Glu Trp Ser Glu Ser Leu Ala Ala Val Phe Asn
        290                 295                 300 ctc gtc cat gtg gtg tca ggt gtc ttc ttc tac ctg agc tca gct gtc     1020
Leu Val His Val Val Ser Gly Val Phe Phe Tyr Leu Ser Ser Ala Val
    305                 310                 315
```

-continued

| | | | | | | | | | | | | | | | |
|---|---|---|---|---|---|---|---|---|---|---|---|---|---|---|---|
| aac | ccc | att | atc | tat | aac | cta | ctg | tct | cgc | cgc | ttc | cag | gca | gca | ttc | 1068 |
| Asn | Pro | Ile | Ile | Tyr | Asn | Leu | Leu | Ser | Arg | Arg | Phe | Gln | Ala | Ala | Phe | |
| 320 | | | | 325 | | | | | 330 | | | | | 335 | | |

| | | | | | | | | | | | | | | | |
|---|---|---|---|---|---|---|---|---|---|---|---|---|---|---|---|
| cag | aat | gtg | atc | tct | tct | ttc | cac | aaa | cag | tgg | cac | tcc | cag | cat | gac | 1116 |
| Gln | Asn | Val | Ile | Ser | Ser | Phe | His | Lys | Gln | Trp | His | Ser | Gln | His | Asp | |
| | | | | 340 | | | | | 345 | | | | | 350 | | |

| | | | | | | | | | | | | | | | |
|---|---|---|---|---|---|---|---|---|---|---|---|---|---|---|---|
| cca | cag | ttg | cca | cct | gcc | cag | cgg | aac | atc | ttc | ctg | aca | gaa | tgc | cac | 1164 |
| Pro | Gln | Leu | Pro | Pro | Ala | Gln | Arg | Asn | Ile | Phe | Leu | Thr | Glu | Cys | His | |
| | | 355 | | | | | 360 | | | | | 365 | | | | |

| | | | | | | | | | | | | | | | |
|---|---|---|---|---|---|---|---|---|---|---|---|---|---|---|---|
| ttt | gtg | gag | ctg | acc | gaa | gat | ata | ggt | ccc | caa | ttc | cca | tgt | cag | tca | 1212 |
| Phe | Val | Glu | Leu | Thr | Glu | Asp | Ile | Gly | Pro | Gln | Phe | Pro | Cys | Gln | Ser | |
| 370 | | | | | 375 | | | | | 380 | | | | | | |

| | | | | | | | | | | | | | | | |
|---|---|---|---|---|---|---|---|---|---|---|---|---|---|---|---|
| tcc | atg | cac | aac | tct | cac | ctc | cca | aca | gcc | ctc | tct | agt | gaa | cag | atg | 1260 |
| Ser | Met | His | Asn | Ser | His | Leu | Pro | Thr | Ala | Leu | Ser | Ser | Glu | Gln | Met | |
| | 385 | | | | | 390 | | | | | 395 | | | | | |

| | | | | | | | | | | | | |
|---|---|---|---|---|---|---|---|---|---|---|---|---|
| tca | aga | aca | aac | tat | caa | agc | ttc | cac | ttt | aac | aaa | acc | tgaattcttt | 1309 |
| Ser | Arg | Thr | Asn | Tyr | Gln | Ser | Phe | His | Phe | Asn | Lys | Thr | | |
| 400 | | | | 405 | | | | | 410 | | | | | | cagagctgac tctcctctat gcctcaaaac ttcagagagg aacatcccat aatgtatgcc 1369 ttctcatatg atattagaga ggtagaatgg ctcttacaac tcatgtaccc attgctagtt 1429 ttttttttt aataaacgtg aaaactgaga gttagatctg gtttcaaaac ccaagactgc 1489 ctgattttta gttatctttc cactatccta actgcctcat gcccttcac tagttcatgc 1549 caagaacgtg actggaaagg catggcacct ataccttgat taatttccat taatggaaat 1609 ggttcgtcct gagtcatcta cgttccgagt caggctgtca ctcctacta 1658

<210> SEQ ID NO 4
<211> LENGTH: 412
<212> TYPE: PRT
<213> ORGANISM: Homo sapiens

<400> SEQUENCE: 4

Met Glu Lys Leu Gln Asn Ala Ser Trp Ile Tyr Gln Gln Lys Leu Glu
1               5                   10                  15

Asp Pro Phe Gln Lys His Leu Asn Ser Thr Glu Glu Tyr Leu Ala Phe
            20                  25                  30

Leu Cys Gly Pro Arg Arg Ser His Phe Phe Leu Pro Val Ser Val Val
        35                  40                  45

Tyr Val Pro Ile Phe Val Val Gly Val Ile Gly Asn Val Leu Val Cys
    50                  55                  60

Leu Val Ile Leu Gln His Gln Ala Met Lys Thr Pro Thr Asn Tyr Tyr
65                  70                  75                  80

Leu Phe Ser Leu Ala Val Ser Asp Leu Leu Val Leu Leu Leu Gly Met
                85                  90                  95

Pro Leu Glu Val Tyr Glu Met Trp Arg Asn Tyr Pro Phe Leu Phe Gly
            100                 105                 110

Pro Val Gly Cys Tyr Phe Lys Thr Ala Leu Phe Glu Thr Val Cys Phe
        115                 120                 125

Ala Ser Ile Leu Ser Ile Thr Thr Val Ser Val Glu Arg Tyr Val Ala
    130                 135                 140

Ile Leu His Pro Phe Arg Ala Lys Leu Gln Ser Thr Arg Arg Arg Ala
145                 150                 155                 160

Leu Arg Ile Leu Gly Ile Val Trp Gly Phe Ser Val Leu Phe Ser Leu
                165                 170                 175

Pro Asn Thr Ser Ile His Gly Ile Lys Phe His Tyr Phe Pro Asn Gly
            180                 185                 190

-continued

```
Ser Leu Val Pro Gly Ser Ala Thr Cys Thr Val Ile Lys Pro Met Trp
        195                 200                 205

Ile Tyr Asn Phe Ile Ile Gln Val Thr Ser Phe Leu Phe Tyr Leu Leu
        210                 215                 220

Pro Met Thr Val Ile Ser Val Leu Tyr Tyr Leu Met Ala Leu Arg Leu
225                 230                 235                 240

Lys Lys Asp Lys Ser Leu Glu Ala Asp Glu Gly Asn Ala Asn Ile Gln
                245                 250                 255

Arg Pro Cys Arg Lys Ser Val Asn Lys Met Leu Phe Val Leu Val Leu
            260                 265                 270

Val Phe Ala Ile Cys Trp Ala Pro Phe His Ile Asp Arg Leu Phe Phe
        275                 280                 285

Ser Phe Val Glu Glu Trp Glu Ser Leu Ala Ala Val Phe Asn Leu
        290                 295                 300

Val His Val Val Ser Gly Val Phe Phe Tyr Leu Ser Ser Ala Val Asn
305                 310                 315                 320

Pro Ile Ile Tyr Asn Leu Leu Ser Arg Arg Phe Gln Ala Ala Phe Gln
                325                 330                 335

Asn Val Ile Ser Ser Phe His Lys Gln Trp His Ser Gln His Asp Pro
            340                 345                 350

Gln Leu Pro Pro Ala Gln Arg Asn Ile Phe Leu Thr Glu Cys His Phe
        355                 360                 365

Val Glu Leu Thr Glu Asp Ile Gly Pro Gln Phe Pro Cys Gln Ser Ser
370                 375                 380

Met His Asn Ser His Leu Pro Thr Ala Leu Ser Ser Glu Gln Met Ser
385                 390                 395                 400

Arg Thr Asn Tyr Gln Ser Phe His Phe Asn Lys Thr
                405                 410

<210> SEQ ID NO 5
<211> LENGTH: 1658
<212> TYPE: DNA
<213> ORGANISM: Homo sapiens
<220> FEATURE:
<221> NAME/KEY: CDS
<222> LOCATION: (55)..(1299)
<223> OTHER INFORMATION: IGS4B long version

<400> SEQUENCE: 5
ggctcagctt gaaacagagc ctcgtaccag gggaggctca ggccttggat ttta atg        57
                                                              Met
                                                                1 tca ggg atg gaa aaa ctt cag aat gct tcc tgg atc tac cag cag aaa      105
Ser Gly Met Glu Lys Leu Gln Asn Ala Ser Trp Ile Tyr Gln Gln Lys
        5                  10                  15 cta gaa gat cca ttc cag aaa cac ctg aac agc acc gag gag tat ctg      153
Leu Glu Asp Pro Phe Gln Lys His Leu Asn Ser Thr Glu Glu Tyr Leu
    20                  25                  30 gcc ttc ctc tgc gga cct cgg cgc agc cac ttc ttc ctc ccc gtg tct      201
Ala Phe Leu Cys Gly Pro Arg Arg Ser His Phe Phe Leu Pro Val Ser
35                  40                  45 gtg gtg tat gtg cca att ttt gtg gtg ggg gtc att ggc aat gtc ctg      249
Val Val Tyr Val Pro Ile Phe Val Val Gly Val Ile Gly Asn Val Leu
 50                  55                  60                  65 gtg tgc ctg gtg att ctg cag cac cag gct atg aag acg ccc acc aac      297
Val Cys Leu Val Ile Leu Gln His Gln Ala Met Lys Thr Pro Thr Asn
         70                  75                  80
```

| | | |
|---|---|---|
| tac tac ctc ttc agc ctg gcg gtc tct gac ctc ctg gtc ctg ctc ctt<br>Tyr Tyr Leu Phe Ser Leu Ala Val Ser Asp Leu Leu Val Leu Leu Leu<br>                  85                        90                        95 | 345 |
| gga atg ccc ctg gag gtc tat gag atg tgg cgc aac tac cct ttc ttg<br>Gly Met Pro Leu Glu Val Tyr Glu Met Trp Arg Asn Tyr Pro Phe Leu<br>          100                     105                     110 | 393 |
| ttc ggg ccc gtg ggc tgc tac ttc aag acg gcc ctc ttt gag acc gtg<br>Phe Gly Pro Val Gly Cys Tyr Phe Lys Thr Ala Leu Phe Glu Thr Val<br>115                     120                       125 | 441 |
| tgc ttc gcc tcc atc ctc agc atc acc acc gtc agc gtg gag cgc tac<br>Cys Phe Ala Ser Ile Leu Ser Ile Thr Thr Val Ser Val Glu Arg Tyr<br>130                   135                    140                 145 | 489 |
| gtg gcc atc cta cac ccg ttc cgc gcc aaa ctg cag agc acc cgg cgc<br>Val Ala Ile Leu His Pro Phe Arg Ala Lys Leu Gln Ser Thr Arg Arg<br>                 150                    155                   160 | 537 |
| cgg gcc ctc agg atc ctc ggc atc gtc tgg ggc ttc tcc gtg ctc ttc<br>Arg Ala Leu Arg Ile Leu Gly Ile Val Trp Gly Phe Ser Val Leu Phe<br>         165                     170                     175 | 585 |
| tcc ctg ccc aac acc agc atc cat ggc atc aag ttc cac tac ttc ccc<br>Ser Leu Pro Asn Thr Ser Ile His Gly Ile Lys Phe His Tyr Phe Pro<br>                 180                    185                   190 | 633 |
| aat ggg tcc ctg gtc cca ggt tcg gcc acc tgt acg gtc atc aag ccc<br>Asn Gly Ser Leu Val Pro Gly Ser Ala Thr Cys Thr Val Ile Lys Pro<br>       195                     200                     205 | 681 |
| atg tgg atc tac aat ttc atc atc cag gtc acc tcc ttc cta ttc tac<br>Met Trp Ile Tyr Asn Phe Ile Ile Gln Val Thr Ser Phe Leu Phe Tyr<br>210                     215                    220                 225 | 729 |
| ctc ctc ccc atg act gtc atc agt gtc ctc tac tac ctc atg gca ctc<br>Leu Leu Pro Met Thr Val Ile Ser Val Leu Tyr Tyr Leu Met Ala Leu<br>                      230                    235                 240 | 777 |
| aga cta aag aaa gac aaa tct ctt gag gca gat gaa ggg aat gca aat<br>Arg Leu Lys Lys Asp Lys Ser Leu Glu Ala Asp Glu Gly Asn Ala Asn<br>               245                    250                   255 | 825 |
| att caa aga ccc tgc aga aaa tca gtc aac aag atg ctg ttt gtc ttg<br>Ile Gln Arg Pro Cys Arg Lys Ser Val Asn Lys Met Leu Phe Val Leu<br>260                     265                    270 | 873 |
| gtc tta gtg ttt gct atc tgt tgg gcc ccg ttc cac att gac cga ctc<br>Val Leu Val Phe Ala Ile Cys Trp Ala Pro Phe His Ile Asp Arg Leu<br>275                     280                    285 | 921 |
| ttc ttc agc ttt gtg gag gag tgg act gaa tcc ctg gct gct gtg ttc<br>Phe Phe Ser Phe Val Glu Glu Trp Thr Glu Ser Leu Ala Ala Val Phe<br>290                     295                    300                 305 | 969 |
| aac ctc gtc cat gtg gtg tca ggt gtc tta ttc tac ctg agc tca gct<br>Asn Leu Val His Val Val Ser Gly Val Leu Phe Tyr Leu Ser Ser Ala<br>                 310                    315                 320 | 1017 |
| gtc aac ccc att atc tat aac cta ctg tct cgc cgc ttc cag gca gca<br>Val Asn Pro Ile Ile Tyr Asn Leu Leu Ser Arg Arg Phe Gln Ala Ala<br>             325                    330                 335 | 1065 |
| ttc cag aat gtg atc tct tct ttc cac aaa cag tgg cac tcc cag cat<br>Phe Gln Asn Val Ile Ser Ser Phe His Lys Gln Trp His Ser Gln His<br>340                     345                    350 | 1113 |
| gac cca cag ttg cca cct gcc cag cgg aac atc ttc ctg aca gaa tgc<br>Asp Pro Gln Leu Pro Pro Ala Gln Arg Asn Ile Phe Leu Thr Glu Cys<br>355                     360                    365 | 1161 |
| cac ttt gtg gag ctg acc gaa gat ata ggt ccc caa ttc cta tgt cag<br>His Phe Val Glu Leu Thr Glu Asp Ile Gly Pro Gln Phe Leu Cys Gln<br>370                     375                    380                 385 | 1209 |
| tca tcc gtg cac aac tct cac ctc cca aca gcc ctc tct agt gaa cag<br>Ser Ser Val His Asn Ser His Leu Pro Thr Ala Leu Ser Ser Glu Gln<br>                 390                    395                 400 | 1257 |

```
atg tca aga aca aac tat caa agc ttc cac ttt aac aaa acc          1299
Met Ser Arg Thr Asn Tyr Gln Ser Phe His Phe Asn Lys Thr
        405                 410                 415 tgaattcttt cagagctgac tctcctctat gcctcaaaac ttcagagagg aacatcccat  1359
aatgtatgcc ttctcatatg aaattagaga ggtagaatgg ctcttacaac tcatgtaccc  1419
attgctagtt ttttttttt aataaacgtg aaaactgaga gttagatctg gtttcaaaac   1479
ccaagactgc ctgattttta gttatctttc cactatccta actgcctcat gcccttcac   1539 tagttcatgc caagaacgtg actggaaagg catggcacct ataccttgat taatttccat  1599
taatggaaat ggttcgtcct gagtcatcta cgttccgagt caggctgtca ctcctacta   1658

<210> SEQ ID NO 6
<211> LENGTH: 415
<212> TYPE: PRT
<213> ORGANISM: Homo sapiens

<400> SEQUENCE: 6

Met Ser Gly Met Glu Lys Leu Gln Asn Ala Ser Trp Ile Tyr Gln Gln
 1               5                  10                  15

Lys Leu Glu Asp Pro Phe Gln Lys His Leu Asn Ser Thr Glu Glu Tyr
                20                  25                  30

Leu Ala Phe Leu Cys Gly Pro Arg Arg Ser His Phe Phe Leu Pro Val
            35                  40                  45

Ser Val Val Tyr Val Pro Ile Phe Val Val Gly Val Ile Gly Asn Val
        50                  55                  60

Leu Val Cys Leu Val Ile Leu Gln His Gln Ala Met Lys Thr Pro Thr
65                  70                  75                  80

Asn Tyr Tyr Leu Phe Ser Leu Ala Val Ser Asp Leu Leu Val Leu Leu
                85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
        115                 120                 125

Val Cys Phe Ala Ser Ile Leu Ser Ile Thr Thr Val Ser Val Glu Arg
    130                 135                 140

Tyr Val Ala Ile Leu His Pro Phe Arg Ala Lys Leu Gln Ser Thr Arg
145                 150                 155                 160

Arg Arg Ala Leu Arg Ile Leu Gly Ile Val Trp Gly Phe Ser Val Leu
                165                 170                 175

Phe Ser Leu Pro Asn Thr Ser Ile His Gly Ile Lys Phe His Tyr Phe
            180                 185                 190

Pro Asn Gly Ser Leu Val Pro Gly Ser Ala Thr Cys Thr Val Ile Lys
        195                 200                 205

Pro Met Trp Ile Tyr Asn Phe Ile Ile Gln Val Thr Ser Phe Leu Phe
    210                 215                 220

Tyr Leu Leu Pro Met Thr Val Ile Ser Val Leu Tyr Tyr Leu Met Ala
225                 230                 235                 240

Leu Arg Leu Lys Lys Asp Lys Ser Leu Glu Ala Asp Glu Gly Asn Ala
                245                 250                 255

Asn Ile Gln Arg Pro Cys Arg Lys Ser Val Asn Lys Met Leu Phe Val
            260                 265                 270

Leu Val Leu Val Phe Ala Ile Cys Trp Ala Pro Phe His Ile Asp Arg
        275                 280                 285
```

```
Leu Phe Phe Ser Phe Val Glu Glu Trp Thr Glu Ser Leu Ala Ala Val
    290                 295                 300

Phe Asn Leu Val His Val Val Ser Gly Val Leu Phe Tyr Leu Ser Ser
305                 310                 315                 320

Ala Val Asn Pro Ile Ile Tyr Asn Leu Leu Ser Arg Arg Phe Gln Ala
                325                 330                 335

Ala Phe Gln Asn Val Ile Ser Ser Phe His Lys Gln Trp His Ser Gln
                340                 345                 350

His Asp Pro Gln Leu Pro Pro Ala Gln Arg Asn Ile Phe Leu Thr Glu
            355                 360                 365

Cys His Phe Val Glu Leu Thr Glu Asp Ile Gly Pro Gln Phe Leu Cys
    370                 375                 380

Gln Ser Ser Val His Asn Ser His Leu Pro Thr Ala Leu Ser Ser Glu
385                 390                 395                 400

Gln Met Ser Arg Thr Asn Tyr Gln Ser Phe His Phe Asn Lys Thr
                405                 410                 415

<210> SEQ ID NO 7
<211> LENGTH: 1658
<212> TYPE: DNA
<213> ORGANISM: Homo sapiens
<220> FEATURE:
<221> NAME/KEY: CDS
<222> LOCATION: (64)..(1299)
<223> OTHER INFORMATION: IGS4B short version

<400> SEQUENCE: 7
ggctcagctt gaaacagagc ctcgtaccag gggaggctca ggccttggat tttaatgtca    60 ggg atg gaa aaa ctt cag aat gct tcc tgg atc tac cag cag aaa cta   108
    Met Glu Lys Leu Gln Asn Ala Ser Trp Ile Tyr Gln Gln Lys Leu
    1               5                   10                  15 gaa gat cca ttc cag aaa cac ctg aac agc acc gag gag tat ctg gcc   156
Glu Asp Pro Phe Gln Lys His Leu Asn Ser Thr Glu Glu Tyr Leu Ala
                20                  25                  30 ttc ctc tgc gga cct cgg cgc agc cac ttc ttc ctc ccc gtg tct gtg   204
Phe Leu Cys Gly Pro Arg Arg Ser His Phe Phe Leu Pro Val Ser Val
            35                  40                  45 gtg tat gtg cca att ttt gtg gtg ggg gtc att ggc aat gtc ctg gtg   252
Val Tyr Val Pro Ile Phe Val Val Gly Val Ile Gly Asn Val Leu Val
        50                  55                  60 tgc ctg gtg att ctg cag cac cag gct atg aag acg ccc acc aac tac   300
Cys Leu Val Ile Leu Gln His Gln Ala Met Lys Thr Pro Thr Asn Tyr
    65                  70                  75 tac ctc ttc agc ctg gcg gtc tct gac ctc ctg gtc ctg ctc ctt gga   348
Tyr Leu Phe Ser Leu Ala Val Ser Asp Leu Leu Val Leu Leu Leu Gly
80                  85                  90                  95 atg ccc ctg gag gtc tat gag atg tgg cgc aac tac cct ttc ttg ttc   396
Met Pro Leu Glu Val Tyr Glu Met Trp Arg Asn Tyr Pro Phe Leu Phe
                100                 105                 110 ggg ccc gtg ggc tgc tac ttc aag acg gcc ctc ttt gag acc gtg tgc   444
Gly Pro Val Gly Cys Tyr Phe Lys Thr Ala Leu Phe Glu Thr Val Cys
            115                 120                 125 ttc gcc tcc atc ctc agc atc acc acc gtc agc gtg gag cgc tac gtg   492
Phe Ala Ser Ile Leu Ser Ile Thr Thr Val Ser Val Glu Arg Tyr Val
        130                 135                 140 gcc atc cta cac ccg ttc cgc gcc aaa ctg cag agc acc cgg cgc cgg   540
Ala Ile Leu His Pro Phe Arg Ala Lys Leu Gln Ser Thr Arg Arg Arg
    145                 150                 155 gcc ctc agg atc ctc ggc atc gtc tgg ggc ttc tcc gtg ctc ttc tcc   588
```

```
                Ala Leu Arg Ile Leu Gly Ile Val Trp Gly Phe Ser Val Leu Phe Ser
                160                 165                 170                 175 ctg ccc aac acc agc atc cat ggc atc aag ttc cac tac ttc ccc aat            636
Leu Pro Asn Thr Ser Ile His Gly Ile Lys Phe His Tyr Phe Pro Asn
                180                 185                 190 ggg tcc ctg gtc cca ggt tcg gcc acc tgt acg gtc atc aag ccc atg            684
Gly Ser Leu Val Pro Gly Ser Ala Thr Cys Thr Val Ile Lys Pro Met
            195                 200                 205 tgg atc tac aat ttc atc atc cag gtc acc tcc ttc cta ttc tac ctc            732
Trp Ile Tyr Asn Phe Ile Ile Gln Val Thr Ser Phe Leu Phe Tyr Leu
            210                 215                 220 ctc ccc atg act gtc atc agt gtc ctc tac tac ctc atg gca ctc aga            780
Leu Pro Met Thr Val Ile Ser Val Leu Tyr Tyr Leu Met Ala Leu Arg
225                 230                 235 cta aag aaa gac aaa tct ctt gag gca gat gaa ggg aat gca aat att            828
Leu Lys Lys Asp Lys Ser Leu Glu Ala Asp Glu Gly Asn Ala Asn Ile
240                 245                 250                 255 caa aga ccc tgc aga aaa tca gtc aac aag atg ctg ttt gtc ttg gtc            876
Gln Arg Pro Cys Arg Lys Ser Val Asn Lys Met Leu Phe Val Leu Val
                260                 265                 270 tta gtg ttt gct atc tgt tgg gcc ccg ttc cac att gac cga ctc ttc            924
Leu Val Phe Ala Ile Cys Trp Ala Pro Phe His Ile Asp Arg Leu Phe
            275                 280                 285 ttc agc ttt gtg gag gag tgg act gaa tcc ctg gct gct gtg ttc aac            972
Phe Ser Phe Val Glu Glu Trp Thr Glu Ser Leu Ala Ala Val Phe Asn
            290                 295                 300 ctc gtc cat gtg gtg tca ggt gtc tta ttc tac ctg agc tca gct gtc           1020
Leu Val His Val Val Ser Gly Val Leu Phe Tyr Leu Ser Ser Ala Val
305                 310                 315 aac ccc att atc tat aac cta ctg tct cgc cgc ttc cag gca gca ttc           1068
Asn Pro Ile Ile Tyr Asn Leu Leu Ser Arg Arg Phe Gln Ala Ala Phe
320                 325                 330                 335 cag aat gtg atc tct tct ttc cac aaa cag tgg cac tcc cag cat gac           1116
Gln Asn Val Ile Ser Ser Phe His Lys Gln Trp His Ser Gln His Asp
                340                 345                 350 cca cag ttg cca cct gcc cag cgg aac atc ttc ctg aca gaa tgc cac           1164
Pro Gln Leu Pro Pro Ala Gln Arg Asn Ile Phe Leu Thr Glu Cys His
            355                 360                 365 ttt gtg gag ctg acc gaa gat ata ggt ccc caa ttc cta tgt cag tca           1212
Phe Val Glu Leu Thr Glu Asp Ile Gly Pro Gln Phe Leu Cys Gln Ser
            370                 375                 380 tcc gtg cac aac tct cac ctc cca aca gcc ctc tct agt gaa cag atg           1260
Ser Val His Asn Ser His Leu Pro Thr Ala Leu Ser Ser Glu Gln Met
385                 390                 395 tca aga aca aac tat caa agc ttc cac ttt aac aaa acc tgaattcttt           1309
Ser Arg Thr Asn Tyr Gln Ser Phe His Phe Asn Lys Thr
400                 405                 410 cagagctgac tctcctctat gcctcaaaac ttcagagagg aacatcccat aatgtatgcc         1369
ttctcatatg aaattagaga ggtagaatgg ctccttacaac tcatgtaccc attgctagtt        1429 ttttttttt aataaacgtg aaaactgaga gttagatctg gtttcaaaac ccaagactgc          1489
ctgattttta gttatctttc cactatccta actgcctcat gccccttcac tagttcatgc         1549
caagaacgtg actggaaagg catggcacct ataccttgat taatttccat taatggaaat        1609
ggttcgtcct gagtcatcta cgttccgagt caggctgtca ctcctacta                    1658

<210> SEQ ID NO 8
<211> LENGTH: 412
<212> TYPE: PRT
```

<213> ORGANISM: Homo sapiens

<400> SEQUENCE: 8

```
Met Glu Lys Leu Gln Asn Ala Ser Trp Ile Tyr Gln Gln Lys Leu Glu
 1               5                  10                  15

Asp Pro Phe Gln Lys His Leu Asn Ser Thr Glu Tyr Leu Ala Phe
             20                  25                  30

Leu Cys Gly Pro Arg Arg Ser His Phe Phe Leu Pro Val Ser Val Val
         35                  40                  45

Tyr Val Pro Ile Phe Val Val Gly Val Ile Gly Asn Val Leu Val Cys
     50                  55                  60

Leu Val Ile Leu Gln His Gln Ala Met Lys Thr Pro Thr Asn Tyr Tyr
 65                  70                  75                  80

Leu Phe Ser Leu Ala Val Ser Asp Leu Leu Val Leu Leu Leu Gly Met
                 85                  90                  95

Pro Leu Glu Val Tyr Glu Met Trp Arg Asn Tyr Pro Phe Leu Phe Gly
            100                 105                 110

Pro Val Gly Cys Tyr Phe Lys Thr Ala Leu Phe Glu Thr Val Cys Phe
        115                 120                 125

Ala Ser Ile Leu Ser Ile Thr Thr Val Ser Val Glu Arg Tyr Val Ala
    130                 135                 140

Ile Leu His Pro Phe Arg Ala Lys Leu Gln Ser Thr Arg Arg Arg Ala
145                 150                 155                 160

Leu Arg Ile Leu Gly Ile Val Trp Gly Phe Ser Val Leu Phe Ser Leu
                165                 170                 175

Pro Asn Thr Ser Ile His Gly Ile Lys Phe His Tyr Phe Pro Asn Gly
            180                 185                 190

Ser Leu Val Pro Gly Ser Ala Thr Cys Thr Val Ile Lys Pro Met Trp
        195                 200                 205

Ile Tyr Asn Phe Ile Ile Gln Val Thr Ser Phe Leu Phe Tyr Leu Leu
    210                 215                 220

Pro Met Thr Val Ile Ser Val Leu Tyr Tyr Leu Met Ala Leu Arg Leu
225                 230                 235                 240

Lys Lys Asp Lys Ser Leu Glu Ala Asp Glu Gly Asn Ala Asn Ile Gln
                245                 250                 255

Arg Pro Cys Arg Lys Ser Val Asn Lys Met Leu Phe Val Leu Val Leu
            260                 265                 270

Val Phe Ala Ile Cys Trp Ala Pro Phe His Ile Asp Arg Leu Phe Phe
        275                 280                 285

Ser Phe Val Glu Glu Trp Thr Glu Ser Leu Ala Ala Val Phe Asn Leu
    290                 295                 300

Val His Val Val Ser Gly Val Leu Phe Tyr Leu Ser Ser Ala Val Asn
305                 310                 315                 320

Pro Ile Ile Tyr Asn Leu Leu Ser Arg Arg Phe Gln Ala Ala Phe Gln
                325                 330                 335

Asn Val Ile Ser Ser Phe His Lys Gln Trp His Ser Gln His Asp Pro
            340                 345                 350

Gln Leu Pro Pro Ala Gln Arg Asn Ile Phe Leu Thr Glu Cys His Phe
        355                 360                 365

Val Glu Leu Thr Glu Asp Ile Gly Pro Gln Phe Leu Cys Gln Ser Ser
    370                 375                 380

Val His Asn Ser His Leu Pro Thr Ala Leu Ser Ser Glu Gln Met Ser
385                 390                 395                 400
```

```
Arg Thr Asn Tyr Gln Ser Phe His Phe Asn Lys Thr
            405                 410
```

```
<210> SEQ ID NO 9
<211> LENGTH: 1594
<212> TYPE: DNA
<213> ORGANISM: Homo sapiens
<220> FEATURE:
<221> NAME/KEY: CDS
<222> LOCATION: (55)..(942)
<223> OTHER INFORMATION: IGS4A truncated DNA long version

<400> SEQUENCE: 9
```

```
ggctcagctt gaaacagagc ctcgtaccag gggaggctca ggccttggat ttta atg         57
                                                             Met
                                                              1 tca ggg atg gaa aaa ctt cag aat gct tcc tgg atc tac cag cag aaa        105
Ser Gly Met Glu Lys Leu Gln Asn Ala Ser Trp Ile Tyr Gln Gln Lys
          5                  10                  15 cta gaa gat cca ttc cag aaa cac ctg aac agc acc gag gag tat ctg        153
Leu Glu Asp Pro Phe Gln Lys His Leu Asn Ser Thr Glu Glu Tyr Leu
     20                  25                  30 gcc ttc ctc tgc gga cct cgg cgc agc cac ttc ctc ccc gtg tct            201
Ala Phe Leu Cys Gly Pro Arg Arg Ser His Phe Leu Pro Val Ser
 35                  40                  45 gtg gtg tat gtg cca att ttt gtg gtg ggg gtc att ggc aat gtc ctg        249
Val Val Tyr Val Pro Ile Phe Val Val Gly Val Ile Gly Asn Val Leu
 50                  55                  60                  65 gtg tgc ctg gtg att ctg cag cac cag gct atg aag acg ccc acc aac        297
Val Cys Leu Val Ile Leu Gln His Gln Ala Met Lys Thr Pro Thr Asn
             70                  75                  80 tac tac ctc ttc agc ctg gcg gtc tct gac ctc ctg gtc ctg ctc ctt        345
Tyr Tyr Leu Phe Ser Leu Ala Val Ser Asp Leu Leu Val Leu Leu Leu
         85                  90                  95 gga atg ccc ctg gag gtc tat gag atg tgg cgc aac tac cct ttc ttg        393
Gly Met Pro Leu Glu Val Tyr Glu Met Trp Arg Asn Tyr Pro Phe Leu
    100                 105                 110 ttc ggg ccc gtg ggc tgc tac ttc aag acg gcc ctc ttt gag acc gtg        441
Phe Gly Pro Val Gly Cys Tyr Phe Lys Thr Ala Leu Phe Glu Thr Val
115                 120                 125 tgc ttc gcc tcc atc ctc agc atc acc acc gtc agc gtg gag cgc tac        489
Cys Phe Ala Ser Ile Leu Ser Ile Thr Thr Val Ser Val Glu Arg Tyr
130                 135                 140                 145 gtg gcc atc cta cac ccg ttc cgc gcc aaa ctg cag agc acc cgg cgc        537
Val Ala Ile Leu His Pro Phe Arg Ala Lys Leu Gln Ser Thr Arg Arg
            150                 155                 160 cgg gcc ctc agg atc ctc ggc atc gtc tgg ggc ttc tcc gtg ctc ttc        585
Arg Ala Leu Arg Ile Leu Gly Ile Val Trp Gly Phe Ser Val Leu Phe
                165                 170                 175 tcc ctg ccc aac acc agc atc cat ggc atc aag ttc cac tac ttc ccc        633
Ser Leu Pro Asn Thr Ser Ile His Gly Ile Lys Phe His Tyr Phe Pro
            180                 185                 190 aat ggg tcc ctg gtc cca ggt tcg gcc acc tgt acg gtc atc aag ccc        681
Asn Gly Ser Leu Val Pro Gly Ser Ala Thr Cys Thr Val Ile Lys Pro
        195                 200                 205 atg tgg atc tac aat ttc atc atc cag gtc acc tcc ttc cta ttc tac        729
Met Trp Ile Tyr Asn Phe Ile Ile Gln Val Thr Ser Phe Leu Phe Tyr
210                 215                 220                 225 ctc ctc ccc atg act gtc atc agt gtc ctc tac tac ctc atg gca ctc        777
Leu Leu Pro Met Thr Val Ile Ser Val Leu Tyr Tyr Leu Met Ala Leu
            230                 235                 240
```

-continued

```
aga cta aag aaa gac aaa tct ctt gag gca gat gaa ggg aat gca aat      825
Arg Leu Lys Lys Asp Lys Ser Leu Glu Ala Asp Glu Gly Asn Ala Asn
            245                 250                 255 att caa aga ccc tgc aga aaa tca gtc aac aag atg ctg tct ttg tgg      873
Ile Gln Arg Pro Cys Arg Lys Ser Val Asn Lys Met Leu Ser Leu Trp
        260                 265                 270 agg agt gga gtg aat ccc tgg ctg ctg tgt tca acc tcg tcc atg tgg      921
Arg Ser Gly Val Asn Pro Trp Leu Leu Cys Ser Thr Ser Ser Met Trp
    275                 280                 285 tgt cag gtg tct tct tct acc tgagctcagc tgtcaacccc attatctata         972
Cys Gln Val Ser Ser Ser Thr
290             295 acctactgtc tcgccgcttc caggcagcat tccagaatgt gatctcttct ttccacaaac   1032
agtggcactc ccagcatgac ccacagttgc cacctgccca gcggaacatc ttcctgacag   1092
aatgccactt tgtggagctg accgaagata taggtcccca attcccatgt cagtcatcca   1152
tgcacaactc tcacctccca acagccctct ctagtgaaca gatgtcaaga acaaactatc   1212
aaagcttcca ctttaacaaa acctgaattc tttcagagct gactctcctc tatgcctcaa   1272
aacttcagag aggaacatcc cataatgtat gccttctcat atgatattag agaggtagaa   1332
tggctcttac aactcatgta cccattgcta gttttttttt tttaataaac gtgaaaactg   1392
agagttagat ctggtttcaa aacccaagac tgcctgattt ttagttatct ttccactatc   1452
ctaactgcct catgcccctt cactagttca tgccaagaac gtgactggaa aggcatggca   1512
cctatacctt gattaatttc cattaatgga aatggttcgt cctgagtcat ctacgttccg   1572
agtcaggctg tcactcctac ta                                           1594

<210> SEQ ID NO 10
<211> LENGTH: 296
<212> TYPE: PRT
<213> ORGANISM: Homo sapiens

<400> SEQUENCE: 10

Met Ser Gly Met Glu Lys Leu Gln Asn Ala Ser Trp Ile Tyr Gln Gln
  1               5                  10                  15

Lys Leu Glu Asp Pro Phe Gln Lys His Leu Asn Ser Thr Glu Glu Tyr
             20                  25                  30

Leu Ala Phe Leu Cys Gly Pro Arg Arg Ser His Phe Leu Pro Val
         35                  40                  45

Ser Val Val Tyr Val Pro Ile Phe Val Val Gly Val Ile Gly Asn Val
     50                  55                  60

Leu Val Cys Leu Val Ile Leu Gln His Gln Ala Met Lys Thr Pro Thr
 65                  70                  75                  80

Asn Tyr Tyr Leu Phe Ser Leu Ala Val Ser Asp Leu Leu Val Leu Leu
                 85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
        115                 120                 125

Val Cys Phe Ala Ser Ile Leu Ser Ile Thr Thr Val Ser Val Glu Arg
    130                 135                 140

Tyr Val Ala Ile Leu His Pro Phe Arg Ala Lys Leu Gln Ser Thr Arg
145                 150                 155                 160

Arg Arg Ala Leu Arg Ile Leu Gly Ile Val Trp Gly Phe Ser Val Leu
                165                 170                 175
```

```
Phe Ser Leu Pro Asn Thr Ser Ile His Gly Ile Lys Phe His Tyr Phe
                180                 185                 190

Pro Asn Gly Ser Leu Val Pro Gly Ser Ala Thr Cys Thr Val Ile Lys
            195                 200                 205

Pro Met Trp Ile Tyr Asn Phe Ile Ile Gln Val Thr Ser Phe Leu Phe
        210                 215                 220

Tyr Leu Leu Pro Met Thr Val Ile Ser Val Leu Tyr Tyr Leu Met Ala
225                 230                 235                 240

Leu Arg Leu Lys Lys Asp Lys Ser Leu Glu Ala Asp Glu Gly Asn Ala
                245                 250                 255

Asn Ile Gln Arg Pro Cys Arg Lys Ser Val Asn Lys Met Leu Ser Leu
            260                 265                 270

Trp Arg Ser Gly Val Asn Pro Trp Leu Leu Cys Ser Thr Ser Ser Met
        275                 280                 285

Trp Cys Gln Val Ser Ser Ser Thr
        290                 295

<210> SEQ ID NO 11
<211> LENGTH: 1594
<212> TYPE: DNA
<213> ORGANISM: Homo sapiens
<220> FEATURE:
<221> NAME/KEY: CDS
<222> LOCATION: (64)..(942)
<223> OTHER INFORMATION: IGS4A truncated DNA short version

<400> SEQUENCE: 11
ggctcagctt gaaacagagc ctcgtaccag gggaggctca ggccttggat tttaatgtca        60 ggg atg gaa aaa ctt cag aat gct tcc tgg atc tac cag cag aaa cta       108
    Met Glu Lys Leu Gln Asn Ala Ser Trp Ile Tyr Gln Gln Lys Leu
    1               5                   10                  15 gaa gat cca ttc cag aaa cac ctg aac agc acc gag gag tat ctg gcc       156
Glu Asp Pro Phe Gln Lys His Leu Asn Ser Thr Glu Glu Tyr Leu Ala
                20                  25                  30 ttc ctc tgc gga cct cgg cgc agc cac ttc ttc ctc ccc gtg tct gtg       204
Phe Leu Cys Gly Pro Arg Arg Ser His Phe Phe Leu Pro Val Ser Val
            35                  40                  45 gtg tat gtg cca att ttt gtg gtg ggg gtc att ggc aat gtc ctg gtg       252
Val Tyr Val Pro Ile Phe Val Val Gly Val Ile Gly Asn Val Leu Val
        50                  55                  60 tgc ctg gtg att ctg cag cac cag gct atg aag acg ccc acc aac tac       300
Cys Leu Val Ile Leu Gln His Gln Ala Met Lys Thr Pro Thr Asn Tyr
65                  70                  75 tac ctc ttc agc ctg gcg gtc tct gac ctc ctg gtc ctg ctc ctt gga       348
Tyr Leu Phe Ser Leu Ala Val Ser Asp Leu Leu Val Leu Leu Leu Gly
                85                  90                  95
80 atg ccc ctg gag gtc tat gag atg tgg cgc aac tac cct ttc ttg ttc       396
Met Pro Leu Glu Val Tyr Glu Met Trp Arg Asn Tyr Pro Phe Leu Phe
            100                 105                 110 ggg ccc gtg ggc tgc tac ttc aag acg gcc ctc ttt gag acc gtg tgc       444
Gly Pro Val Gly Cys Tyr Phe Lys Thr Ala Leu Phe Glu Thr Val Cys
        115                 120                 125 ttc gcc tcc atc ctc agc atc acc acc gtc agc gtg gag cgc tac gtg       492
Phe Ala Ser Ile Leu Ser Ile Thr Thr Val Ser Val Glu Arg Tyr Val
    130                 135                 140 gcc atc cta cac ccg ttc cgc gcc aaa ctg cag agc acc cgg cgc cgg       540
Ala Ile Leu His Pro Phe Arg Ala Lys Leu Gln Ser Thr Arg Arg Arg
145                 150                 155 gcc ctc agg atc ctc ggc atc gtc tgg ggc ttc tcc gtg ctc ttc tcc       588
```

-continued

| | | |
|---|---|---|
| Ala Leu Arg Ile Leu Gly Ile Val Trp Gly Phe Ser Val Leu Phe Ser<br>160                         165                   170                   175 | |

```
ctg ccc aac acc agc atc cat ggc atc aag ttc cac tac ttc ccc aat      636
Leu Pro Asn Thr Ser Ile His Gly Ile Lys Phe His Tyr Phe Pro Asn
        180                 185                 190 ggg tcc ctg gtc cca ggt tcg gcc acc tgt acg gtc atc aag ccc atg      684
Gly Ser Leu Val Pro Gly Ser Ala Thr Cys Thr Val Ile Lys Pro Met
    195                 200                 205 tgg atc tac aat ttc atc atc cag gtc acc tcc ttc cta ttc tac ctc      732
Trp Ile Tyr Asn Phe Ile Ile Gln Val Thr Ser Phe Leu Phe Tyr Leu
210                 215                 220 ctc ccc atg act gtc atc agt gtc ctc tac tac ctc atg gca ctc aga      780
Leu Pro Met Thr Val Ile Ser Val Leu Tyr Tyr Leu Met Ala Leu Arg
            225                 230                 235 cta aag aaa gac aaa tct ctt gag gca gat gaa ggg aat gca aat att      828
Leu Lys Lys Asp Lys Ser Leu Glu Ala Asp Glu Gly Asn Ala Asn Ile
240                 245                 250                 255 caa aga ccc tgc aga aaa tca gtc aac aag atg ctg tct ttg tgg agg      876
Gln Arg Pro Cys Arg Lys Ser Val Asn Lys Met Leu Ser Leu Trp Arg
                260                 265                 270 agt gga gtg aat ccc tgg ctg ctg tgt tca acc tcg tcc atg tgg tgt      924
Ser Gly Val Asn Pro Trp Leu Leu Cys Ser Thr Ser Ser Met Trp Cys
            275                 280                 285 cag gtg tct tct tct acc tgagctcagc tgtcaacccc attatctata             972
Gln Val Ser Ser Ser Thr
        290 acctactgtc tcgccgcttc caggcagcat tccagaatgt gatctcttct ttccacaaac   1032 agtggcactc ccagcatgac ccacagttgc cacctgccca gcggaacatc ttcctgacag   1092 aatgccactt tgtggagctg accgaagata taggtcccca attcccatgt cagtcatcca   1152 tgcacaactc tcacctccca acagccctct ctagtgaaca gatgtcaaga acaaactatc   1212 aaagcttcca ctttaacaaa acctgaattc tttcagagct gactctcctc tatgcctcaa   1272 aacttcagag aggaacatcc cataatgtat gccttctcat atgatattag agaggtagaa   1332 tggctcttac aactcatgta cccattgcta gttttttttt tttaataaac gtgaaaactg   1392 agagttagat ctggtttcaa aacccaagac tgcctgattt ttagttatct ttccactatc   1452 ctaactgcct catgccccctt cactagttca tgccaagaac gtgactggaa aggcatggca   1512 cctataccttt gattaatttc cattaatgga aatggttcgt cctgagtcat ctacgttccg   1572 agtcaggctg tcactcctac ta                                           1594
```

<210> SEQ ID NO 12
<211> LENGTH: 293
<212> TYPE: PRT
<213> ORGANISM: Homo sapiens
<400> SEQUENCE: 12

```
Met Glu Lys Leu Gln Asn Ala Ser Trp Ile Tyr Gln Gln Lys Leu Glu
1               5                   10                  15

Asp Pro Phe Gln Lys His Leu Asn Ser Thr Glu Glu Tyr Leu Ala Phe
            20                  25                  30

Leu Cys Gly Pro Arg Arg Ser His Phe Phe Leu Pro Val Ser Val Val
        35                  40                  45

Tyr Val Pro Ile Phe Val Val Gly Ile Gly Asn Val Leu Val Cys
    50                  55                  60

Leu Val Ile Leu Gln His Gln Ala Met Lys Thr Pro Thr Asn Tyr Tyr
65                  70                  75                  80
```

```
Leu Phe Ser Leu Ala Val Ser Asp Leu Leu Val Leu Leu Leu Gly Met
                85                  90                  95

Pro Leu Glu Val Tyr Glu Met Trp Arg Asn Tyr Pro Phe Leu Phe Gly
            100                 105                 110

Pro Val Gly Cys Tyr Phe Lys Thr Ala Leu Phe Glu Thr Val Cys Phe
        115                 120                 125

Ala Ser Ile Leu Ser Ile Thr Thr Val Ser Val Glu Arg Tyr Val Ala
    130                 135                 140

Ile Leu His Pro Phe Arg Ala Lys Leu Gln Ser Thr Arg Arg Arg Ala
145                 150                 155                 160

Leu Arg Ile Leu Gly Ile Val Trp Gly Phe Ser Val Leu Phe Ser Leu
                165                 170                 175

Pro Asn Thr Ser Ile His Gly Ile Lys Phe His Tyr Phe Pro Asn Gly
            180                 185                 190

Ser Leu Val Pro Gly Ser Ala Thr Cys Thr Val Ile Lys Pro Met Trp
        195                 200                 205

Ile Tyr Asn Phe Ile Ile Gln Val Thr Ser Phe Leu Phe Tyr Leu Leu
    210                 215                 220

Pro Met Thr Val Ile Ser Val Leu Tyr Tyr Leu Met Ala Leu Arg Leu
225                 230                 235                 240

Lys Lys Asp Lys Ser Leu Glu Ala Asp Glu Gly Asn Ala Asn Ile Gln
                245                 250                 255

Arg Pro Cys Arg Lys Ser Val Asn Lys Met Leu Ser Leu Trp Arg Ser
            260                 265                 270

Gly Val Asn Pro Trp Leu Leu Cys Ser Thr Ser Ser Met Trp Cys Gln
        275                 280                 285

Val Ser Ser Ser Thr
    290

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:
      Degenerated primer
<220> FEATURE:
<221> NAME/KEY: modified_base
<222> LOCATION: (21)
<223> OTHER INFORMATION: a, c, g or t
<220> FEATURE:
<221> NAME/KEY: modified_base
<222> LOCATION: (24)
<223> OTHER INFORMATION: a, c, g or t

<400> SEQUENCE: 13
ctcatcttcg cggtgggcrc ngyngg                                          26

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Degenerated
      primer
<220> FEATURE:
<221> NAME/KEY: modified_base
<222> LOCATION: (22)
<223> OTHER INFORMATION: c or Inosine
<220> FEATURE:
<221> NAME/KEY: modified_base
<222> LOCATION: (25)
```

<223> OTHER INFORMATION: a, c, g or t
<220> FEATURE:
<221> NAME/KEY: modified_base
<222> LOCATION: (28)
<223> OTHER INFORMATION: a, c, g or t

<400> SEQUENCE: 14
ggccaggcag cgctccgcgc tnarncyngc d            31

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Degenerated
      primer

<400> SEQUENCE: 15
gaartartag ccrcgrcagc cw                      22

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccatcctaat acgactcact atagggc                 27

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
actcactata gggctcgagc ggc                     23

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggatcccaaa taagaaaggg tagttgc                 27

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaagggtagt tgcgccacat ctcatagac               29

<210> SEQ ID NO 20
<211> LENGTH: 29
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 20
aggtctatga gatgtggcgc aactaccct                                    29

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atgtggcgca actacccttt cttatttggg                                   30

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Degenerated
      primer

<400> SEQUENCE: 22
cggaagttgg cggacacgrv rttrta                                       26

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gctcagcttg aaacagagcc tcgtacc                                      27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccatgtggat ctacaatttc atcatcc                                      27

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aagacaaatc tcttgaggca gatgaaggg                                    29

<210> SEQ ID NO 26
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 26
gatgctgttt gtcttggtct tagtgtttgc                                    30

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggatgatgaa attgtagatc cacatgggc                                     29

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgtggagaag tctctcaaag tgtgg                                         25

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tagtaggagt gacagcctga ctcggaacg                                     29

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aacgtagatg actcaggacg aaccatttcc                                    30

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tcgtaccagg ggaggctcag gc                                            22

<210> SEQ ID NO 32
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 32
cctcttcagc ctggcggtct ctg                                              23

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggaggcgaag cacacggtct ca                                               22

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_binding
<222> LOCATION: (1)
<223> OTHER INFORMATION: Labeled with 6-carboxyfluorescein
<220> FEATURE:
<221> NAME/KEY: misc_binding
<222> LOCATION: (34)
<223> OTHER INFORMATION: Labeled with
      N,N,N',N'-tetramethyl-6-carboxyrhodamin

<400> SEQUENCE: 34
agatgtggcg caactaccct ttcttgttcg ggcc                                  34

<210> SEQ ID NO 35
<211> LENGTH: 7
<212> TYPE: PRT
<213> ORGANISM: Unknown Organism
<220> FEATURE:
<223> OTHER INFORMATION: Description of Unknown Organism: Illustrative
      mammalian C-terminal sequence
<220> FEATURE:
<223> OTHER INFORMATION: C-term amidated

<400> SEQUENCE: 35

Phe Leu Phe Arg Pro Arg Asn
 1               5
```

The invention claimed is:

1. An isolated polynucleotide comprising a nucleotide sequence chosen from:
   a) a nucleotide sequence having at least 99% sequence identity over its entire length to SEQ ID NO: 1, SEQ ID NO: 3, SEQ ID NO: 5 or SEQ ID NO: 7;
   b) a nucleotide sequence encoding a polypeptide having at least 99% sequence identity over its entire length according to SEQ ID NO: 2, SEQ ID NO: 4, SEQ ID NO: 6 or SEQ ID NO: 8;
   c) a nucleotide sequence having at least 99% identity over its entire length to a DNA insert contained in deposit no. CBS102221 or deposit no. CBS102222 at the Centraalbureau voor Schimmelcultures at Baarn the Netherlands; or
   d) a nucleotide sequence which is complimentary to the nucleotide sequence of (a) or (b) or (c).

2. The isolated polynucleotide of claim 1 that is DNA or RNA.

3. The isolated polynucleotide of claim 1, wherein said polynuceotide encodes a neuromedin receptor protein which exhibits ligand binding for neuromedin U with a log $EC_{50}$ value of at least below −6.00.

4. The isolated polynucleotide of claim 3, wherein the neuromedin receptor protein is a mammalian neuromedin receptor protein and neuromedin U is at least one of neuromedin U-8, neuromedin U-23, and neuromedin U-25.

5. The isolated polynucleotide of claim 3, wherein said neuromedin receptor protein is expressed in at least one of brain, skeletal muscle, cerebellum, testis, corpus callosum, spinal cord, substantia nigra, medulla, thalamus, caudate nucleus, pons, nucleus accumbens, fetal brain, stomach, heart, thyroid gland, lung, thymus, prostate, and trachea.

6. An expression system comprising a recombinant DNA or RNA molecule encoding an amino acid sequence with at least 99% identity along its entire length to SEQ ID NO: 2, SEQ ID NO: 4, SEQ ID NO: 6 or SEQ ID NO: 8 or a polypeptide encoded by a DNA insert contained in deposit no. CBS102221 or deposit no. CBS 102222 at the Centraalbureau voor Schimmelcultures at Baarn the Netherlands, wherein said expression system produces a polypeptide comprising an amino acid sequence with at least 99% sequence identity to SEQ ID NO: 2, SEQ ID NO: 4, SEQ ID NO: 6 or SEQ ID NO: 8 or to the polypeptide encoded by the DNA insert contained in deposit no. CBS1 02221 or deposit no. CBS1 02222 at the Centraalbureau voor Schimmelcultures at Baarn the Netherlands, when said expression system is present in a compatible host cell.

7. The expression system of claim 6, wherein said produced polypeptide is a neuromedin receptor protein that exhibits ligand binding for neuromedin U with a log $EC_{50}$ value of at least below −6.00, and is expressed in at least one of brain, skeletal muscle, cerebellum, testis, corpus callosum, spinal cord, substantia nigra, medulla, thalamus, caudate nucleus, pons, nucleus accumbens, fetal brain, stomach, heart, thyroid gland, lung, thymus, prostate, and trachea.

8. The expression system of claim 7, wherein the neuromedin receptor protein is a mammalian neuromedin receptor protein and neuromedin U is at least one of neuromedin U-8, neuromedin U-23, and neuromedin U-25.

9. A host cell comprising the expression system of claim 7.

10. A host cell comprising the expression system of claim 8.

11. The host cell according to claim 9 wherein the host cell is a yeast cell.

12. The host cell according to claim 9 wherein the host cell is an animal cell.

13. A process for producing a polypeptide having at least 99% sequence identity along its entire length to SEQ ID NO: 2, SEQ ID NO: 4, SEQ ID NO: 6, or SEQ ID NO: 8 comprising culturing the host cell of claim 12 under conditions sufficient for the production of said polypeptide and recovering the polypeptide from the culture.

14. A process for producing a cell which produces a polypeptide having at least 99% sequence identity along its entire length to SEQ ID NO: 2, SEQ ID NO: 4, SEQ ID NO: 6, or SEQ ID NO: 8 comprising transforming or transfecting a host cell with the expression system of claim 6 such that the host cell, under appropriate culture conditions, produces a neuromedin receptor protein having at least 99% sequence identity along its entire length to SEQ ID NO: 2, SEQ ID NO: 4, SEQ ID NO: 6, or SEQ ID NO: 8.

15. A recombinant host cell, produced by the method of claim 14 wherein the host cell expresses a neuromedin receptor protein.

* * * * *